(12) United States Patent
Fadli et al.

(10) Patent No.: US 7,635,394 B2
(45) Date of Patent: *Dec. 22, 2009

(54) COMPOSITION FOR THE DYEING OF KERATIN FIBERS COMPRISING AT LEAST ONE 3-AMINO-PYRAZOLOPYRIDINE DERIVATIVES

(75) Inventors: Aziz Fadli, Chelles (FR); Laurent Vidal, Paris (FR); Stéphane Sabelle, Paris (FR)

(73) Assignee: L'Oreal S.A., Paris (FR)

( * ) Notice: Subject to any disclaimer, the term of this patent is extended or adjusted under 35 U.S.C. 154(b) by 61 days.

This patent is subject to a terminal disclaimer.

(21) Appl. No.: 11/594,967

(22) Filed: Nov. 9, 2006

(65) Prior Publication Data

US 2007/0143935 A1    Jun. 28, 2007

Related U.S. Application Data

(60) Provisional application No. 60/737,462, filed on Nov. 17, 2005.

(30) Foreign Application Priority Data

Nov. 9, 2005    (FR) .................................. 05 53403

(51) Int. Cl.
*A61Q 5/10* (2006.01)
*C07D 515/02* (2006.01)
*C07D 513/02* (2006.01)

(52) U.S. Cl. ...................... 8/405; 8/406; 8/407; 8/410; 8/411; 8/435; 8/568; 8/570; 8/571; 8/574; 8/669; 8/670; 546/121

(58) Field of Classification Search ................. 8/405, 8/406, 407, 410, 411, 435, 568, 570, 571, 8/574, 669, 670; 546/121

See application file for complete search history.

(56) References Cited

U.S. PATENT DOCUMENTS

| | | | |
|---|---|---|---|
| 2,841,584 A | 7/1958 | Hunter et al. | |
| 4,003,699 A | 1/1977 | Rose et al. | |
| 4,128,425 A | 12/1978 | Greenwald | |
| RE30,199 E | 1/1980 | Rose et al. | |
| 4,823,985 A | 4/1989 | Grollier et al. | |
| 5,061,289 A | 10/1991 | Clausen et al. | |
| 5,234,818 A | 8/1993 | Zimmermann et al. | |
| 5,380,340 A | 1/1995 | Neunhoeffer et al. | |
| 5,457,200 A | 10/1995 | Zimmermann et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,027,538 A | 2/2000 | Vandenbossche et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 * | 5/2004 | Birault et al. | ................ 546/121 |
| 7,091,215 B2 | 8/2006 | Hibi et al. | |
| 7,285,666 B2 | 10/2007 | Hibi et al. | |
| 2002/0032934 A1 | 3/2002 | Kravtchenko et al. | |
| 2006/0277691 A1 | 12/2006 | Saunier | |
| 2006/0277693 A1 | 12/2006 | Saunier | |
| 2007/0136959 A1 | 6/2007 | Fadli | |
| 2007/0143935 A1 | 6/2007 | Fadli et al. | |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 433 854 | 6/1991 |
| EP | 0 770 375 | 5/1997 |
| EP | 1 155 680 | 11/2001 |
| EP | 1 233 743 | 8/2002 |
| EP | 1 389 618 | 2/2004 |
| EP | 1 586 302 | 10/2005 |
| EP | 1 733 714 | 12/2006 |
| EP | 1 792 606 | 6/2007 |
| EP | 1 792 903 | 6/2007 |
| FR | A 2 733 749 | 5/1995 |
| FR | 2 750 048 B1 | 9/1998 |

(Continued)

OTHER PUBLICATIONS

STIC Search Report dated Apr. 9, 2008.*

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

Disclosed herein is a composition for the dyeing of keratin fibers, for example, human keratin fibers such as the hair, comprising at least one 3-amino pyrazolo-[1,5-a]-pyridine derivative or one of its addition salts and a method employing this derivative. The composition of the present disclosure makes it possible to obtain coloration in various shades that is powerful, chromatic, and aesthetic, with low selectivity and with good resistance to various aggressive factors to which the hair may be subjected, such as shampoos, the light, sweat and permanent shaping.

13 Claims, No Drawings

FOREIGN PATENT DOCUMENTS

| | | |
|---|---|---|
| FR | 2 767 475 | 2/1999 |
| FR | 2 801 308 | 11/1999 |
| FR | 2 586 913 | 3/2001 |
| FR | 2 822 689 | 10/2002 |
| FR | 2 822 690 | 10/2002 |
| FR | 2 822 691 | 10/2002 |
| FR | 2 822 692 | 10/2002 |
| FR | 2 886 137 | 12/2006 |
| FR | 2 886 139 | 12/2006 |
| GB | 1 026 978 | 4/1966 |
| GB | 1 153 196 | 5/1969 |
| JP | 2-19576 | 1/1990 |
| JP | 05-163124 | 6/1993 |
| JP | 2526099 | 8/1996 |
| WO | WO 94/08969 | 4/1994 |
| WO | WO 94/08970 | 4/1994 |
| WO | WO 96/15765 | 5/1996 |
| WO | WO 01/35917 | 5/2001 |
| WO | WO 02/076416 | 10/2002 |
| WO | WO 02/076417 | 10/2002 |
| WO | WO 02/076418 | 10/2002 |

OTHER PUBLICATIONS

Boros, E. et al. 2001. "A Convenient Synthesis of Pyrazolidine and 3-Amino-6,7-dihydro-1*H*,5*H*-pyrazolo[1,2-α]pyrazol-1-one". *J. Heterocyclic Chem.* 38: 613-616.

Cohen, S. and Zand, R. 1962. "Bicyclic, Cyclic and Acyclic Azo Compounds, 2,3-Diazabicyclo[2,2,2]-2-octene, 3,6-Dimethyl-$\Delta^1$-tetrahydropyridazine and Aziosopropane". *J. Am. Chem. Soc.* 84: 586-591.

Heyman, M. and Snyder, J. 1973. "An Efficient Synthesis of Bicyclic Hydrazines and Azo Alkanes". *Tetrahedron Letters* 14(30): 2859-2862.

Kharasch, N. and Bruice, T. 1951. "Derivatives of Sulfenic Acids V. 1-Fluorenone Sulfur Compounds". *J. Am. Chem. Soc.* 73: 3240-3244.

Lingens, F. and Schneider-Bernlöhr, H. 1965. "Über die Umsetzung Natülich Vorkommender Pyrimidinbasen mit Hydrazin und Methylsubstituierten Hydrazinen". *Justus Liebigs Ann. Chem.* 686: 134-145.

Magnien, E. and Baltzly, R. 1958. "A Re-examination of Limitations of the Hofmann Reaction". *J. Org. Chem.* 23: 2029-2032.

Stenzl, H. et al. 1950. "Zur Kenntnis der 3-Amino-pyrazolone-(5)". *Helvetica Chimica Acta* 33(5): 1183-1194.

Fujito, H. et al. 1977. "Reaction of Pyrisnium and Isoquinolinium N-imines with Ketenethioacetals". *Heterocycles* 6(4): 379-382.

March, J. *Advanced Organic Chemistry*, 3rd ed. (Wiley-Interscience, New York, USA, 1985) pp. 1048-1051, 1093-1120.

Hudlicky, M. *Reductions in Organic Chemistry*, (Ellis Horwood Limited, Chichester, England, 1983) pp. 1-13, 22-31.

French Search Report for FR 05 53403 (French priority application for the present application) dated Jul. 24, 2006.

French Search Report for FR 05 53402 (French priority application for co-pending U.S. Appl. No. 11/594,957) dated Aug. 29, 2006.

Office Action for co-pending U.S. Appl. No. 11/594,957, dated Jun. 30, 2008.

Co-pending U.S. Appl. No. 11/594,957, filed Nov. 9, 2006.
Co-pending U.S. Appl. No. 12/149,871, filed May 9, 2008.
Co-pending U.S. Appl. No. 12/149,872, filed May 9, 2008.
English language Abstract of EP 1 586 302, dated Oct. 19, 2005.
English language Abstract of WO 02/076418, dated Oct. 3, 2002.
English language Derwent Abstract of JP 2-19576, dated Jan. 23, 1990.
English language Derwent Abstract of JP 2526099, dated Aug. 21, 1996.

French Search Report for FR 07/54947, dated Dec. 17, 2007, (French priority application for U.S. Appl. No. 12/149,872).

French Search Report for FR 07/54948, dated Dec. 13, 2007, (French priority application for U.S. Appl. No. 12/149,871).

Notice of Allowance mailed Apr. 28, 2009, in co-pending U.S. Appl. No. 11/594,957.

Notice of Allowance mailed Jan. 12, 2009, in co-pending U.S. Appl. No. 11/594,957.

Notice of Allowance mailed Apr. 30, 2009, in co-pending U.S. Appl. No. 12/149,872.

Notice of Allowance mailed Jan. 21, 2009, in co-pending U.S. Appl. No. 12/149,872.

Notice of Allowance mailed Oct. 7, 2008, in co-pending U.S. Appl. No. 12/149,872.

Office Action mailed Feb. 6, 2009, in co-pending U.S. Appl. No. 12/149,871.

STIC Search Report dated Apr. 9, 2008, for U.S. Appl. No. 11/594,957.

STIC Search Report dated Sep. 9, 2008, for U.S. Appl. No. 12/149,872.

* cited by examiner

COMPOSITION FOR THE DYEING OF KERATIN FIBERS COMPRISING AT LEAST ONE 3-AMINO-PYRAZOLOPYRIDINE DERIVATIVES

This application claims benefit of U.S. Provisional Application No. 60/737,462, filed Nov. 17, 2005, the contents of which are incorporated herein by reference. This application also claims benefit of priority under 35 U.S.C. § 119 to French Patent Application No. FR 05 53403, filed Nov. 9, 2005, the contents of which are also incorporated herein by reference.

The present disclosure relates to a composition for the dyeing of keratin fibers, for example, human keratin fibers such as the hair, comprising at least one 3-aminopyrazolo-[1,5-a]-pyridine derivative and/or addition salts thereof and a method employing this composition. It also relates to 3-aminopyrazolo-[1,5-a]-pyridine derivatives and addition salts thereof.

The dyeing of keratin fibers, for example, human keratin fibers such as the hair, with dyeing compositions comprising oxidation dye precursors, including ortho- or para-phenylenediamines, ortho- or para-aminophenols, and heterocyclic compounds generally called oxidation bases, is known. Oxidation dye precursors, or oxidation bases, are compounds that are colorless or slightly colored, which, when combined with oxidizing products, can give rise to colored or coloring compounds by a process of oxidative condensation.

It is also known that the shades obtained with these oxidation bases can be varied by combining them with couplers or dyeing modifiers, the latter being chosen, for example, from the meta-phenylenediamines, the meta-aminophenols, the meta-hydroxyphenols and certain heterocyclic compounds such as, for example, derivatives of pyrazolo[1,5-b]-1,2,4-triazoles, derivatives of pyrazolo[3,2-c]-1,2,4-triazoles, derivatives of pyrazolo[1,5-a]pyrimidines, derivatives of pyridine, derivatives of pyrazol-5-one, derivatives of indoline and derivatives of indole.

The variety of molecules employed in the oxidation bases and couplers means that a rich palette of colors can be obtained.

The so-called "permanent" dyeing obtained with these oxidation dyes ideally, moreover, has at least one of the following advantages: the dyes do not pose any problems in toxicological terms, make it possible to obtain shades of desired intensity, provide good resistance to external factors such as the light, weather, washing, permanent waving, sweating and rubbing, provide coverage of white hair, and/or finally they have the least possible selectivity, i.e., ensuring the slightest possible differences in coloration all the way along one and the same keratin fiber, which may in fact have different sensitivity (i.e. extent of damage) between its tip and its root. The dyes also ideally display good chemical stability in the formulations and have a good toxicological profile.

The use of oxidation bases such as the derivatives of para-phenylenediamine and para-aminophenol may make it possible to obtain quite a wide range of colors at basic pH, though without achieving shades with good chromaticity, while endowing the hair with at least one excellent property chosen from color intensity, variety of shades, uniformity of color and/or resistance to external factors.

However, the use of these bases at neutral pH is may be ineffective for achieving a range of varied shades, for example, for warm shades.

European Patent Application EP 1 233 743 has already proposed dye compositions containing 3-amino-pyrazolo-[1,5-a]-pyridines as the oxidation base. However, the dye compositions described in that document may not always make it possible to achieve good properties of chromaticity and/or resistance to external factors such as washing and the light. Moreover, the range of shades may be of a limited extent.

Thus, it would be desirable to supply novel oxidation bases for the dyeing of keratin fibers which overcome at least one of the drawbacks of the existing oxidation bases. For instance, it would be desirable to supply novel oxidation bases which make it possible to obtain dyeing in a variety of shades that is powerful, chromatic, aesthetic, of low selectivity, and/or has good resistance to the various aggressive factors to which the hair may be subjected, such as shampoos, light, sweat and permanent shaping.

The present disclosure, therefore, relates, in at least one embodiment, to dyeing compounds and compositions which make it possible to obtain dyeing having at least one of the above-discussed advantageous properties. More specifically, the present disclosure relates to a composition for dyeing keratin fibers comprising, in a medium that is suitable for dyeing, at least one oxidation dyeing base chosen from 3-aminopyrazolo-[1,5-a]-pyridine derivatives of the following formula (I) and salts and solvates thereof:

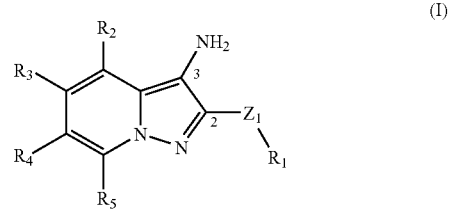

in which
  $Z_1$ is chosen from an oxygen atom and a group $NR_6$; when $Z_1$ represents $NR_6$, $R_1$ and $R_6$ can form, together with the nitrogen atom to which they are attached, a saturated, unsaturated or aromatic heterocycle with 5 to 8 ring members, optionally substituted,
  $Z_1$ can also be a divalent radical chosen from S, SO, and $SO_2$ when $R_1$ is a methyl radical,
  $R_1$ and $R_2$ are chosen from, independently:
    a hydrogen atom,
    $C_1$-$C_{10}$ alkyl radicals, optionally substituted, and the substituent can optionally be a saturated, unsaturated or aromatic (hetero)cycle with 5 to 8 ring members, optionally substituted,
    saturated, unsaturated or aromatic (hetero)cycles with 5 to 8 ring members, optionally substituted,
  $R_3$, $R_4$, and $R_5$, independently, are chosen from:
    a hydrogen atom,
    $C_1$-$C_4$ alkyl radicals, optionally substituted,
    an entity chosen from $NH_2$, $NHR_{10}$, $NR_{11}R_{12}$, OH, and $OR_9$, wherein $R_9$ and $R_{10}$, which may be identical or different are chosen from linear or branched $C_1$-$C_6$ alkyl groups, optionally substituted; $R_{11}$ and $R_{12}$, which may be identical or different, are chosen from linear or branched $C_1$-$C_6$ alkyl groups, optionally substituted; and $R_{11}$ and $R_{12}$ can form, together with the nitrogen atom to which they are attached, a saturated, unsaturated or aromatic heterocycle with 5 to 8 ring members optionally containing at least one other heteroatom or group chosen from N, O, S, $SO_2$, and CO, the heterocycle being optionally substituted,
  $R_2$, $R_3$, $R_4$, $R_5$ can form, two by two with the adjacent radicals, saturated or unsaturated (hetero)cycles, optionally substituted, with the exception of 2-methoxypyrazolo[1,5-a]pyridin-3-ylamine and 2-morpholino-pyrazolo[1,5-a]pyridin-3-ylamine respectively with the following formulae:

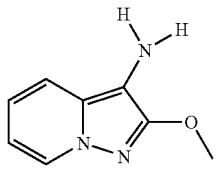

2-Methoxypyrazolo[1,5-a]pyridin-3-ylamine

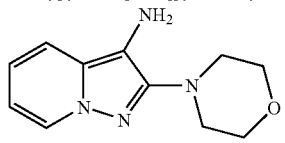

2-Morpholin-4-yl-pyrazolo[1,5-a]pyridin-3-ylamine

In at least one embodiment, the compositions and compounds of the present disclosure make it possible to obtain fast dyeing of keratin fibers, resistant to light and to washing.

Another embodiment relates to a method of dyeing keratin fibers employing the composition disclosed herein, as well as the use of this composition for the dyeing of keratin fibers.

The present disclosure also relates to novel pyrazolopyridine derivatives of formula (I) except 2-methylsulfanyl-pyrazolo[1,5-a]pyridin-3-ylamine and 2,3-diamino-pyrazolo[1,5-a]pyridine and their corresponding nitro or nitroso derivatives.

As used herein, "alkyl radical" means linear or branched alkyl radicals, which can be substituted or unsubstituted. They can be substituted with any conventional substituent in the field of dyeing which does not alter the properties of oxidation base of the compounds of formula (I).

Similarly, when the (hetero)cyclic radicals defined for formula (I) are substituted, they can be substituted with any conventional radical in the field of dyeing which does not alter the properties of oxidation base of the compounds of formula (I). The following may be mentioned as examples of substituents of the rings or heterocycles: alkyl radicals, substituted alkyl radicals, hydroxy, alkoxy, amino, alkylamino, dialkylamino, thio, alkylthio, carboxy, alkylcarbonyl, sulphonyl, amido radicals etc.

The nitrogen-containing heterocycle formed by $R_1$ and $R_6$ can contain at least one other heteroatom, such as a heteroatom selected from N, O, S, SO, $SO_2$, —CO— and combinations thereof. It can, moreover, be substituted or unsubstituted, as described above.

The compounds of formula (I) can optionally be salified by strong mineral acids such as HCl, HBr, HI, $H_2SO_4$, $H_3PO_4$, or organic acids such as acetic, lactic, tartaric, citric or succinic, benzenesulphonic, para-toluenesulphonic, formic or methanesulphonic acid.

They can also be in the form of solvates, for example a hydrate or a solvate of a linear or branched alcohol such as ethanol or isopropanol.

As used herein, "derivative of formula (I)" means all mesomeric or isomeric forms.

In formula (i) above, when $R_1$ and/or $R_6$ represent a substituted alkyl radical, the substituents may, in at least one embodiment, be chosen from halogens, and from —OH, —$OR_9$, —$NH_2$, —$NHR_{10}$, —$NR_{11}R_{12}$, —$COR_{13}$, —O—CO—$R_{13}$, —CO—$OR_{14}$, —$NR_{15}$—CO—$R_{16}$, —CO—$NR_{15}R_{16}$, and —$SO_3H$ radicals, the saturated or unsaturated cyclic radicals optionally containing a heteroatom chosen from N, S, O, the ring itself possibly being substituted, in which $R_9$, $R_{10}$, $R_{11}$, and $R_{12}$, which may be identical or different, are as defined previously; $R_{13}$, $R_{14}$, $R_{15}$ and $R_{16}$, which may be identical or different, are chosen from hydrogen and $C_1$-$C_6$ alkyl radicals. In formula (I) above, when $R_1$ and/or $R_6$ represent a substituted alkyl radical, the substituents are also chosen from the —$OSO_2R$ radicals, wherein R is chosen from a linear or branched $C_1$-$C_4$ alkyl radical and an aromatic radical, optionally substituted. The following may be mentioned as examples: —OH, —$OR_9$, —$NH_2$, —$NHR_{10}$, —$NR_{11}R_{12}$, —$COR_{13}$ radicals, and cyclic radicals such as imidazole, piperazine, pyrrolidine, pyridine, piperidine, morpholine, pyrimidine.

As examples of derivatives of formula (I), the following compounds or their addition salts or solvates may be mentioned:

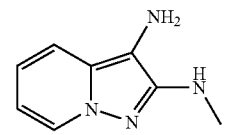

N-2-Methylpyrazolo[1,5-a]pyridine-2,3-diamine

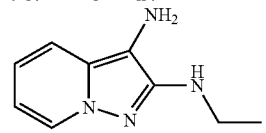

N-2-Ethylpyrazolo[1,5-a]pyridine-2,3-diamine

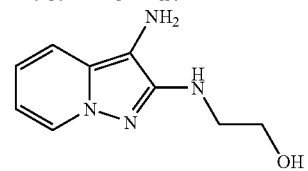

(3-Aminopyrazolo[1,5-a]pyridin-2-ylamino)methanol

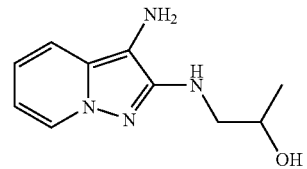

1-(3-Aminopyrazolo[1,5-a]pyridin-2-ylamino)propan-2-ol

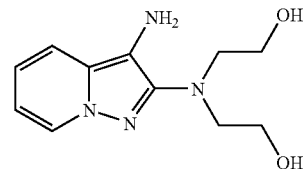

2-[(3-Aminopyrazolo[1,5-a]pyridin-2-yl)(2-hydroxyethyl)amino]ethanol

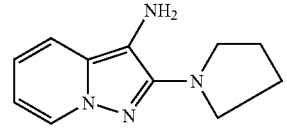

2-Pyrrolidin-1-ylpyrazolo[1,5-a]pyridin-3-ylamine

-continued

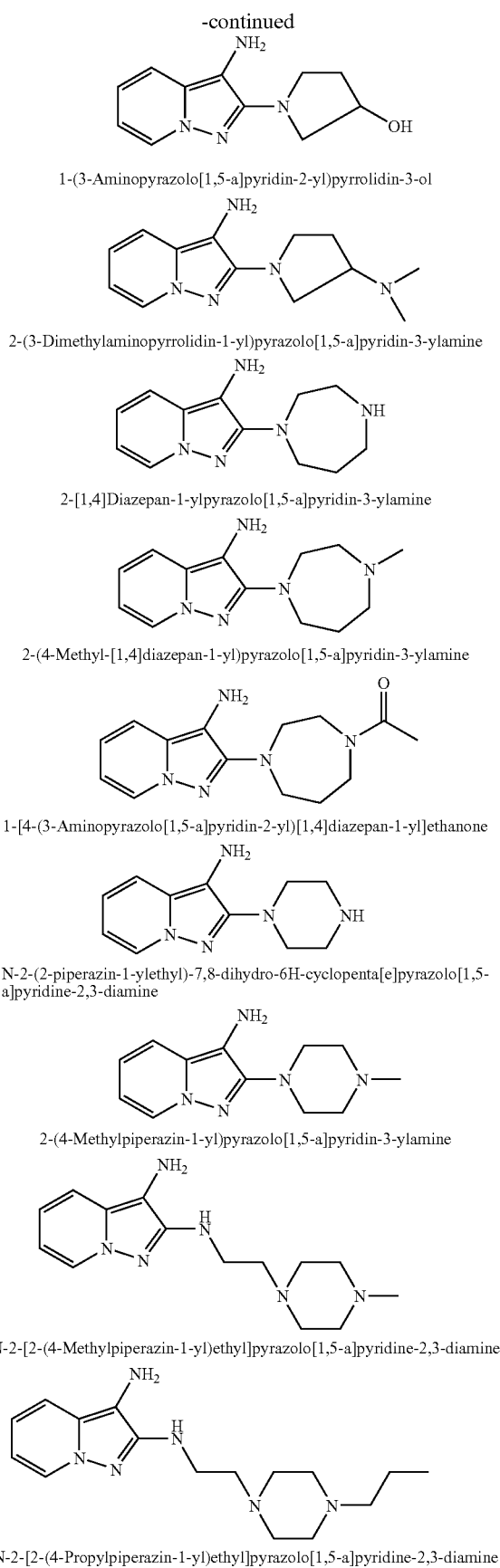

1-(3-Aminopyrazolo[1,5-a]pyridin-2-yl)pyrrolidin-3-ol 2-(3-Dimethylaminopyrrolidin-1-yl)pyrazolo[1,5-a]pyridin-3-ylamine 2-[1,4]Diazepan-1-ylpyrazolo[1,5-a]pyridin-3-ylamine 2-(4-Methyl-[1,4]diazepan-1-yl)pyrazolo[1,5-a]pyridin-3-ylamine 1-[4-(3-Aminopyrazolo[1,5-a]pyridin-2-yl)[1,4]diazepan-1-yl]ethanone N-2-(2-piperazin-1-ylethyl)-7,8-dihydro-6H-cyclopenta[e]pyrazolo[1,5-a]pyridine-2,3-diamine 2-(4-Methylpiperazin-1-yl)pyrazolo[1,5-a]pyridin-3-ylamine N-2-[2-(4-Methylpiperazin-1-yl)ethyl]pyrazolo[1,5-a]pyridine-2,3-diamine N-2-[2-(4-Propylpiperazin-1-yl)ethyl]pyrazolo[1,5-a]pyridine-2,3-diamine -continued

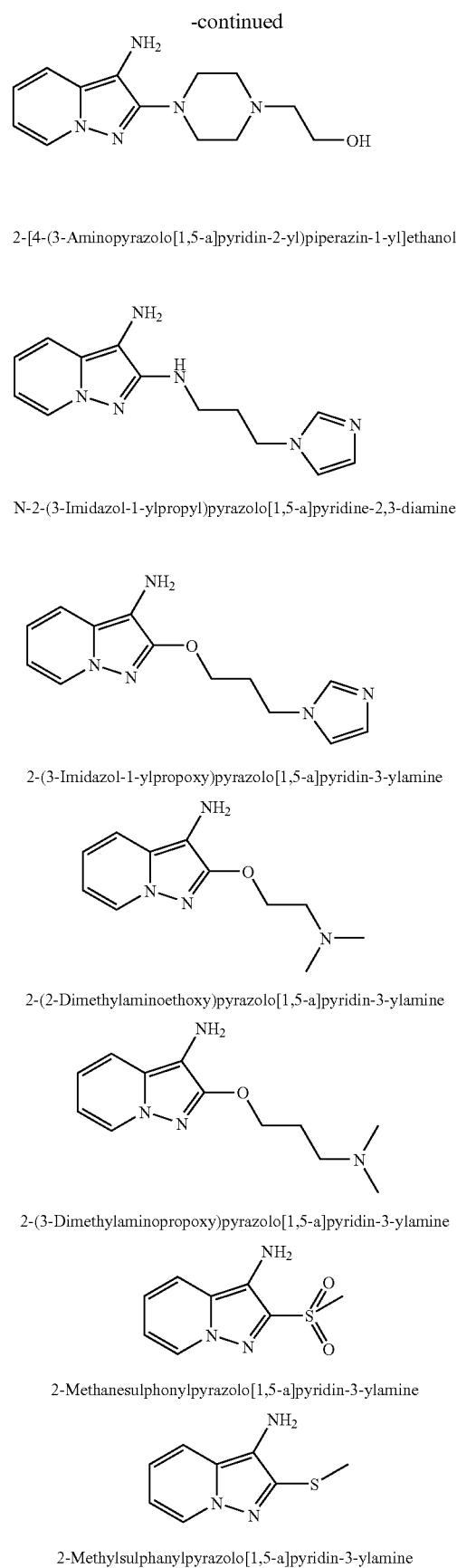

2-[4-(3-Aminopyrazolo[1,5-a]pyridin-2-yl)piperazin-1-yl]ethanol

N-2-(3-Imidazol-1-ylpropyl)pyrazolo[1,5-a]pyridine-2,3-diamine 2-(3-Imidazol-1-ylpropoxy)pyrazolo[1,5-a]pyridin-3-ylamine 2-(2-Dimethylaminoethoxy)pyrazolo[1,5-a]pyridin-3-ylamine 2-(3-Dimethylaminopropoxy)pyrazolo[1,5-a]pyridin-3-ylamine 2-Methanesulphonylpyrazolo[1,5-a]pyridin-3-ylamine 2-Methylsulphanylpyrazolo[1,5-a]pyridin-3-ylamine -continued

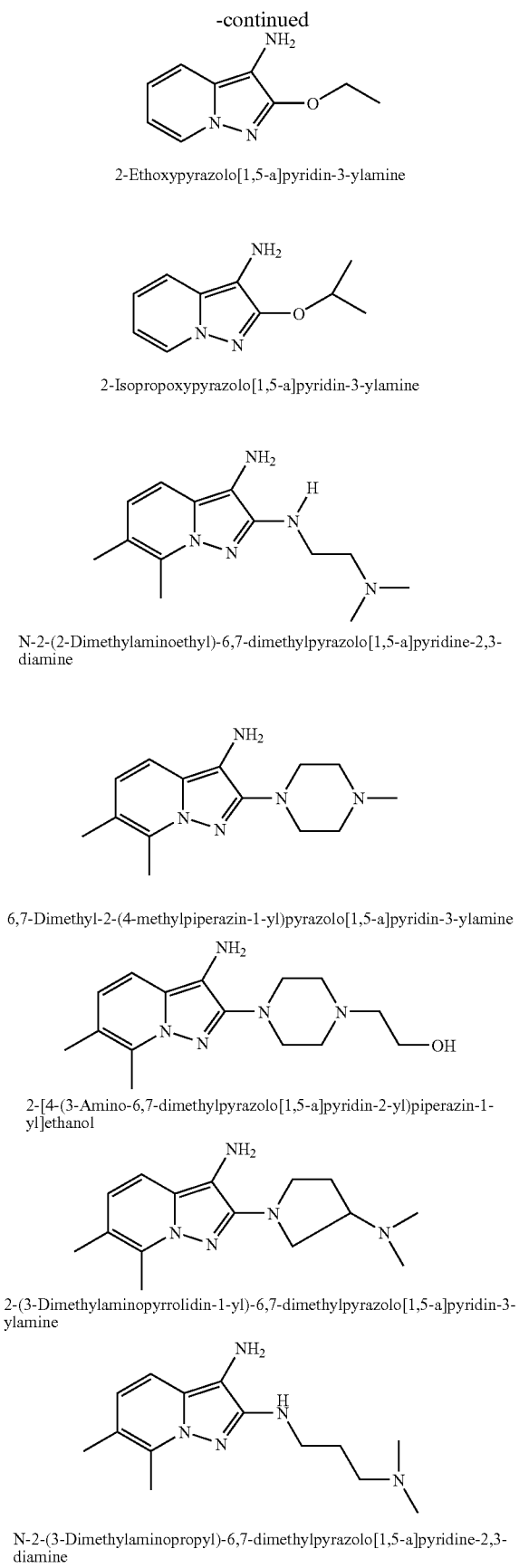

2-Ethoxypyrazolo[1,5-a]pyridin-3-ylamine

2-Isopropoxypyrazolo[1,5-a]pyridin-3-ylamine

N-2-(2-Dimethylaminoethyl)-6,7-dimethylpyrazolo[1,5-a]pyridine-2,3-diamine 6,7-Dimethyl-2-(4-methylpiperazin-1-yl)pyrazolo[1,5-a]pyridin-3-ylamine 2-[4-(3-Amino-6,7-dimethylpyrazolo[1,5-a]pyridin-2-yl)piperazin-1-yl]ethanol 2-(3-Dimethylaminopyrrolidin-1-yl)-6,7-dimethylpyrazolo[1,5-a]pyridin-3-ylamine N-2-(3-Dimethylaminopropyl)-6,7-dimethylpyrazolo[1,5-a]pyridine-2,3-diamine -continued

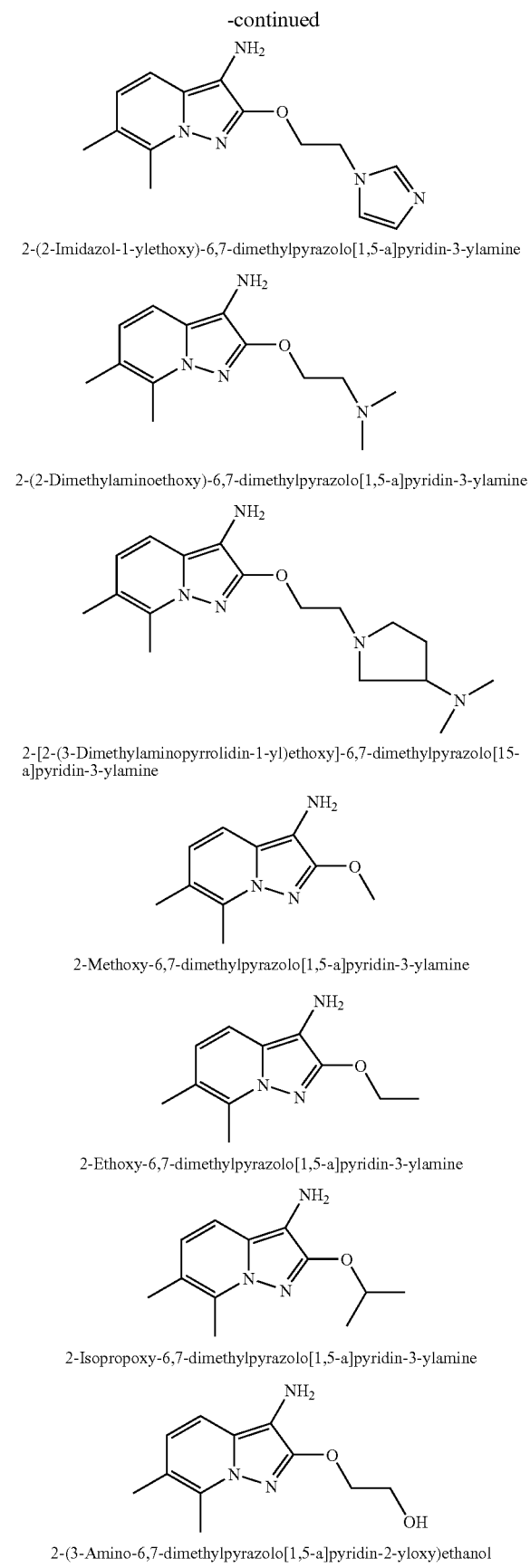

2-(2-Imidazol-1-ylethoxy)-6,7-dimethylpyrazolo[1,5-a]pyridin-3-ylamine 2-(2-Dimethylaminoethoxy)-6,7-dimethylpyrazolo[1,5-a]pyridin-3-ylamine 2-[2-(3-Dimethylaminopyrrolidin-1-yl)ethoxy]-6,7-dimethylpyrazolo[15-a]pyridin-3-ylamine 2-Methoxy-6,7-dimethylpyrazolo[1,5-a]pyridin-3-ylamine 2-Ethoxy-6,7-dimethylpyrazolo[1,5-a]pyridin-3-ylamine 2-Isopropoxy-6,7-dimethylpyrazolo[1,5-a]pyridin-3-ylamine 2-(3-Amino-6,7-dimethylpyrazolo[1,5-a]pyridin-2-yloxy)ethanol -continued

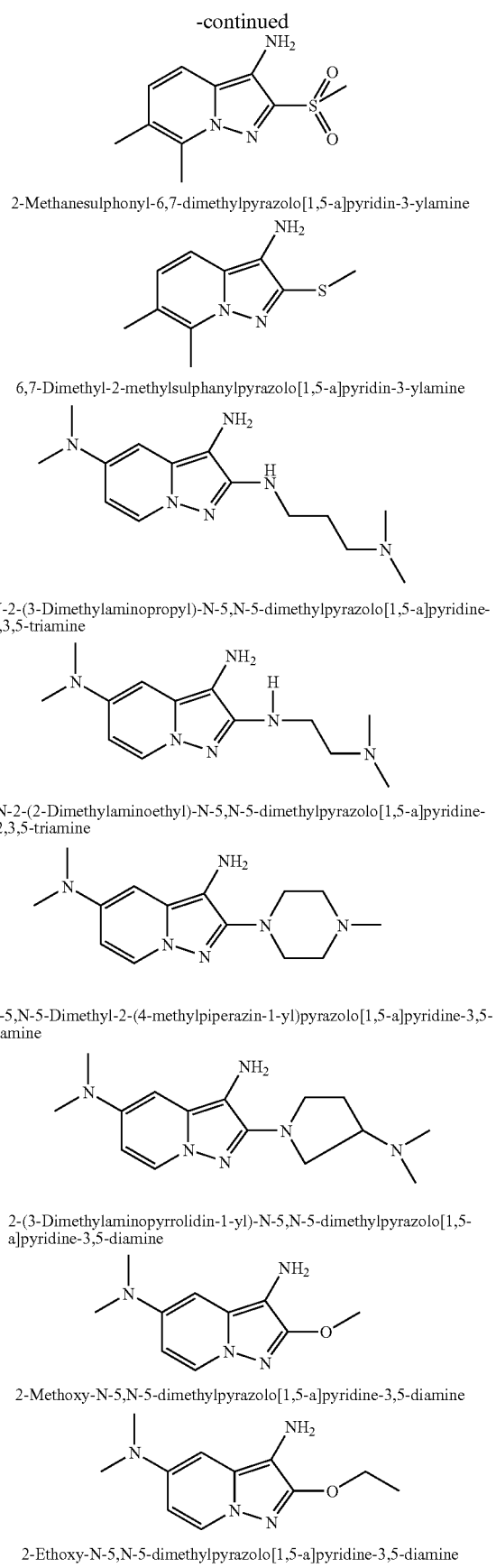

2-Methanesulphonyl-6,7-dimethylpyrazolo[1,5-a]pyridin-3-ylamine 6,7-Dimethyl-2-methylsulphanylpyrazolo[1,5-a]pyridin-3-ylamine N-2-(3-Dimethylaminopropyl)-N-5,N-5-dimethylpyrazolo[1,5-a]pyridine-2,3,5-triamine N-2-(2-Dimethylaminoethyl)-N-5,N-5-dimethylpyrazolo[1,5-a]pyridine-2,3,5-triamine N-5,N-5-Dimethyl-2-(4-methylpiperazin-1-yl)pyrazolo[1,5-a]pyridine-3,5-diamine 2-(3-Dimethylaminopyrrolidin-1-yl)-N-5,N-5-dimethylpyrazolo[1,5-a]pyridine-3,5-diamine 2-Methoxy-N-5,N-5-dimethylpyrazolo[1,5-a]pyridine-3,5-diamine 2-Ethoxy-N-5,N-5-dimethylpyrazolo[1,5-a]pyridine-3,5-diamine -continued

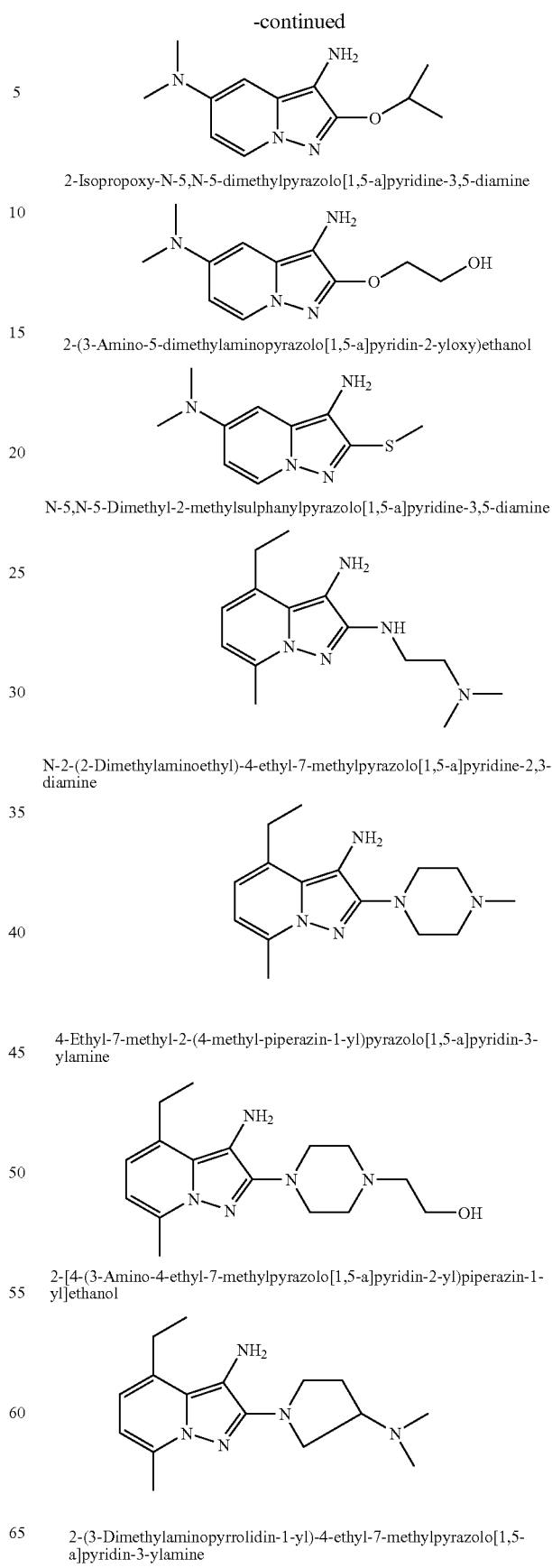

2-Isopropoxy-N-5,N-5-dimethylpyrazolo[1,5-a]pyridine-3,5-diamine 2-(3-Amino-5-dimethylaminopyrazolo[1,5-a]pyridin-2-yloxy)ethanol N-5,N-5-Dimethyl-2-methylsulphanylpyrazolo[1,5-a]pyridine-3,5-diamine N-2-(2-Dimethylaminoethyl)-4-ethyl-7-methylpyrazolo[1,5-a]pyridine-2,3-diamine 4-Ethyl-7-methyl-2-(4-methyl-piperazin-1-yl)pyrazolo[1,5-a]pyridin-3-ylamine 2-[4-(3-Amino-4-ethyl-7-methylpyrazolo[1,5-a]pyridin-2-yl)piperazin-1-yl]ethanol 2-(3-Dimethylaminopyrrolidin-1-yl)-4-ethyl-7-methylpyrazolo[1,5-a]pyridin-3-ylamine -continued

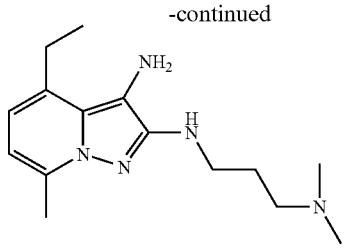

N-2-(3-Dimethylaminopropyl)-4-ethyl-7-methylpyrazolo[1,5-a]pyridine-2,3-diamine

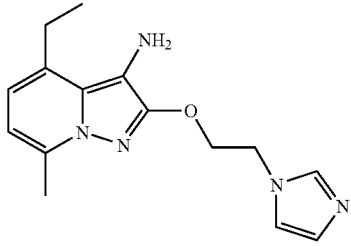

4-Ethyl-2-(2-imidazol-1-ylethoxy)-7-methylpyrazolo[1,5-a]pyridin-3-ylamine

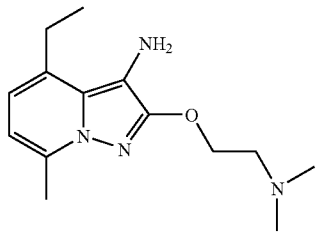

2-(2-Dimethylaminoethoxy)-4-ethyl-7-methylpyrazolo[1,5-a]pyridin-3-ylamine

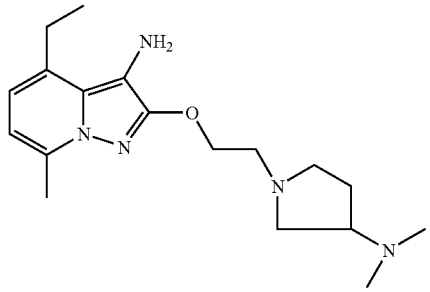

2-[2-(3-Dimethylaminopyrrolidin-1-yl)ethoxy]-4-ethyl-7-methylpyrazolo[1,5-a]pyridin-3-ylamine

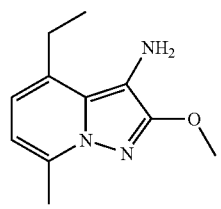

4-Ethyl-2-methoxy-7-methylpyrazolo[1,5-a]pyridin-3-ylamine

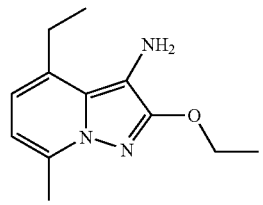

2-Ethoxy-4-ethyl-7-methylpyrazolo[1,5-a]pyridin-3-ylamine

-continued

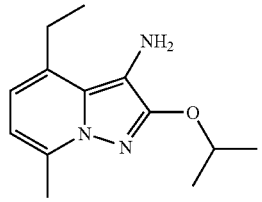

4-Ethyl-2-isopropoxy-7-methylpyrazolo[1,5-a]pyridin-3-ylamine

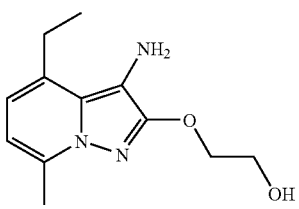

2-(3-Amino-4-ethyl-7-methylpyrazolo[1,5-a]pyridin-2-yloxy)ethanol

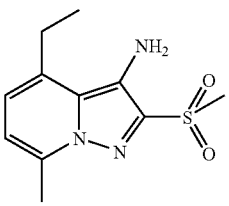

4-Ethyl-2-methanesulphonyl-7-methylpyrazolo[1,5-a]pyridin-3-ylamine

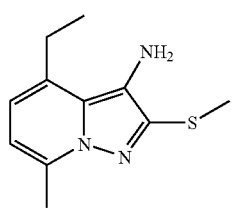

4-Ethyl-2-methylsulphanylpyrazolo[1,5-a]pyridin-3-ylamine

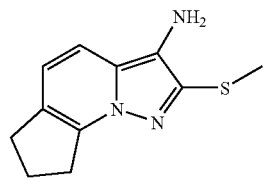

2-(methylsulphanyl)-7,8-dihydro-6H-cyclopenta[e]pyrazolo[1,5-a]pyridin-3-amine

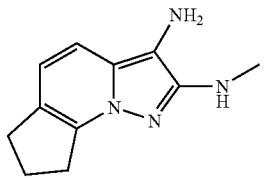

N-2-methyl-7,8-dihydro-6H-cyclopenta[e]pyrazolo[1,5-a]pyridine-2,3-diamine

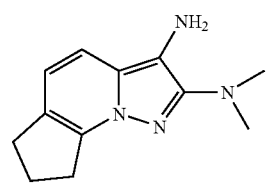

N-2,N-2-dimethyl-7,8-dihydro-6H-cyclopenta[e]pyrazolo[1,5-a]pyridine-2,3-diamine -continued

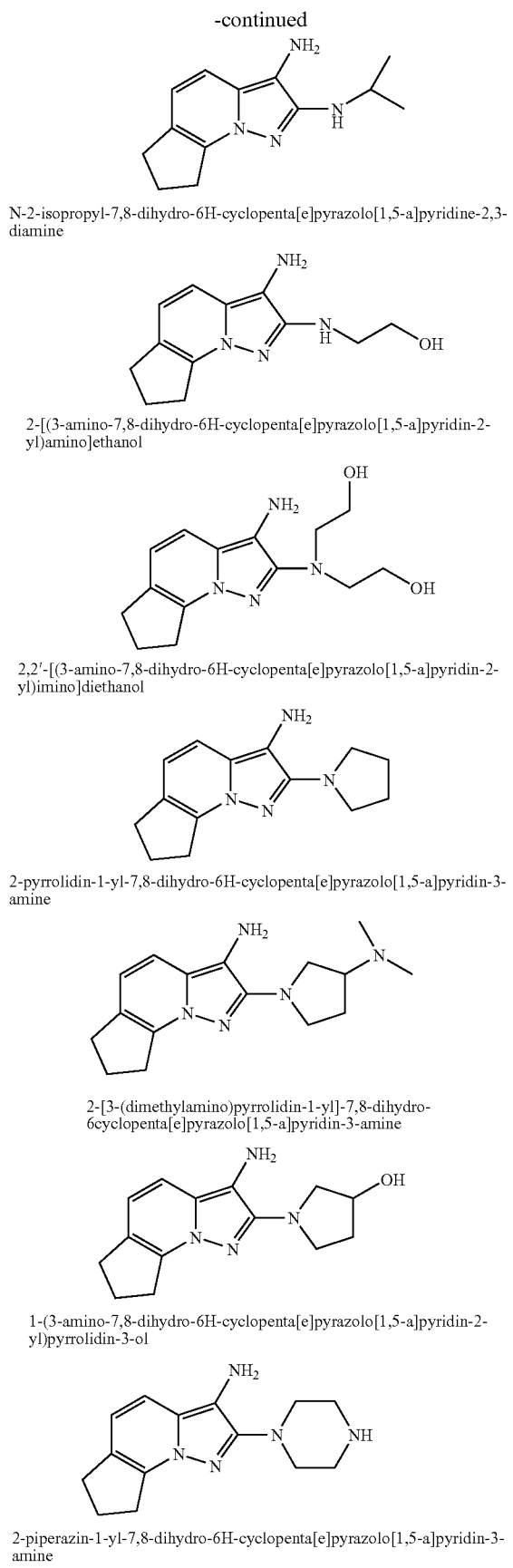

N-2-isopropyl-7,8-dihydro-6H-cyclopenta[e]pyrazolo[1,5-a]pyridine-2,3-diamine

2-[(3-amino-7,8-dihydro-6H-cyclopenta[e]pyrazolo[1,5-a]pyridin-2-yl)amino]ethanol 2,2′-[(3-amino-7,8-dihydro-6H-cyclopenta[e]pyrazolo[1,5-a]pyridin-2-yl)imino]diethanol 2-pyrrolidin-1-yl-7,8-dihydro-6H-cyclopenta[e]pyrazolo[1,5-a]pyridin-3-amine 2-[3-(dimethylamino)pyrrolidin-1-yl]-7,8-dihydro-6cyclopenta[e]pyrazolo[1,5-a]pyridin-3-amine 1-(3-amino-7,8-dihydro-6H-cyclopenta[e]pyrazolo[1,5-a]pyridin-2-yl)pyrrolidin-3-ol 2-piperazin-1-yl-7,8-dihydro-6H-cyclopenta[e]pyrazolo[1,5-a]pyridin-3-amine -continued

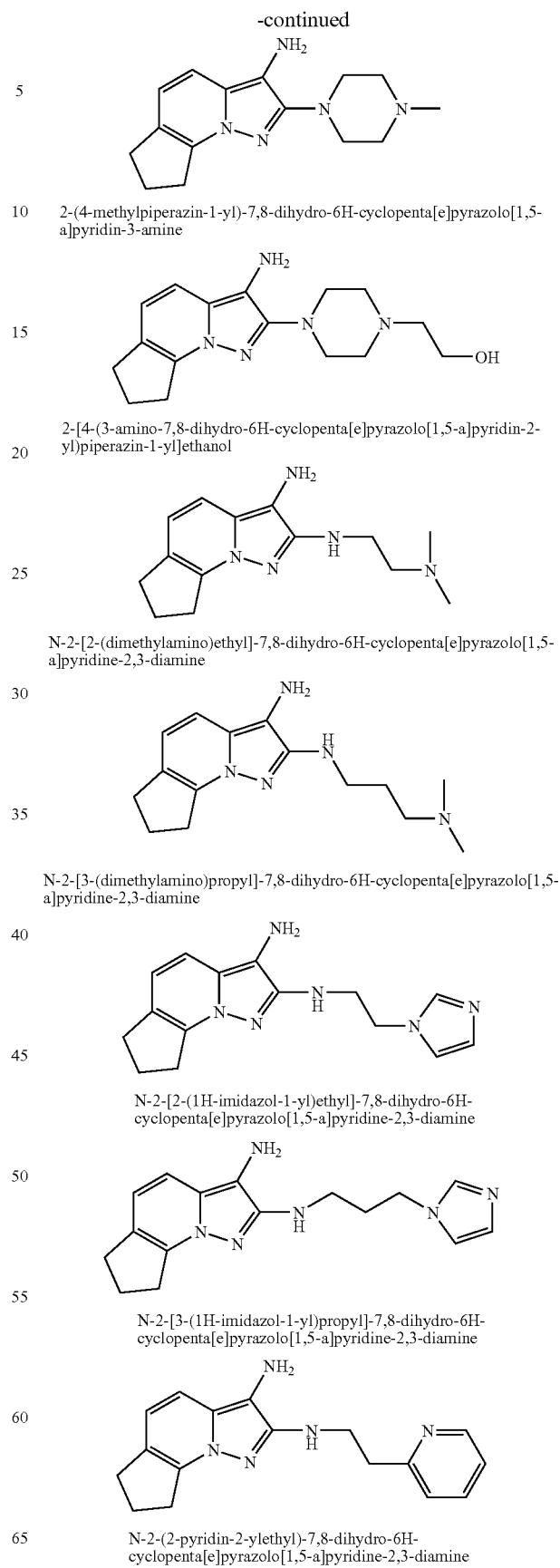

2-(4-methylpiperazin-1-yl)-7,8-dihydro-6H-cyclopenta[e]pyrazolo[1,5-a]pyridin-3-amine 2-[4-(3-amino-7,8-dihydro-6H-cyclopenta[e]pyrazolo[1,5-a]pyridin-2-yl)piperazin-1-yl]ethanol N-2-[2-(dimethylamino)ethyl]-7,8-dihydro-6H-cyclopenta[e]pyrazolo[1,5-a]pyridine-2,3-diamine N-2-[3-(dimethylamino)propyl]-7,8-dihydro-6H-cyclopenta[e]pyrazolo[1,5-a]pyridine-2,3-diamine N-2-[2-(1H-imidazol-1-yl)ethyl]-7,8-dihydro-6H-cyclopenta[e]pyrazolo[1,5-a]pyridine-2,3-diamine N-2-[3-(1H-imidazol-1-yl)propyl]-7,8-dihydro-6H-cyclopenta[e]pyrazolo[1,5-a]pyridine-2,3-diamine N-2-(2-pyridin-2-ylethyl)-7,8-dihydro-6H-cyclopenta[e]pyrazolo[1,5-a]pyridine-2,3-diamine -continued

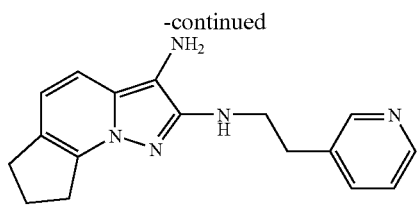

N-2-(2-pyridin-3-ylethyl)-7,8-dihydro-6H-
cyclopenta[e]pyrazolo[1,5-a]pyridine-2,3-diamine

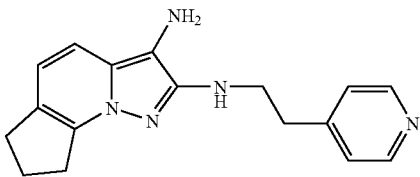

N-2-(2-pyridin-4-ylethyl)-7,8-dihydro-6H-
cyclopenta[e]pyrazolo[1,5-a]pyridine-2,3-diamine

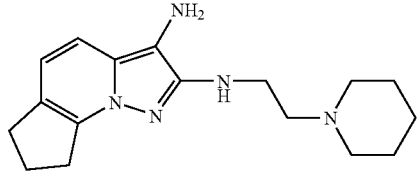

N-2-(2-piperidin-1-ylethyl)-7,8-dihydro-6H-
cyclopenta[e]pyrazolo[1,5-a]pyridine-2,3-diamine

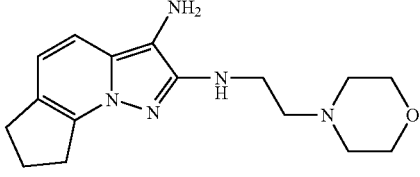

N-2-(2-morpholin-4-ylethyl)-7,8-dihydro-6H-
cyclopenta[e]pyrazolo[1,5-a]pyridine-2,3-diamine

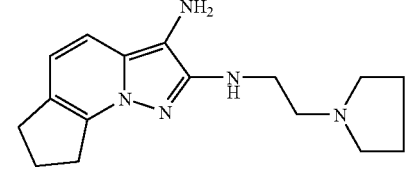

N-2-(2-pyrrolidin-1-ylethyl)-7,8-dihydro-6H-
cyclopenta[e]pyrazolo[1,5-a]pyridine-2,3-diamine

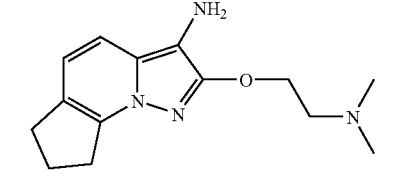

2-[2-(dimethylamino)ethoxy]-7,8-dihydro-6H-
cyclopenta[e]pyrazolo[1,5-a]pyridin-3-amine

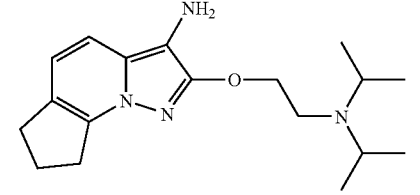

2-[2-(diisopropylamino)ethoxy]-7,8-dihydro-6H-
cyclopenta[e]pyrazolo[1,5-a]pyridin-3-amine -continued

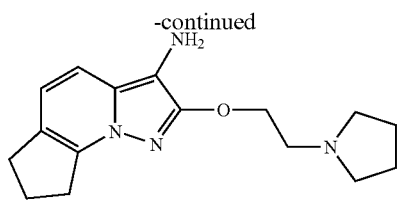

2-(2-pyrrolidin-1-ylethoxy)-7,8-dihydro-6H-
cyclopenta[e]pyrazolo[1,5-a]pyridin-3-amine

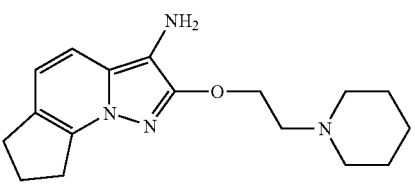

2-(2-piperidin-1-ylethoxy)-7,8-dihydro-6H-
cyclopenta[e]pyrazolo[1,5-a]pyridin-3-amine

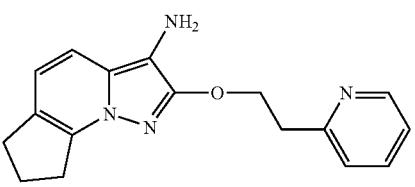

2-(2-pyridin-2-ylethoxy)-7,8-dihydro-6H-
cyclopenta[e]pyrazolo[1,5-a]pyridin-3-amine

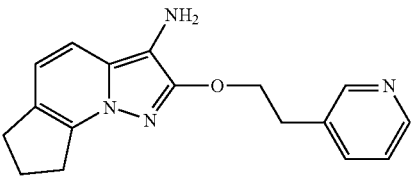

2-(2-pyridin-3-ylethoxy)-7,8-dihydro-6H-
cyclopenta[e]pyrazolo[1,5-a]pyridin-3-amine

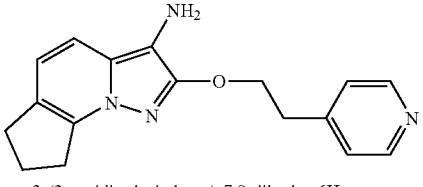

2-(2-pyridin-4-ylethoxy)-7,8-dihydro-6H-
cyclopenta[e]pyrazolo[1,5-a]pyridin-3-amine

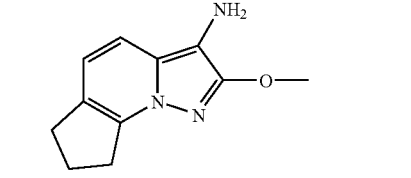

2-methoxy-7,8-dihydro-6H-cyclopenta[e]pyrazolo[1,5-a]pyridin-3-amine

2-ethoxy-7,8-dihydro-6H-cyclopenta[e]pyrazolo[1,5-a]pyridin-3-amine

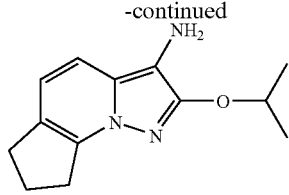

2-isopropoxy-7,8-dihydro-6H-cyclopenta[e]pyrazolo[1,5-a]pyridin-3-amine

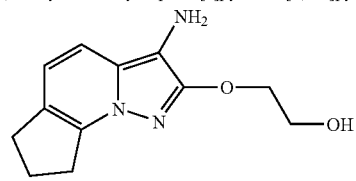

2-[(3-amino-7,8-dihydro-6H-cyclopenta[e]pyrazolo[1,5-a]pyridin-2-yl)oxy]ethanol

According to at least one embodiment of the present disclosure, the oxidation base of formula (I) above is such that $Z_1$ is chosen from an oxygen atom, a radical $NR_6$ and a radical $NR_6$ forming a heterocycle with $R_1$.

According to at least one embodiment, the radical $R_1$ can be chosen from an alkyl radical, an alkyl radical substituted with a hydroxy, an alkyl radical substituted with an amino or (di)alkylamino, an alkyl radical substituted with a nitrogen-containing heterocycle, for example piperazinyl, imidazolyl, pyrrolidinyl, pyridinyl, morpholinyl, and piperidinyl. According to one embodiment, the alkyl radical has from 1 to 6 carbon atoms.

Radical $R_6$ can be chosen from a hydrogen atom, an alkyl radical or an alkyl radical-substituted with a hydroxy radical, an amino radical, an alkylamino radical, a dialkyl amino radical, an alkyl radical substituted with a nitrogen-containing heterocycle, for example piperazinyl, imidazolyl, pyrrolidinyl, pyridinyl, morpholinyl, and piperidinyl. According to one embodiment, $R_6$ has from 1 to 6 carbon atoms.

According to at least one embodiment in which $R_1$ and $R_6$ together form a heterocycle with the nitrogen atom to which they are attached, the heterocycle can then be chosen from imidazoles, piperazines, pyrrolidines, and diazapanes, and these heterocycles can be substituted or unsubstituted.

When $R_2$, $R_3$, $R_4$ and $R_5$ represent a substituted alkyl radical, this alkyl radical can then be substituted, in at least one embodiment, by radical chosen from —OH, —OR$_9$, —NH$_2$, —NHR$_{10}$, —NR$_{11}$R$_{12}$ and SR$_9$ in which R$_9$, R$_{10}$, R$_{11}$ and R$_{12}$, which may be identical or different, are as defined previously.

Mention may be made, as examples, of methyl, ethyl, hydroxyethyl, aminoethyl, propyl and butyl radicals. According to at least one embodiment, $R_2$, $R_3$, $R_4$ and $R_5$ are chosen from, independently, a hydrogen atom and $C_1$-$C_4$ alkyl radicals such as methyl, ethyl, propyl, isopropyl, butyl, tert-butyl, or $R_4$ and $R_5$ together form a (hetero)cycle with 5 to 8 ring members. According to one embodiment, $R_4$ and $R_5$ together form a saturated or unsaturated ring with 5 or 8 ring members, such as from 5 to 6 ring members, for example a cyclopentane or cyclohexane, optionally substituted.

The following compounds may be mentioned as useful herein:

N-2-ethylpyrazolo[1,5-a]pyridine-2,3-diamine dihydrochloride,
2-(3-aminopyrazolo[1,5-a]pyridin-2-ylamino)ethanol dihydrochloride,
1-(3-aminopyrazolo[1,5-a]pyridin-2-ylamino)propan-2-ol dihydrochloride,
N-2-(3-imidazol-1-ylpropyl)pyrazolo[1,5-a]pyridine-2,3-diamine dihydrochloride,
2-pyrrolidin-1-ylpyrazolo[1,5-a]pyridin-3-ylamine dihydrochloride,
2-(3-dimethylaminopyrrolidin-1-yl)pyrazolo[1,5-a]pyridin-3-ylamine dihydrochloride,
2-imidazol-1-ylpyrazolo[1,5-a]pyridin-3-ylamine dihydrochloride,
N-2-(2-pyrrolidin-1-ylethyl)pyrazolo[1,5-a]pyridine-2,3-diamine dihydrochloride,
2-(3-aminopyrazolo[1,5-a]pyridin-2-yloxy)ethanol dihydrochloride,
2-ethoxypyrazolo[1,5-a]pyridin-3-ylamine dihydrochloride,
2-methoxy-7-methylpyrazolo[1,5-a]pyridin-3-ylamine hydrochloride,
4-ethyl-2-methoxy-7-methylpyrazolo[1,5-a]pyridin-3-ylamine dihydrochloride,
4-ethyl-7-methyl-2-pyrrolidin-1-ylpyrazolo[1,5-a]pyridin-3-ylamine dihydrochloride,
N-2-(2-piperidin-1-ylethyl)pyrazolo[1,5-a]pyridine-2,3-diamine dihydrochloride,
N-2-2-(diisopropylamino)ethyl]pyrazolo[1,5-a]pyridine-2,3-diamine dihydrochloride,
N-2-[2-(diethylamino)ethyl]pyrazolo[1,5-a]pyridine-2,3-diamine dihydrochloride,
N-2-(2-pyridin-3-ylethyl)pyrazolo[1,5-a]pyridine-2,3-diamine dihydrochloride,
N-2-(2-pyridin-4-ylethyl)pyrazolo[1,5-a]pyridine-2,3-diamine dihydrochloride,
N-2-(2-pyridin-2-ylethyl)pyrazolo[1,5-a]pyridine-2,3-diamine dihydrochloride,
N-2-(2-piperazin-1-ylethyl)pyrazolo[1,5-a]pyridine-2,3-diamine dihydrochloride,
N-2-[2-(4-methylpiperazin-1-yl)ethyl]pyrazolo[1,5-a]pyridine-2,3-diamine dihydrochloride,
N-2-(2-morpholin-4-ylethyl)pyrazolo[1,5-a]pyridine-2,3-diamine dihydrochloride,
N-2-[2-(dimethylamino)ethyl]-7,8-dihydro-6H-cyclopenta[e]pyrazolo[1,5-a]pyridine-2,3-diamine dihydrochloride,
2-[(3-amino-7,8-dihydro-6H-cyclopenta[e]pyrazolo[1,5-a]pyridin-2-yl)amino]ethanol hydrochloride,
2-methoxy-7,8-dihydro-6H-cyclopenta[e]pyrazolo[1,5-a]pyridin-3-amine hydrochloride,
2-isopropoxy-7,8-dihydro-6H-cyclopenta[e]pyrazolo[1,5-a]pyridin-3-amine hydrochloride,
2-[2-(dimethylamino)ethoxy]pyrazolo[1,5-a]pyridin-3-amine dihydrochloride,
2-(2-pyrrolidin-1-ylethoxy)pyrazolo[1,5-a]pyridin-3-amine dihydrochloride,
2-(2-piperidin-1-ylethoxy)pyrazolo[1,5-a]pyridin-3-amine dihydrochloride,
2-(2-morpholin-4-ylethoxy)pyrazolo[1,5-a]pyridin-3-amine dihydrochloride,
2-[2-(diisopropylamino)ethoxy]pyrazolo[1,5-a]pyridin-3-amine dihydrochloride,
2-(2-pyridin-2-ylethoxy)pyrazolo[1,5-a]pyridin-3-amine dihydrochloride,
2-(2-pyridin-3-ylethoxy)pyrazolo[1,5-a]pyridin-3-amine dihydrochloride,
2-(2-pyridin-4-ylethoxy)pyrazolo[1,5-a]pyridin-3-amine dihydrochloride,
N-5,N-5-dimethyl-2-methylsulphanylpyrazolo[1,5-a]pyridine-3,5-diamine dihydrochloride.

The at least one oxidation base is present (for each base) in an amount ranging from 0.001 to 10 wt. % of the total weight of the dyeing composition, such as from 0.005 to 6%.

The dyeing composition of the present disclosure may comprise at least one coupler conventionally used for the dyeing of keratin fibers. Among these couplers, mention may be made, for example, of meta-phenylenediamines, meta-aminophenols, meta-diphenols, naphthalenic couplers, heterocyclic couplers and their addition salts.

The following examples may be mentioned: 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis-2,4-diaminophenoxy)propane, 3-ureido-aniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl indole, 2-amino-3-hydroxypyridine, 6-hydroxybenzomorpholine, 3,5-diamino-2,6-dimethoxypyridine, 1-N-(β-hydroxyethyl)amino-3,4-methylene dioxybenzene, 2,6-bis-(β-hydroxyethylamino)toluene and their acid-addition salts.

In the composition of the present disclosure, the at least one coupler is present (for each coupler) in an amount ranging from 0.001 to 10 wt. % of the total weight of the dyeing composition, such as from 0.005 to 6%.

The composition of the present disclosure can, in addition, comprise at least one additional oxidation base conventionally used in oxidation dyeing other than those described previously. For example, these additional oxidation bases may be chosen from para-phenylenediamines, bis-phenylalkylenediamines, para-aminophenols, bis-para-aminophenols, ortho-aminophenols, ortho-phenylenediamines, heterocyclic bases different from the derivatives of formula (I) as defined previously and their addition salts.

Among the para-phenylenediamines, the following may be mentioned as examples: para-phenylenediamine, para-toluylenediamine, 2-chloro-para-phenylenediamine, 2,3-dimethyl para-phenylenediamine, 2,6-dimethyl para-phenylenediamine, 2,6-diethyl para-phenylenediamine, 2,5-dimethyl para-phenylenediamine, N,N-dimethyl para-phenylenediamine, N,N-diethyl para-phenylenediamine, N,N-dipropyl para-phenylenediamine, 4-amino N,N-diethyl 3-methylaniline, N,N-bis-(β-hydroxyethyl) para-phenylenediamine, 4-N,N-bis-(β-hydroxyethyl)amino 2-methylaniline, 4-N,N-bis-(β-hydroxyethyl)amino 2-chloro aniline, 2-β-hydroxyethyl para-phenylenediamine, 2-fluoro para-phenylenediamine, 2-isopropyl para-phenylenediamine, N-(β-hydroxypropyl) para-phenylenediamine, 2-hydroxymethyl para-phenylenediamine, N,N-dimethyl 3-methyl para-phenylenediamine, N,N-(ethyl, β-hydroxyethyl) para-phenylenediamine, N-(β,γ-dihydroxypropyl) para-phenylenediamine, N-(4'-aminophenyl) para-phenylenediamine, N-phenyl para-phenylenediamine, 2-β-hydroxyethyloxy para-phenylenediamine, 2-β-acetylaminoethyloxy para-phenylenediamine, N-(β-methoxyethyl) para-phenylenediamine 4-aminophenylpyrrolidine, 2-thienyl para-phenylenediamine, 2-β hydroxyethylamino-5-amino toluene, 3-hydroxy 1-(4'-aminophenyl)pyrrolidine and their acid-addition salts.

Among the para-phenylenediamines mentioned above, further mention may be made of: para-phenylenediamine, para-toluylenediamine, 2-isopropyl para-phenylenediamine, 2-β-hydroxyethyl para-phenylenediamine, 2-β-hydroxyethyloxy para-phenylenediamine, 2,6-dimethyl para-phenylenediamine, 2,6-diethyl para-phenylenediamine, 2,3-dimethyl para-phenylenediamine, N,N-bis-(β-hydroxyethyl) para-phenylenediamine, 2-chloro para-phenylenediamine, 2-β-acetylaminoethyloxy para-phenylenediamine, and their acid-addition salts.

The following may be mentioned as examples of the bis-phenylalkylenediamines: N,N'-bis-(β-hydroxyethyl) N,N'-bis-(4'-aminophenyl) 1,3-diaminopropanol, N,N'-bis-(β-hydroxyethyl) N,N'-bis-(4'-aminophenyl) ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino 3'-methylphenyl) ethylenediamine, 1,8-bis-(2,5-diaminophenoxy)-3,6-dioxaoctane, and their acid-addition salts.

The following may be mentioned as examples of the para-aminophenols: para-aminophenol, 4-amino 3-methylphenol, 4-amino 3-fluorophenol, 4-amino 3-hydroxymethylphenol, 4-amino 2-methylphenol, 4-amino 2-hydroxymethylphenol, 4-amino 2-methoxymethylphenol, 4-amino 2-aminomethylphenol, 4-amino 2-(β-hydroxyethyl aminomethyl)phenol, 4-amino 2-fluorophenol, and their acid-addition salts.

The following may be mentioned as examples of the ortho-aminophenols: 2-aminophenol, 2-amino 5-methylphenol, 2-amino 6-methylphenol, 5-acetamido 2-aminophenol, and their acid-addition salts.

The following may be mentioned as examples of the heterocyclic bases: pyridine derivatives, pyrimidine derivatives and pyrazole derivatives.

Among the pyridine derivatives, the following compounds may be mentioned: the compounds described, for example, in British Patents GB 1 026 978 and GB 1 153 196, as well as 2,5-diaminopyridine, 2-(4-methoxyphenyl)amino 3-aminopyridine, 2,3-diamino-6-methoxypyridine, 2-(β-methoxyethyl)amino 3-amino-6-methoxypyridine, 3,4-diaminopyridine, and their acid-addition salts.

Other pyridine oxidation bases that can be used herein are the 3-amino-pyrazolo-[1,5-a]-pyridine oxidation bases or their addition salts described, for example, French Patent Application FR 2 801 308. The following may be mentioned as examples: pyrazolo[1,5-a]pyridin-3-ylamine; 2-acetylamino pyrazolo[1,5-a]pyridin-3-ylamine; 2morpholin-4-yl-pyrazolo[1,5-a]pyridin-3-ylamine; 3-amino-pyrazolo[1,5-a]pyridin-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; 3-amino-pyrazolo[1,5-a]pyridin-7-ol; as well as their addition salts with an acid or with a base.

Among the pyrimidine derivatives, mention may be made of the compounds described, for example, in patents DE 23 59 399; JP 88-169571; JP 05-163124; EP 0 770 375 or published patent application WO 96/15765 such as 2,4,5,6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, 2,5,6-triaminopyrimidine, and the pyrazolo-pyrimidine derivatives such as those mentioned in French Patent Application FR-A-2 750 048 and among which we may mention pyrazolo-[1,5-a]-pyrimidine-3,7-diamine, 2,5-dimethyl pyrazolo-[1,5-a]-pyrimidine-3,7-diamine; pyrazolo-[1,5-a]-pyrimidine-3,5-diamine; 2,7-dimethyl pyrazolo-[1,5-a]-pyrimidine-3,5-diamine; 3-amino pyrazolo-[1,5-a]-pyrimidin-7-ol; 3-amino pyrazolo-[1,5-a]-pyrimidin-5-ol; 2-(3-amino pyrazole-[1,5-a]-pyrimidin-7-ylamino)-ethanol, 2-(7-amino pyrazolo-[1,5-a]-pyrimidin-3-ylamino)-ethanol, 2-[(3-amino-pyrazolo-[1,5-a]-pyrimidin-7-yl)-(2-hydroxy-ethyl)-amino]-ethanol, 2-[(7-amino-pyrazolo-[1,5-a]-pyrimidin-3-yl)-(2-hydroxy-ethyl)-amino]-ethanol, 5,6-dimethyl pyrazolo-[1,5-a]-pyrimidine-3,7-diamine, 2,6-dimethyl pyrazolo-[1,5-a]-pyrimidine-3,7-diamine, 2,5, N 7, N 7-tetramethyl pyrazolo-[1,5-a]-pyrimidine-3,7-diamine, 3-amino-5-methyl-7-imidazolylpropylamino pyrazolo-[1,5-a]-pyrimidine and their acid-addition salts and their tautomeric forms, when a tautomeric equilibrium exists.

Among the pyrazole derivatives, mention may be made of the compounds described in patents DE 38 43 892, DE 41 33 957 and patent applications WO 94/08969, WO 94/08970, FR-A-2 733 749 and DE 195 43 98,8 such as 4,5-diamino 1-methyl pyrazole, 4,5-diamino 1-(β-hydroxyethyl) pyrazole, 3,4-diamino pyrazole, 4,5-diamino 1-(4'-chlorobenzyl) pyrazole, 4,5-diamino 1,3-dimethyl pyrazole, 4,5-diamino 3-methyl 1-phenyl pyrazole, 4,5-diamino 1-methyl 3-phenyl pyrazole, 4-amino 1,3-dimethyl 5-hydrazino pyrazole, 1-benzyl 4,5-diamino 3-methyl pyrazole, 4,5-diamino 3-tert-butyl 1-methyl pyrazole, 4,5-diamino 1-tert-butyl 3-methyl pyrazole, 4,5-diamino 1-(β-hydroxyethyl) 3-methyl pyrazole, 4,5-diamino 1-ethyl 3-methyl pyrazole, 4,5-diamino 1-ethyl 3-(4'-methoxyphenyl) pyrazole, 4,5-diamino 1-ethyl 3-hydroxymethyl pyrazole, 4,5-diamino 3-hydroxymethyl 1-methyl pyrazole, 4,5-diamino 3-hydroxymethyl 1-isopropyl pyrazole, 4,5-diamino 3-methyl 1-isopropyl pyrazole, 4-amino 5-(2'-aminoethyl)amino 1,3-dimethyl pyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl)amino 1-methyl pyrazole, and their acid-addition salts.

The at least one additional oxidation base other than those of formula (I) present in the composition of the disclosure is present (for each) in an amount ranging from 0.001 to 10 wt. % of the total weight of the dyeing composition, such as from 0.005 to 6%.

In at least one embodiment, the addition salts of these additional oxidation bases and of the couplers that can be used within the scope of the present disclosure may be chosen from acid-addition salts such as the hydrochlorides, hydrobromides, sulphates, citrates, succinates, tartrates, lactates, tosylates, benzenesulphonates, phosphates and acetates and base-addition salts such as sodium hydroxide, potassium hydroxide, ammonia, amines or alkanolamines.

The dyeing composition according to the present disclosure can additionally comprise at least one direct dye which can, in at least one embodiment, be chosen from the nitro dyes of the benzene series, the azo direct dyes and the methine direct dyes. These direct dyes can be of a non-ionic, anionic or cationic nature.

As defined herein, the suitable medium for dyeing, also called the dyeing support, is a cosmetic medium comprising water or a mixture of water and at least one organic solvent for dissolving the compounds that would not be sufficiently soluble in water. Examples of such organic solvents include, for example, the $C_1$-$C_4$ lower alkanols, such as ethanol and isopropanol; polyols and polyol ethers such as 2-butoxyethanol, propylene glycol, monomethyl ether of propylene glycol, the monoethyl ether and monomethyl ether of diethylene glycol, as well as the aromatic alcohols such as benzyl alcohol or phenoxyethanol, and mixtures thereof.

In at least one embodiment, the solvents are present in an amount ranging from 1 to 40 wt. % relative to the total weight of the dyeing composition, such as from 5 to 30 wt. %.

The dyeing composition according to the present disclosure may also comprise at least one additive conventionally used in compositions for dyeing the hair, such as anionic, cationic, non-ionic, amphoteric, zwitterionic surfactants or mixtures thereof, anionic, cationic, non-ionic, amphoteric, zwitterionic polymers or mixtures thereof, inorganic or organic thickeners, such as anionic, cationic, non-ionic and amphoteric associative polymeric thickeners, antioxidants, penetrants, sequestering agents, perfumes, buffers, dispersants, conditioning agents such as volatile or non-volatile, modified or unmodified silicones, film-forming agents, ceramides, preservatives, and opacifiers.

When present, the at least one additive is present, in an amount for each of them, ranging from 0.01 to 20 wt. % relative to the weight of the dyeing composition.

A person skilled in the art will of course make sure that any additional compound or compounds are chosen in such a way that the advantageous properties intrinsic to the oxidation dyeing composition according to the present disclosure are not, or substantially not, affected adversely by the addition or additions envisaged.

The pH of the presently disclosed dyeing composition ranges from 3 to 12, such as from 5 to 11. It can be adjusted to the desired value by means of acidifying or alkalizing agents usually employed in the dyeing of keratin fibers or alternatively by means of conventional buffering systems.

Among the acidifying agents, the following may be mentioned as examples: mineral or organic acids such as hydrochloric acid, orthophosphoric acid, sulphuric acid, carboxylic acids such as acetic acid, tartaric acid, citric acid, lactic acid, and sulphonic acids.

Among the alkalizing agents, the following may be mentioned as examples: ammonia, alkali metal carbonates, alkanolamines such as the mono-, di- and tri-ethanolamines as well as their derivatives, the hydroxides of sodium or potassium and the compounds of the following formula (II):

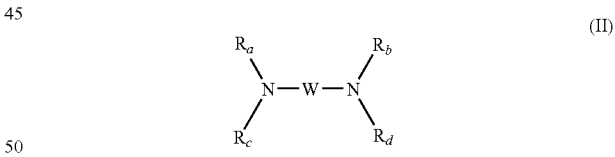

in which W is a propylene residue optionally substituted with a hydroxyl group or a $C_1$-$C_4$ alkyl radical; $R_a$, $R_b$, $R_c$ and $R_d$, which may be identical or different, are each chosen from a hydrogen atom, $C_1$-$C_4$ alkyl radicals and $C_1$-$C_4$ hydroxyalkyl radicals.

The dyeing composition according to the present disclosure can be in various forms, such as in the form of liquids, creams, gels, or in any other form that is suitable for carrying out dyeing of keratin fibers, such as human hair.

The method of the present disclosure is a method in which the composition according to the present disclosure as defined previously is applied to the fibers, and the color is developed by means of an oxidizing agent. The color can be developed at acid, neutral or alkaline pH and the oxidizing agent can be added to the composition right at the moment of use or it can be used on the basis of an oxidizing composition containing it, applied simultaneously with or sequentially to the composition of the disclosure.

According to at least one embodiment, the composition according to the present disclosure is mixed, for example at the moment of use, with a composition containing, in a medium suitable for dyeing, at least one oxidizing agent, said oxidizing agent being present in an amount sufficient for developing a coloration. The mixture obtained is then applied to the keratin fibers. After a waiting time of 3 to 50 minutes, such as from 5 to 30 minutes, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, per-salts such as perborates and persulphates, peracids and the oxidase enzymes, such as peroxidases, 2-electron oxidoreductases such as uricases and 4-electron oxygenases such as laccases. In one embodiment, hydrogen peroxide is used.

The oxidizing composition can also comprise at least one additive used conventionally in compositions for dyeing the hair and as defined previously.

The pH of the oxidizing composition containing the oxidizing agent is such that after mixing with the dyeing composition, the pH of the resultant composition applied to the keratin fibers ranges, in at least one embodiment, from 3 to 12, such as from 5 to 11. It can be adjusted to the desired value by means of acidifying or alkalizing agents usually employed in the dyeing of keratin fibers and as defined previously.

The present disclosure also relates to a dyeing "kit" with several compartments, in which a first compartment contains the dyeing composition of the present disclosure defined above and a second compartment contains an oxidizing composition. This kit can be equipped with a means for delivering the desired mixture onto the hair, such as the kits described in French Patent FR-2 586 913.

Using this kit, it is possible to dye keratin fibers by a method that comprises mixing a dyeing composition containing at least one oxidation base of formula (I) with an oxidizing agent, and applying the mixture obtained on the keratin fibers for a time that is sufficient to develop the desired coloration.

The present disclosure also relates to the use of a pyrazolopyridine derivative of formula (I) or of one of its addition salts as previously defined for the oxidation dyeing of keratin fibers, for example, of human keratin fibers such as the hair.

The compounds of formula (I) that can be used in the present disclosure can be obtained from intermediates and by synthetic routes described in the literature, such as in the following references: J. Het. Chem., 2001, 38(3), 613-616; Helvetica Chimica Acta, 1950, 33, 1183-1194; J. Org. Chem., 23, 2029 (1958); J. Am. Chem. Soc., 73, 3240 (1951); J. Am. Chem. Soc., 84, 590 (1962); Justus Liebig Ann. Chem., 686, 134 (1965); Tetrahedron Lett., 31, 2859-2862 (1973), U.S. Pat. Nos. 4,128,425 and 2,841,584 and the references cited therein.

According to at least one embodiment, the compounds of formula (I) can be synthesized according to the following scheme:

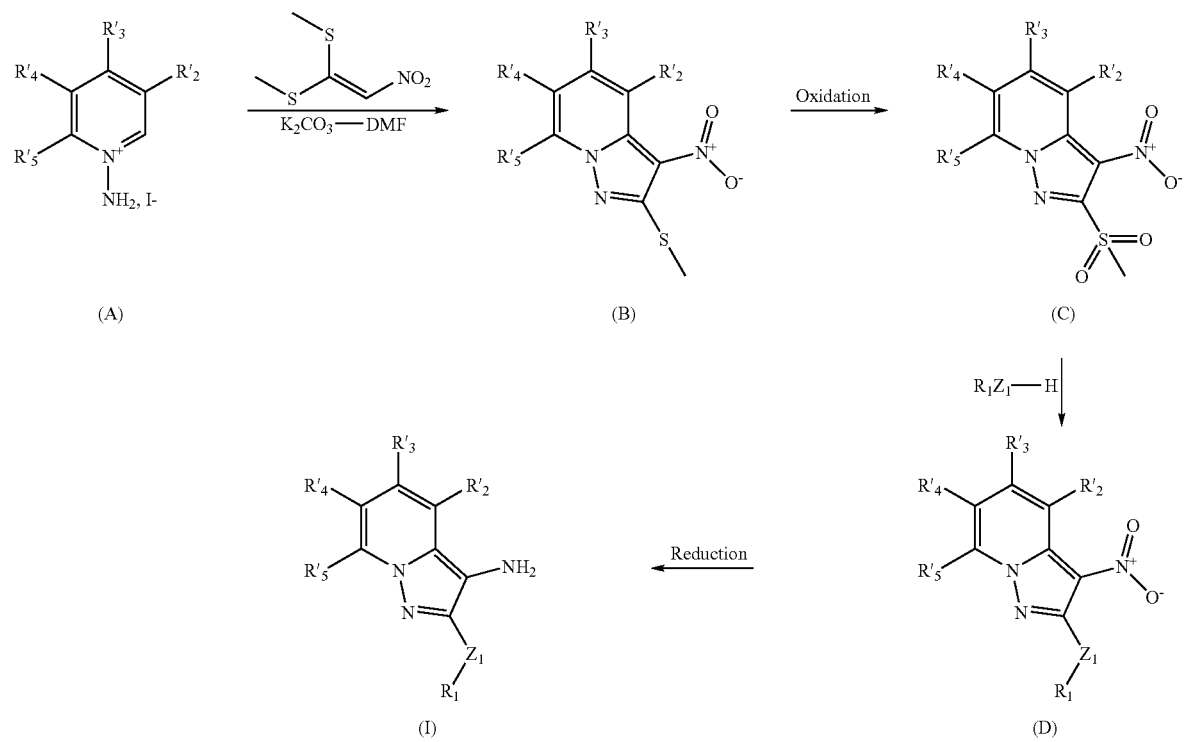

The ready-to-use composition which is finally applied to the keratin fibers can be in various forms, such as in the form of liquids, creams, gels or in any other form suitable for carrying out dyeing of keratin fibers, such as human hair.

in which $R'_2$, $R'_3$, $R'_4$ and $R'_5$ have the same meanings as $R_2$, $R_3$, $R_4$ and $R_5$ or are precursors thereof.

As an example, when $R_1$ is an alkyl radical $(C_1\text{-}C_{10})$—$NR_{11}R_{12}$ or an alkyl radical $(C_1\text{-}C_{10})$—$OR_{11}$, the following method of synthesis can be used:

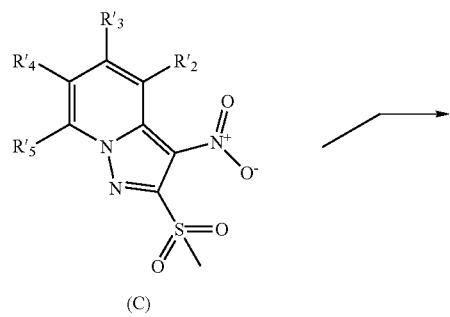

(C)

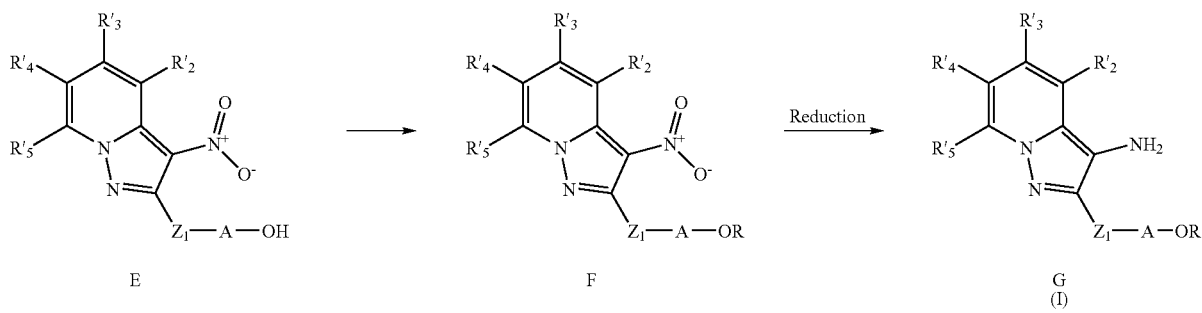

E            F            G (I)

$HZ_1$—A—OH    where A = linear or branched $C_1$–$C_{10}$ alkyl

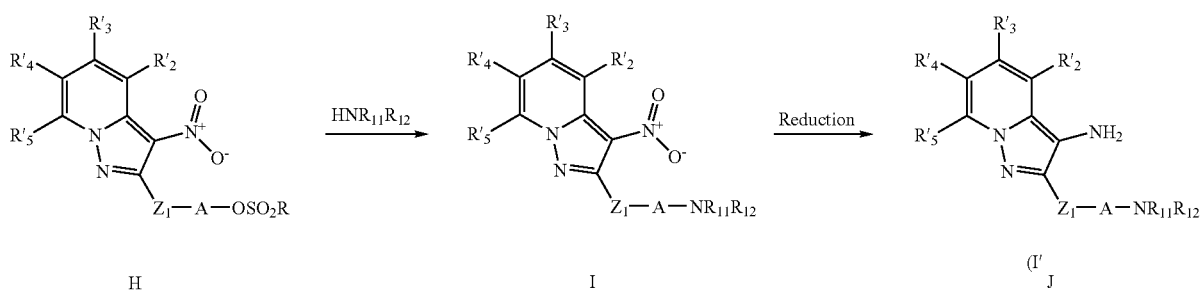

H            I            (I') J

Further details of these routes of synthesis are given in the examples described below.

The present disclosure also relates to the intermediates (A) and (B) as defined above in which at least one of the radicals $R'_2$, $R'_3$, $R'_4$ or $R'_5$ is different from a hydrogen atom apart from the compound for which $R'_2$=Me when all the other substituents are hydrogen.

The present disclosure also relates to intermediates of formula (C), (D), (F), (H), (I) as defined above.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below. In the text hereinbelow, "A.M." means Active Material.

EXAMPLES

Example 1

N-2-Ethyl pyrazolo[1,5-a]pyridine-2,3-diamine dihydrochloride

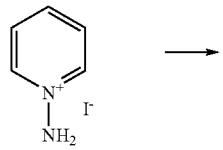

→

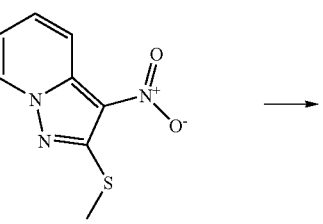

→

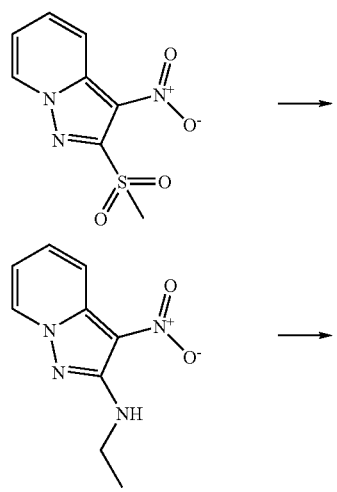

→

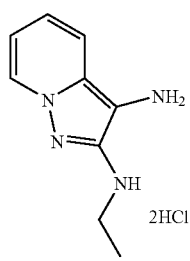

Synthesis of 2-methylsulphanyl-3-nitro-pyrazolo[1,5-a]pyridine

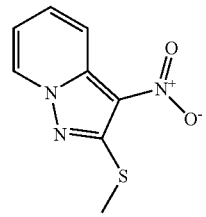

A solution of 111 g of 1-N-aminopyridinium iodide (0.5 mol) in DMF (500 ml) was prepared in a 2-liter three-necked flask equipped with a mechanical stirrer and an internal temperature sensor under a stream of nitrogen.

Potassium carbonate (207.3, 3 eq.) was then added in one go, followed by 1,1-bis(methylthio)-2-nitroethylene (165.2 g, 2 eq.), also in one go. The weight of the reaction mixture increased. Then 500 ml of DMF were added to make the reaction mixture more fluid.

After being stirred for 48 h at room temperature, the reaction mixture was poured into 4 liters of ice water. The precipitate that formed was filtered and washed with plenty of water (5 liters), then dried at 80° C. under vacuum.

The excess 1,1-bis(methylthio)-2-nitroethylene (30 mol. % determined by $^1$H-NMR) was removed from the solid thus obtained by re-pasting in ethyl acetate. After draining and drying, 72 g of a yellowish-beige solid, corresponding to the expected product, was obtained.

$^1$H-NMR (300 MHz, DMSO-d$_6$): 8.98 (1H, d); 8.20 (1H, d), 7.89 (1H, m), 7.36 (1H, m), 2.63 (3H, s).

Synthesis of 2-methanesulphonyl-3-nitro-pyrazolo[1,5-a]pyridine

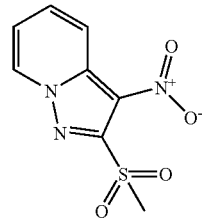

In succession, 880 g of Oxone (5 eq.), 2 liters of water and 60 g of 2-methylsulphonyl-3-nitro-pyrazolo[1,5-a]pyridine (0.287 eq.) obtained previously, were put in a 4-liter three-necked flask equipped with a mechanical stirrer and an internal temperature sensor. The whole was stirred at room temperature.

The reaction was completed by adding Oxone (120 g, 0.7 eq.), and after 4 h stirring at room temperature, the reaction was stopped.

The solid that formed was drained and washed with plenty of water until a filtrate was obtained that no longer contained peroxide. The filtrate was then placed under vacuum at 40° C. over P$_2$O$_5$.

59 g of the expected product was obtained in the form of a yellowish-beige powder.

¹H-NMR (300 MHz, DMSO-d₆): 9.15 (1H, d); 8.35 (1H, d), 8.03 (1H, m), 7.56 (1H, m), 3.59 (3H, s).

Synthesis of
ethyl-(3-nitro-pyrazolo[1,5-a]pyridin-2-yl)-amine

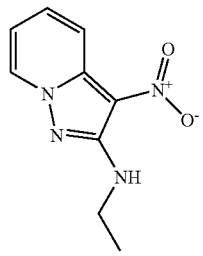

3 ml of N-methylpyrrolidinone, 2.41 g (0.01 mol) 2-methanesulphonyl-3-nitro-pyrazolo[1,5-a]pyridine and 4.015 g of ethylamine were put in a 10 ml three-necked flask equipped with a bulb condenser, a thermometer and a magnetic stirrer. While stirring, the mixture was heated to 70° C. on an oil bath, for 5 hours.

The yellow compound isolated by pouring the reaction mixture into water was drained on a frit and then washed with water several times. After drying under vacuum, in the presence of P₂O₅, 1.68 g of a yellow solid were recovered, corresponding to the expected compound.

NMR analyses (¹H 400 MHz and ¹³C 100.61 MHz DMSO d₆) were consistent with the expected structure. The mass of the expected compound C₉H₁₀N₄O₂ was detected in mass spectrometry. The quasi-molecular ions [M+H]⁺, [M+Na]⁺ and [M−H]⁻ of the expected molecule, C₉H₁₀N₄O₂, were mainly detected.

Synthesis of N-2-ethyl
pyrazolo[1,5-a]pyridine-2,3-diamine dihydrochloride

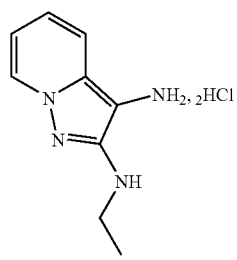

400 ml of ethanol and 11 g of zinc powder were put in a 500 ml three-necked flask equipped with a bulb condenser, a thermometer and a magnetic stirrer, and brought to reflux.

2.25 g of ammonium chloride dissolved in 0.5 ml of water were then added, and 3 g of ethyl-(3-nitro-pyrazolo[1,5-a]pyridin-2-yl)-amine was added in portions over a period of 15 minutes. Reflux was maintained for 2 hours.

When reduction ended, the zinc was removed by filtration under argon on a bed of Celite and the filtrate was collected in a flask containing 50 ml of previously cooled 6N hydrochloric isopropanol. The zinc was washed with ethanol, the filtrates were combined and evaporated to dryness.

After vacuum drying, in the presence of P₂O₅ and soda tablets, 2.1 g of a blue powder corresponding to the expected compound was obtained.

NMR analyses (¹H 400 MHz and ¹³C 100.61 MHz DMSO d₆) were consistent with the expected structure. The quasi-molecular ions [M+H]⁺ and [M+Na]⁺ of the expected molecule were detected: C₉H₁₂N₄.

Example 2

2-(3-Amino-pyrazolo[1,5-a]pyridin-2-ylamino)-ethanol dihydrochloride

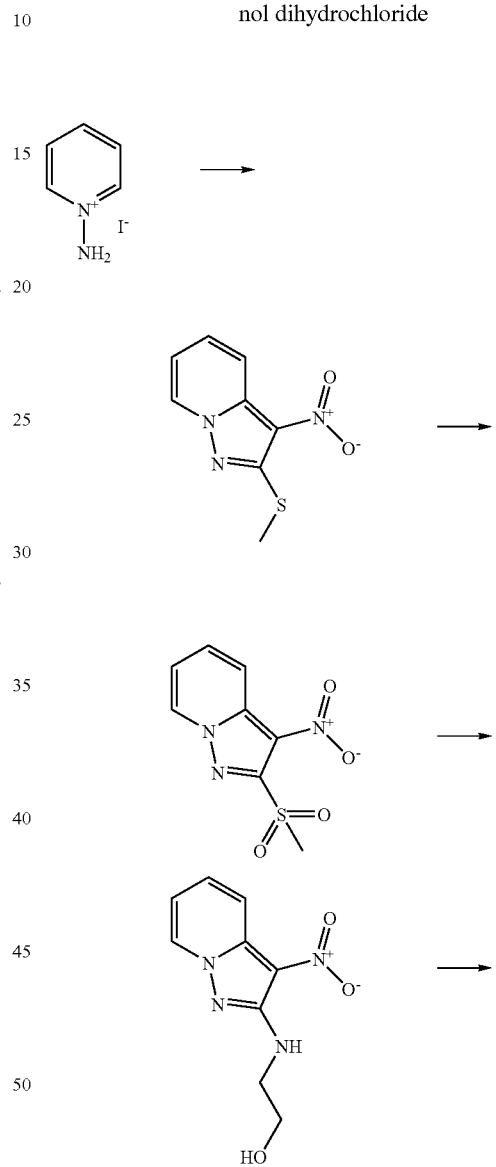

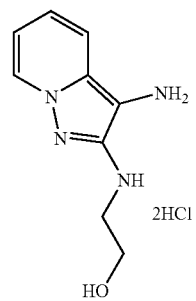

Synthesis of 2-[(3-nitro pyrazolo[1,5-a]pyridin-2-yl)amino]ethanol

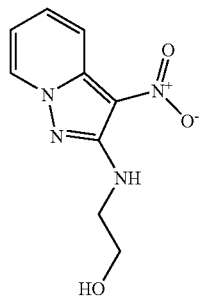

10 ml of N-methylpyrrolidinone, 7.25 g (0.03 mol) 2-methanesulphonyl-3-nitro-pyrazolo[1,5-a]pyridine and 6 ml ethanolamine were put in a 50 ml three-necked flask equipped with a bulb condenser, a thermometer and a magnetic stirrer. While being stirred, the mixture was heated to 70° C. on an oil bath for 5 hours.

The yellow compound, isolated by pouring the reaction mixture into water, was drained on a frit and then washed with water several times. After drying under vacuum, in the presence of $P_2O_5$, 6.45 g of yellow solid corresponding to the expected compound was recovered.

NMR analyses ($^1$H 400 MHz and $^{13}$C 100.61 MHz DMSO $d_6$) were consistent with the expected structure.

The quasi-molecular ions $[M+H]^+$, $[M+Na]^+$ and $[M-H]^-$ of the expected molecule, $C_9H_{10}N_4O_3$, were mainly detected.

Synthesis of 2-(3-amino-pyrazolo[1,5-a]pyridin-2-ylamino)-ethanol dihydrochloride

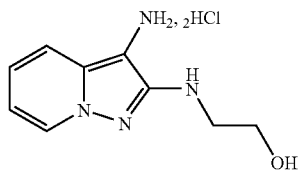

350 ml of ethanol and 5 g of zinc powder were put in a 500 ml three-necked flask equipped with a bulb condenser, a thermometer and a magnetic stirrer, and brought to reflux.

1 g of ammonium chloride dissolved in 0.5 ml water was then added, and 2 g of 2-[(3-nitro pyrazolo[1,5-a]pyridin-2-yl)amino]ethanol were added in portions over a period of 15 minutes. Reflux was maintained for 4 h.

At the end of reduction, the zinc was removed by filtration under argon on a bed of Celite and the filtrate collected in a flask containing 50 ml of previously cooled 6N hydrochloric isopropanol. The zinc was washed with ethanol, the filtrates were combined and evaporated to dryness.

After being dried under vacuum, in the presence of $P_2O_5$ and soda tablets, 1.23 g of a bluish powder corresponding to the expected compound was obtained.

NMR analyses ($^1$H 400 MHz and $^{13}$C 100.61 MHz DMSO $d_6$) were consistent with the expected structure.

The quasi-molecular ions $[M+H]^+$, $[M+Na]^+$ and $[M-H]^-$ of the expected molecule, $C_9H_{12}N_4O$, were mainly detected.

Example 3

1-(3-Amino-pyrazolo[1,5-a]pyridin-2-ylamino)-propan-2-ol

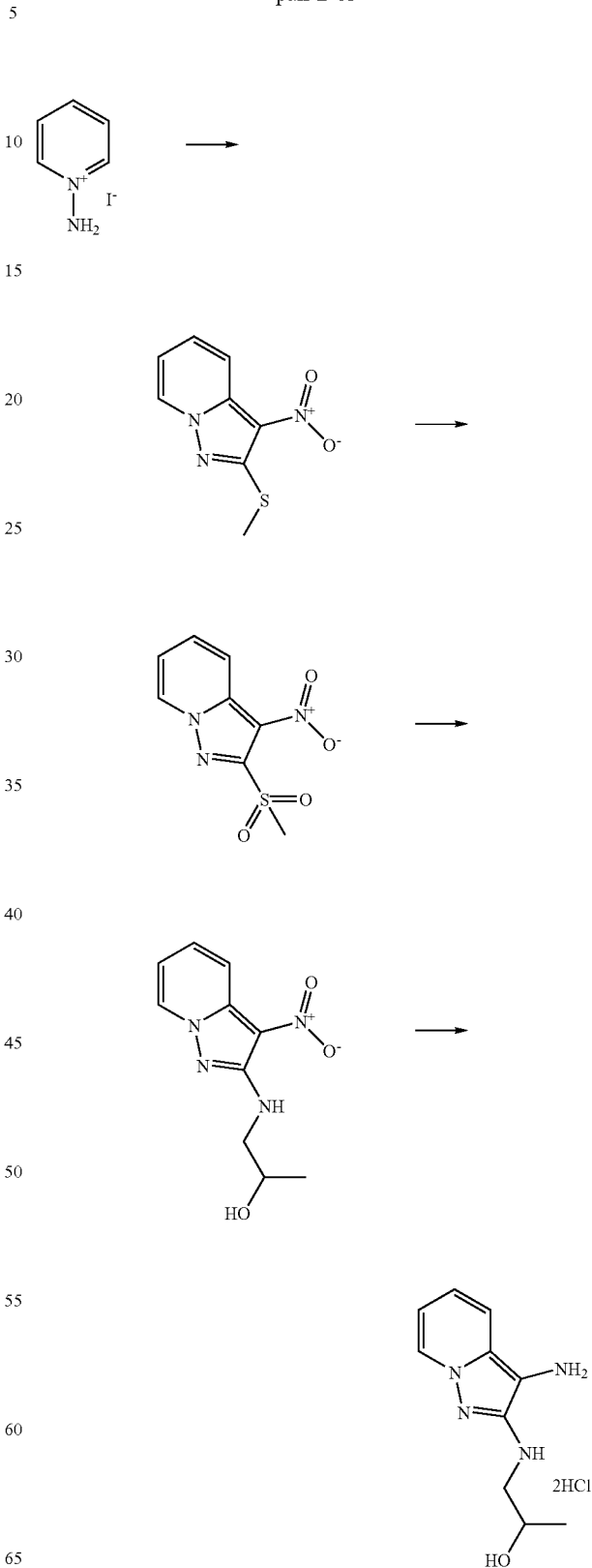

Synthesis of 1-[(3-nitro pyrazolo[1,5-a]pyridin-2-yl)amino]propan-2-ol

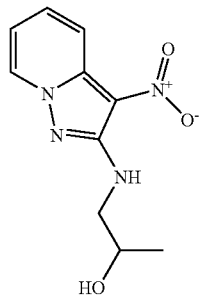

10 ml of N-methylpyrrolidinone, 7.23 g (0.03 mol) 2-methanesulphonyl-3-nitro-pyrazolo[1,5-a]pyridine and 7 ml of 1-amino-2-propanol were put in a 50 ml three-necked flask equipped with a bulb condenser, a thermometer and a magnetic stirrer. While being stirred, the mixture was heated to 70° C. on an oil bath, for 5 hours.

The yellow compound, isolated by pouring the reaction mixture into water, was drained on a frit and then washed with water several times. After drying under vacuum, in the presence of $P_2O_5$, 6.02 g of a yellow solid corresponding to the expected compound was recovered.

NMR analyses ($^1$H 400 MHz and $^{13}$C 100.61 MHz DMSO $d_6$) were consistent with the expected structure.

Synthesis of 1-(3-amino-pyrazolo[1,5-a]pyridin-2-ylamino)-propan-2-ol dihydrochloride

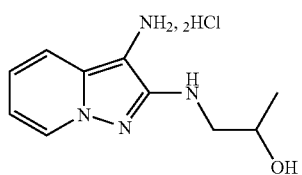

350 ml of ethanol and 5 g of zinc powder were put in a 500 ml three-necked flask equipped with a bulb condenser, a thermometer and a magnetic stirrer, and brought to reflux.

Then 1 g of ammonium chloride dissolved in 0.5 ml water was added, and 2 g of 1-[(3-nitropyrazolo[1,5-a]pyridin-2-yl)amino]propan-2-ol was added in portions over a period of 15 minutes. Reflux was maintained for 4 hours.

At the end of reduction, the zinc was removed by filtration under argon on a bed of Celite and the filtrate was collected in a flask containing 50 ml of previously cooled 6N hydrochloric isopropanol, the zinc was washed with ethanol, the filtrates were combined and evaporated to dryness.

After drying under vacuum, in the presence of $P_2O_5$ and soda tablets, 1.5 g of a bluish powder corresponding to the expected compound was obtained.

NMR analyses ($^1$H 400 MHz and $^{13}$C 100.61 MHz DMSO $d_6$) were consistent with the expected structure. The quasi-molecular ions [M+H]$^+$ and [M+Na]$^+$ of the expected molecule, $C_{10}H_{14}N_4O$, were mainly detected.

Example 4

N-2-(3-Imidazol-1-yl-propyl)pyrazolo[1,5-a]pyridine-2,3-diamine dihydrochloride

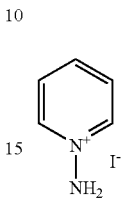

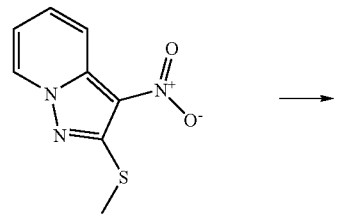

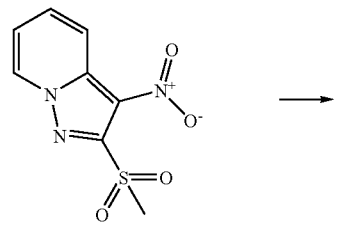

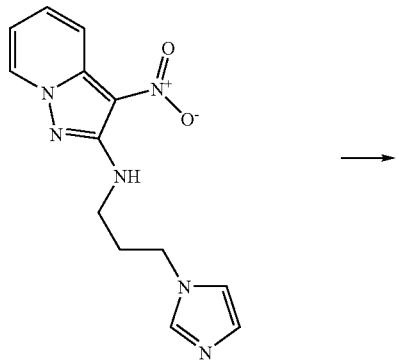

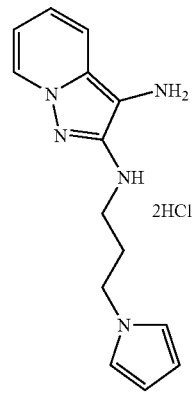

Synthesis of N-[3-(1H-imidazol-1-yl)propyl]-3-nitropyrazolo[1,5-a]pyridin-2-amine

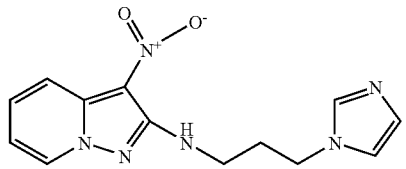

50 ml of N-methylpyrrolidinone, 5 g (0.021 mol) of 2-methanesulphanyl-3-nitropyrazolo[1,5-a]pyridine and 26 g of 3-(1H-imidazol-1-yl)propane-1-amine were put in a 100 ml three-necked flask equipped with a bulb condenser, a thermometer and a magnetic stirrer and stirring was continued for 6 hours, monitoring by TLC (eluent: 95:5 dichloromethane/methanol).

The reaction medium was poured onto a mixture of 200 g of ice and water. The yellow compound that crystallized was drained on a No. 3 frit, washed with water 2×100 ml then with 3×100 ml of isopropyl ether. After drying at 35° C. under vacuum, in the presence of $P_2O_5$, for 12 hours, 5 g of a green solid corresponding to the expected compound was recovered.

NMR analyses ($^1$H 400 MHz and $^{13}$C 100.61 MHz DMSO $d_6$) and mass spectrophotometry were consistent with the expected structure. The quasi-molecular ions [M+H]$^+$, [2M+H]$^+$ of the expected molecule, $C_{13}H_{14}N_6O_2$, were mainly detected.

Synthesis of N-2-(3-imidazol-1-yl-propyl)-pyrazolo[1,5-a]pyridine-2,3-amine dihydrochloride

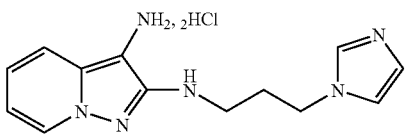

350 ml of ethanol and 5 g of zinc powder were put in a 500 ml three-necked flask equipped with a bulb condenser, a thermometer and a magnetic stirrer, and brought to reflux.

Then 1 g of ammonium chloride dissolved in 0.5 ml water was added, and 1 g of N-[3-(1H-imidazol-1-yl)propyl]-3-nitropyrazolo[1,5-a]pyridin-2-amine was added in portions in 15 minutes. Reflux was maintained for 4 hours.

At the end of reduction, the zinc was removed by filtration under argon on a bed of Celite and the filtrate was collected in a flask containing 50 ml of previously cooled 6N hydrochloric isopropanol. The zinc was washed with ethanol, the filtrates were combined and evaporated to dryness.

After drying under vacuum, in the presence of $P_2O_5$ and soda tablets, 0.5 g of a bluish powder corresponding to the expected compound was obtained. The quasi-molecular ions [M+H]$^+$, [M+Na]$^+$ of the expected molecule, $C_{13}H_{16}N_6$, were mainly detected.

Example 5

2-Pyrrolidin-1-yl-pyrazolo[1,5-a]pyridin-3-ylamine dihydrochloride

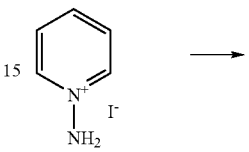

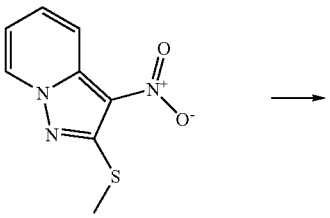

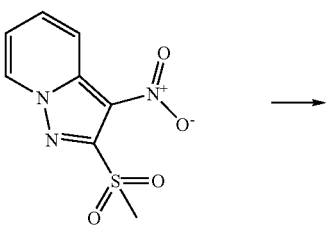

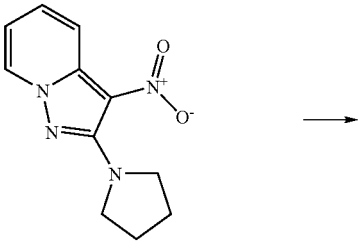

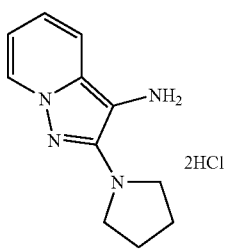

Synthesis of 3-nitro-2-pyrrolidin-1-yl-pyrazolo[1,5-a]pyridine

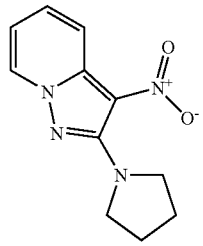

10 ml of N-methylpyrrolidinone, 7.23 g (0.03 mol) 2-methanesulphonyl-3-nitro-pyrazolo[1,5-a]pyridine and 8 ml pyrrolidine were put in a 50 ml three-necked flask equipped with a bulb condenser, a thermometer and a magnetic stirrer. With stirring, the mixture was heated to 70° C. on an oil bath, for 1 hour, with monitoring by TLC (eluent: 98:2 dichloromethane/methanol).

The yellow compound was drained, isolated by pouring the reaction mixture into water, on a frit and then washed with water several times. After drying under vacuum, in the presence of $P_2O_5$, 6.84 g of a yellow solid corresponding to the expected compound was recovered.

NMR analyses ($^1$H 400 MHz and $^{13}$C 100.61 MHz DMSO $d_6$) were consistent with the expected structure.

Synthesis of 2-pyrrolidin-1-yl-pyrazolopyridine[1,5-a]pyridin-3-ylamine dihydrochloride

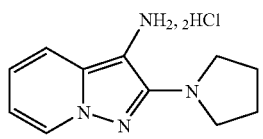

400 ml ethanol and 5 g of zinc powder were put in a 500 ml three-necked flask equipped with a bulb condenser, a thermometer and a magnetic stirrer, and brought to reflux.

Then 1 g of ammonium chloride dissolved in 0.5 ml of water was added, and 1 g of 3-nitro-2-pyrrolidin-1-yl-pyrazolo[1,5-a]pyridine was added in portions in 15 minutes, and reflux was maintained for 4 hours.

At the end of reduction, the zinc was removed by filtration under argon on a bed of Celite and the filtrate was collected in a flask containing 50 ml of previously cooled 6N hydrochloric isopropanol. The zinc was washed with ethanol, the filtrates were combined and evaporated to dryness.

After drying under vacuum, in the presence of $P_2O_5$ and soda tablets, 1.2 g of a bluish powder corresponding to the expected compound was obtained.

NMR analyses ($^1$H 400 MHz and $^{13}$C 100.61 MHz DMSO $d_6$) were consistent with the expected structure.

$^1$H-NMR (DMSO-$d_6$): 1.91 (m, 4H), 3.46 (m, 1H), 6.70 (m, 1H), 7.21 (m, 1H), 7.73 (m, 1H), 7.79 (se, 2H), 8.42 (m, 2H), 10.24 (se, 3H).

The quasi-molecular ions [M+H]$^+$, [M+Na]$^+$ of the expected molecule $C_{11}H_{14}N_4$ were mainly detected.

Example 6

2-(3-Dimethylamino-pyrrolidin-1-yl)-pyrazolo[1,5-a]pyridin-3-ylamine dihydrochloride

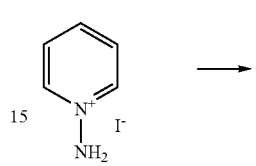

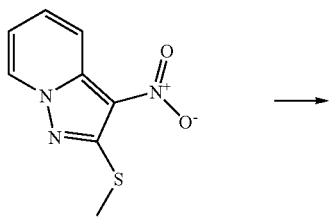

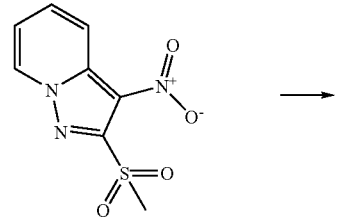

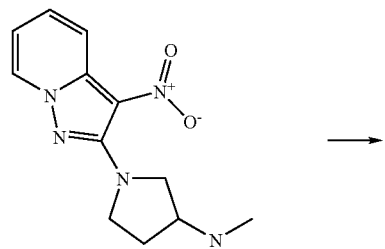

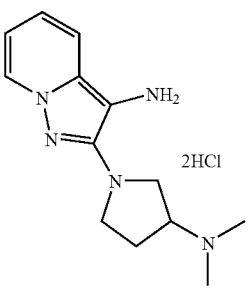

Synthesis of N,N-dimethyl-1-(3-nitropyrazolo[1,5-a]pyridin-2-yl)pyrrolidine-3-amine

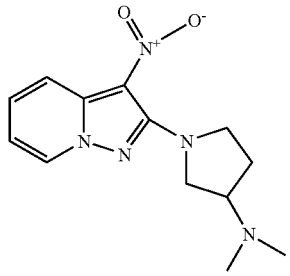

5 ml of N-methylpyrrolidinone, 3 g of 2-(methylsulphonyl)-3-nitropyrazolo[1,5-a]pyridine and 3.77 ml of 3-(dimethylamino)pyrrolidine were put in a 100 ml three-necked flask equipped with a bulb condenser, a thermometer and a magnetic stirrer, and heated to 80° C. for one hour.

The reaction medium was poured onto a mixture of 200 g of ice and water. The yellow compound that crystallized was drained on a frit, washed with 2×100 ml water and then with 3×100 ml isopropyl ether. After drying at 35° C. under vacuum, in the presence of $P_2O_5$, for 12 hours, 3.26 g of a yellow solid corresponding to the expected compound was recovered.

NMR analyses ($^1$H 400 MHz and $^{13}$C 100.61 MHz DMSO $d_6$) and mass spectrophotometry were consistent with the expected structure.

Synthesis of 2-(3-dimethylamino-pyrrolidin-1-yl)-pyrazolo[1,5-a]pyridin-3-ylamine dihydrochloride

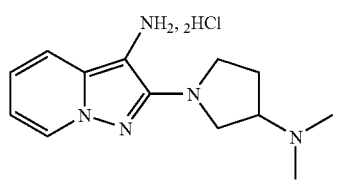

400 ml ethanol and 5 g of zinc powder were put in a 500 ml three-necked flask equipped with a bulb condenser, a thermometer and a magnetic stirrer, and brought to reflux.

Then 1 g of ammonium chloride dissolved in 0.5 ml of water was added, and 1 g of N,N-dimethyl-1-(3-nitropyrazolo[1,5-a]pyridin-2-yl)pyrrolidine-3-amine was added in portions in 15 minutes, and reflux was maintained for 4 hours.

At the end of reduction, the zinc was removed by filtration under argon on a bed of Celite and the filtrate was collected in a flask containing 50 ml of previously cooled 6N hydrochloric isopropanol. The zinc was washed with ethanol, the filtrates were combined and evaporated to dryness.

After drying under vacuum, in the presence of $P_2O_5$ and soda tablets, 0.9 g of a bluish powder corresponding to the expected compound was obtained.

NMR analyses ($^1$H 400 MHz and $^{13}$C 100.61 MHz DMSO $d_6$) were consistent with the expected structure. The quasi-molecular ions $[M+H]^+$, $[M+Na]^+$ of the expected molecule, $C_{13}H_{19}N_5$, were mainly detected.

Example 7

2-Imidazol-1-yl-pyrazolo[1,5-a]pyridin-3-ylamine dihydrochloride

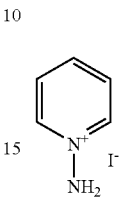

→

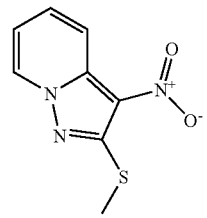

→

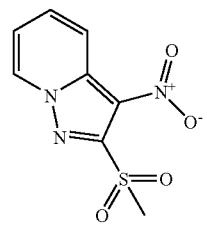

→

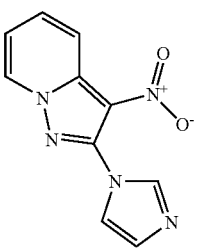

→

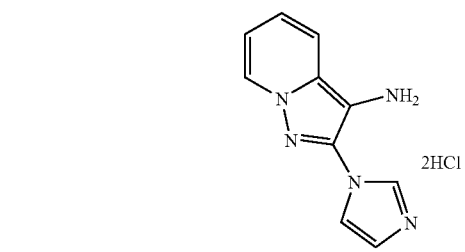

Synthesis of 2-imidazol-1-yl-3-nitropyrazolo[1,5-a]pyridine

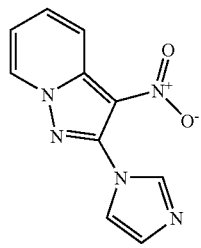

In a 100 ml three-necked flask equipped with a magnetic stirrer, a thermometer and a condenser, 5 g of 2-methanesulphanyl-3-nitropyrazolo[1,5-a]pyridine, 20 ml of N-methylpyrrolidinone and 7 g of imidazole were loaded successively.

This mixture was heated at 100° C. for 30 minutes then, after cooling, the 2-imidazol-1-yl-3-nitropyrazolo[1,5-a]pyridine was precipitated in 5 volumes of water.

After draining and drying under vacuum in the presence of phosphorus pentoxide, 4.23 g of a yellow solid was recovered.

NMR analyses ($^1$H 400 MHz and $^{13}$C 100.61 MHz DMSO $d_6$) were consistent with the expected structure. The mass of the expected compound, $C_{10}H_7N_5O_2$, was detected in mass spectrometry.

Synthesis of 2-imidazol-1-yl-pyrazolopyridine[1,5-a]pyridin-3-ylamine dihydrochloride

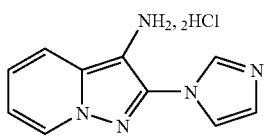

200 ml of ethanol and 6 g of zinc powder were put in a 500 ml three-necked flask equipped with a bulb condenser, a thermometer and a magnetic stirrer, and brought to reflux.

Then 1 g of ammonium chloride dissolved in 0.5 ml of water was added, and 2 g of 2-imidazol-1-yl-3-nitropyrazolo[1,5-a]pyridine was added in portions in 15 minutes, and reflux was maintained for 4 h.

At the end of reduction, the zinc was removed by filtration under argon on a bed of Celite and the filtrate was collected in a flask containing 50 ml of previously cooled 6N hydrochloric isopropanol. The zinc was washed with ethanol, the combined liquors were concentrated to ⅓ and the product formed was filtered on a frit.

After drying under vacuum, in the presence of $P_2O_5$ and soda tablets, 2.5 g of a light pink powder corresponding to the expected compound was obtained.

NMR analyses ($^1$H 400 MHz and $^{13}$C 100.61 MHz DMSO $d_6$) were consistent with the expected structure.

$^1$H-NMR (DMSO-$d_6$): 7.07 (m, 1H), 7.37 (dd, 1H), 7.97 (m, 2H), 8.23 (dd, 1H), 8.67 (d, 1H), 9.78 (se, 1H).

The quasi-molecular ions [M+H]$^+$, [M+Na]$^+$ of the expected molecule, $C_{10}H_9N_5$, were mainly detected.

Example 8

N-2-(2-Pyrrolidin-1-ylethyl)pyrazolo[1,5-a]pyridine-2,3-diamine dihydrochloride

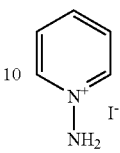

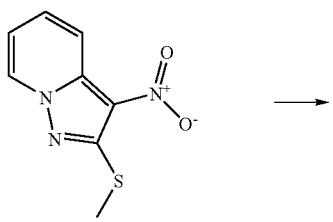

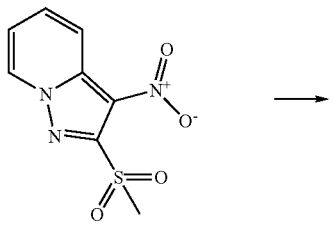

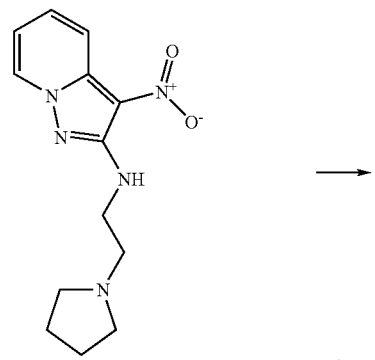

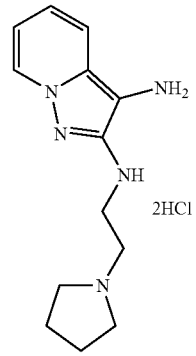

Synthesis of 3-nitro-N-(2-pyrrolidin-1-ylethyl)pyrazolo[1,5-a]pyridin-2-amine

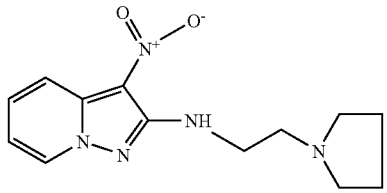

20 ml of N-methylpyrrolidinone, 15 g (0.062 mol) 2-methanesulphanyl-3-nitropyrazolo[1,5-a]pyridine and 16 ml of 2,3-aminoethylpyrrolidine were put in a 100 ml three-necked flask equipped with a bulb condenser, a thermometer and a magnetic stirrer. While being stirred, the mixture was heated to 80° C. on an oil bath for 1 hour, monitoring by TLC (eluent: 90:5 ethyl acetate/methanol).

The reaction mixture was cooled to room temperature, then poured onto a mixture of 400 g of ice and water. The yellowish-beige precipitate that forms was drained on a frit and then washed several times with water. After drying at 35° C. under vacuum, in the presence of $P_2O_5$, 15.2 g of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of N-2-(2-pyrrolidin-1-ylethyl)pyrazolo[1,5-a]pyridine-2,3-diamine dihydrochloride

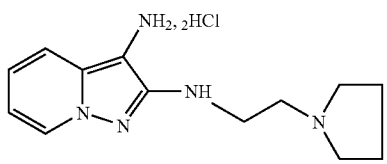

200 ml of ethanol and 5 g of zinc powder were put in a 250 ml three-necked flask equipped with a bulb condenser, a thermometer and a magnetic stirrer, and brought to reflux.

Then 2 ml of acetic acid were added dropwise, and then, in portions, 5 g of 3-nitro-N-(2-pyrrolidin-1-ylethyl)pyrazolo[1,5-a]pyridin-2-amine. At the end of discharge, 1 ml of acetic acid was added dropwise and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a greyish-blue solid was observed; this was drained on a No. 3 frit and then washed with 2×15 ml ethanol and 2×50 ml isopropyl ether. After drying under vacuum, in the presence of $P_2O_5$ and soda tablets, 5 g of a bluish powder corresponding to the expected compound was recovered.

NMR analyses ($^1$H 400 MHz and $^{13}$C 100.61 MHz DMSO $d_6$) were consistent with the expected structure.

$^1$H-NMR (DMSO $d_6$): 1.83 (m, 2H), 1.99 (m, 2H), 3.07 (m, 2), 3.38 (m, 2H), 3.63 (m, 4H), 6.71 (m, 1H), 7.24 (m, 1H), 7.50 (d, 1H), 8.42 (d, 1H), 10.13 (se, 1H), 10.25 (se, 3H).

The quasi-molecular ions [M+H]$^+$, [M+Na]$^+$, [M+Na+CH$_3$OH]$^+$, [2M+H]$^+$, [2M+Na]$^+$ of the expected molecule, $C_{13}H_{19}N_5$, were mainly detected.

Example 9

2-(3-Amino-pyrazolo[1,5-a]pyridin-2-yloxy)-ethanol dihydrochloride

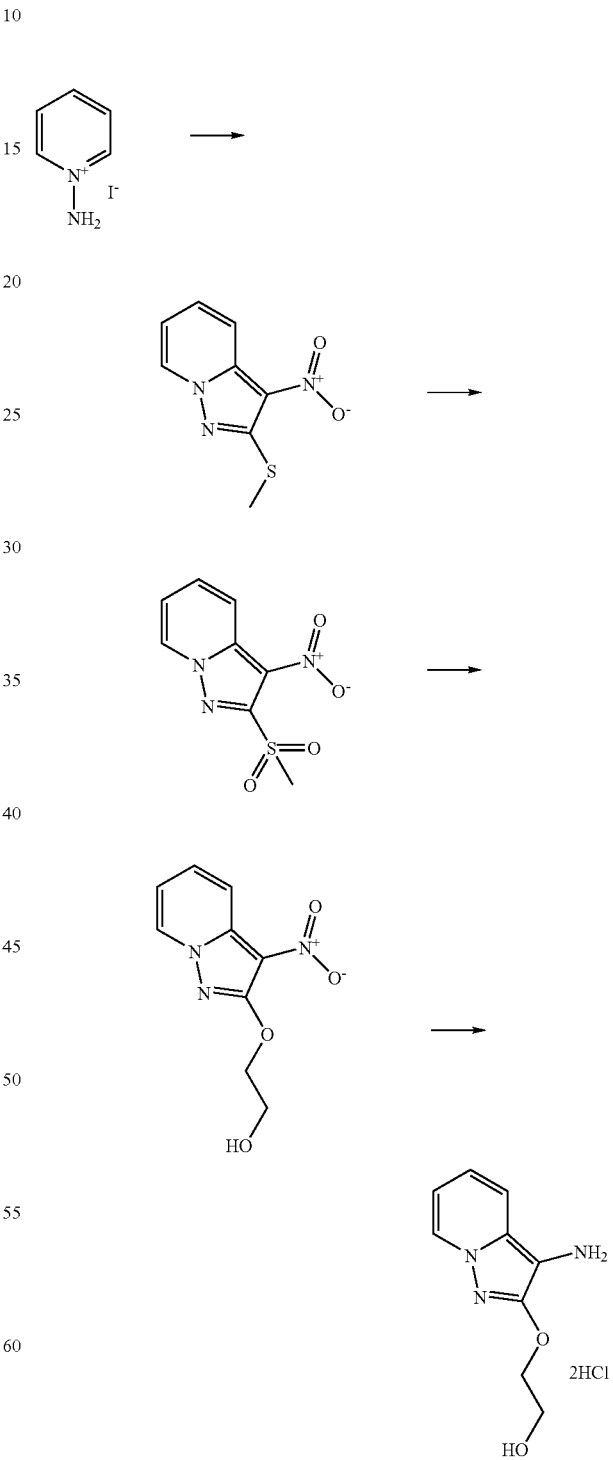

Synthesis of 2-[(3-nitropyrazolo[1,5-a]pyridin-2-yl)amino]ethanol

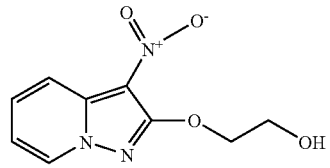

20 ml of ethylene glycol, 4.2 g of soda tablets dissolved in 10 ml water and a solution of 2.5 g of 2-methanesulphanyl-3-nitropyrazolo[1,5-a]pyridine and 20 ml of N-methylpyrrolidinone were put in a 100 ml three-necked flask equipped with a bulb condenser, a thermometer and a magnetic stirrer. While being stirred, the mixture was heated to 30° C. on an oil bath for 1 hour, with monitoring by TLC (eluent: 90:5 ethyl acetate/methanol).

The reaction mixture was cooled to room temperature and then poured into a mixture of 450 g of ice and water. After being neutralized with hydrochloric acid, the yellowish-beige precipitate that formed was drained on a frit and then washed with water several times. After drying at 35° C. under vacuum, in the presence of $P_2O_5$, 20.2 g of a yellow solid corresponding to the expected compound was recovered.

NMR analyses ($^1H$ 400 MHz and $^{13}C$ 100.61 MHz DMSO $d_6$) and mass spectrometry were consistent with the expected structure.

Synthesis of 2-(3-amino-pyrazolo[1,5-a]pyridin-2-yloxy)-ethanol dihydrochloride

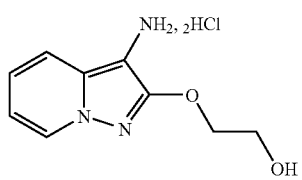

50 ml of ethanol and 5 ml of hydrochloric acid were put in a 100 ml three-necked flask equipped with a bulb condenser, a thermometer and a magnetic stirrer, and then added in portions, under reflux, was a mixture of 1.2 g of zinc and 500 mg of methanesulphanyl-3-nitropyrazolo[1,5-a]pyridine.

At the end of addition, reflux was maintained for 2 hours, then the zinc was removed by filtration under argon on a bed of Celite and the filtrate was collected in a flask containing 50 ml of previously cooled 6N hydrochloric isopropanol.

The filtrates were evaporated to dryness and taken up three times in a solution of hydrochloric ether followed by evaporation, to obtain a thick blue liquid.

This liquid was poured progressively, with stirring and priming, on isopropyl ether. Precipitation of a blue solid was observed; this was drained on a No. 3 frit and washed with 2×50 ml of isopropyl ether. After drying under vacuum, in the presence of $P_2O_5$ and soda tablets, a bluish powder corresponding to the expected compound was recovered.

Mass Analysis:
The quasi-molecular ions [M+H]$^+$, [M+Na]$^+$ and [M−H]$^-$ of the expected molecule, $C_9H_{11}N_3O_2$, were mainly detected.

Example 10

2-Ethoxy-pyrazolo[1,5-a]pyridin-3-ylamine trihydrochloride

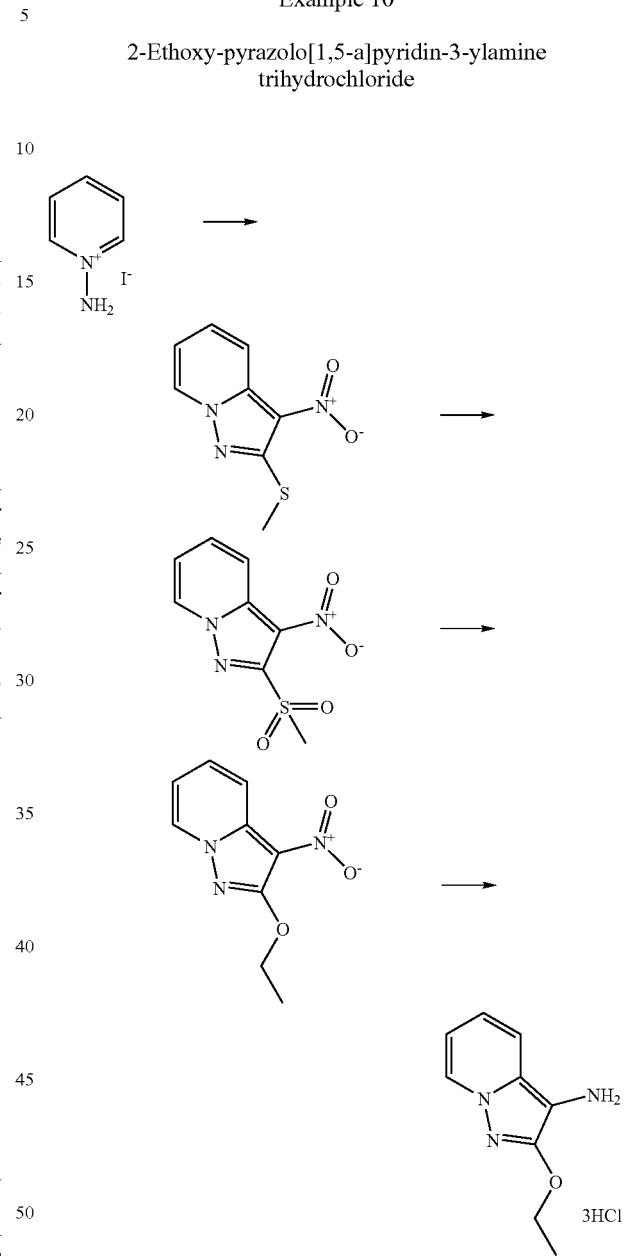

Synthesis of 2-ethoxy-3-nitropyrazolo[1,5-a]pyridine

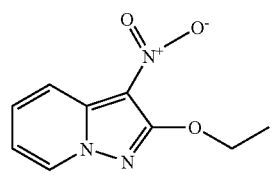

50 ml of sodium ethylate and 4.9 g of methanesulphanyl-3-nitropyrazolo[1,5-a]pyridine were put in a 100 ml three-necked flask equipped with a bulb condenser, a thermometer and a magnetic stirrer, and reflux for 0.5 h, with stirring.

The reaction mixture was stirred into 500 ml of water, the compound that crystallized was drained on a frit and washed with water then with 3×50 ml of isopropyl ether. After drying at 35° C. under vacuum in the presence of $P_2O_5$ for 12 hours, 4 g of a beige solid corresponding to the expected compound was recovered.

NMR analyses ($^1$H 400 MHz and $^{13}$C 100.61 MHz DMSO $d_6$) and mass spectrometry were consistent with the expected structure.

Synthesis of 2-ethoxy-pyrazolo[1,5-a]pyridin-3-ylamine trihydrochloride

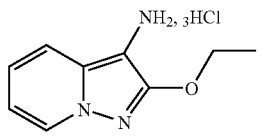

350 ml of ethanol and 12 g of zinc powder were put in a 500 ml three-necked flask equipped with a bulb condenser, a thermometer and a magnetic stirrer, and brought to reflux.

Then 500 mg of ammonium chloride were added and then, in portions, 3.88 g of 2-ethoxy-3-nitropyrazolo[1,5-a]pyridine.

At the end of addition, by maintaining reflux for 2 hours, reduction was completed. The zinc was removed by filtration under argon on a bed of Celite and the filtrate was collected in a flask containing 50 ml of previously cooled 6N hydrochloric isopropanol.

Precipitation of a solid was promoted by adding isopropyl ether to the filtrate. The cream solid obtained was drained on a frit, and washed with 2×15 ml of ethanol and 2×50 ml of isopropyl ether. After drying under vacuum, in the presence of $P_2O_5$ and soda tablets, a beige-cream powder corresponding to the expected compound was recovered.

NMR analyses ($^1$H 400 MHz and $^{13}$C 100.61 MHz $D_2O$) were consistent with the expected structure.

$^1$H-NMR ($D_2O$): 1.45 (t, 3H), 4,43 (q, 2H), 6.91 (m, 1H), 7.41 (m, 1H), 7.51 (m, 1H), 8.3 (m, 1H).

Mass Analysis:

The quasi-molecular ions [M+H]$^+$, [M+Na]$^+$ and [M−H]$^−$ of the expected molecule, $C_9H_{11}N_3O$, were mainly detected.

Example 11

N-2-(2-piperidin-1-ylethyl)pyrazolo[1,5-a]pyridine-2,3-diamine dihydrochloride

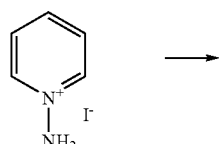

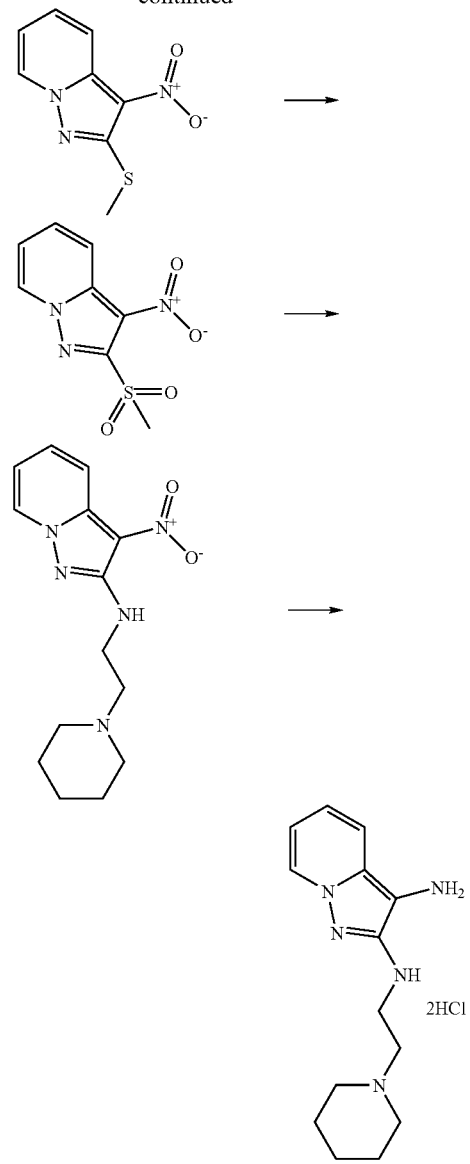

Synthesis of 3-nitro-N-(2-piperidin-1-ylethyl)pyrazolo[1,5-a]pyridin-2-amine

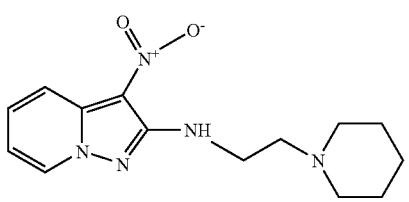

100 ml of N-methylpyrrolidinone, 20 g (0.0711 mol) of 2-methanesulphanyl-3-nitropyrazolo[1,5-a]pyridine and 20.3 ml (0.142 mol) of 2-piperidin-1-ylethane-amine were put in a 250 ml three-necked flask equipped with a bulb condenser, a thermometer and a magnetic stirrer. While being stirred, the mixture was heated to 70° C. on an oil bath for 4 hours, with monitoring by TLC (eluent: 95:5 dichloromethane/methanol).

The reaction mixture was cooled to room temperature and poured onto a mixture of 400 g of ice and water. The beige compound that crystallized was drained on a No. 4 frit and then washed with water several times. After drying at 35° C. under vacuum in the presence of $P_2O_5$, 20.43 g of a yellow solid corresponding to the expected compound was recovered.

NMR analyses ($^1$H 400 MHz and $^{13}$C 100.61 MHz DMSO $d_6$) were consistent with the expected structure. The mass of the expected compound, $C_{14}H_{19}N_5O_2$, was detected in mass spectrometry.

The quasi-molecular ions $[M+H]^+$, $[M+Na]^+$, $[M+Na+CH_3OH]^+$ of the expected molecule, $C_{14}H_{19}N_5O_2$, were mainly detected.

Synthesis of N-2-(2-piperidin-1-ylethyl)pyrazolo[1,5-a]pyridine-2,3-diamine dihydrochloride

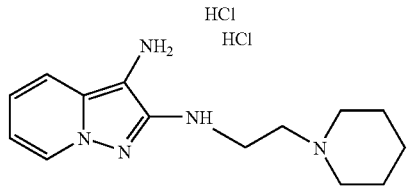

150 ml of ethanol and 2 g of zinc powder were put in a 250 ml three-necked flask equipped with a bulb condenser, a thermometer and a magnetic stirrer, and brought to reflux.

Then 2 ml of acetic acid was added dropwise, and then in portions 2 g of 3-nitro-N-(2-piperidin-1-ylethyl)pyrazolo[1,5-a]pyridin-2-amine was also added dropwise. At the end of discharge, 1 ml of acetic acid was added dropwise and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a greyish-blue solid was observed. This was drained on a No. 3 frit and washed with 2×15 ml of ethanol and 2×50 ml of isopropyl ether. After drying under vacuum in the presence of $P_2O_5$ and soda tablets, 2 g of a greyish-blue powder corresponding to the expected compound was recovered.

NMR analyses ($^1$H 400 MHz and $^{13}$C 100.61 MHz DMSO $d_6$) were consistent with the expected structure.

Example 12

N-2-[2-(diisopropylamino)ethyl]pyrazolo[1,5-a]pyridine-2,3-diamine dihydrochloride

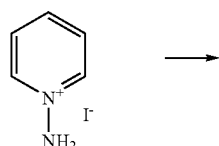

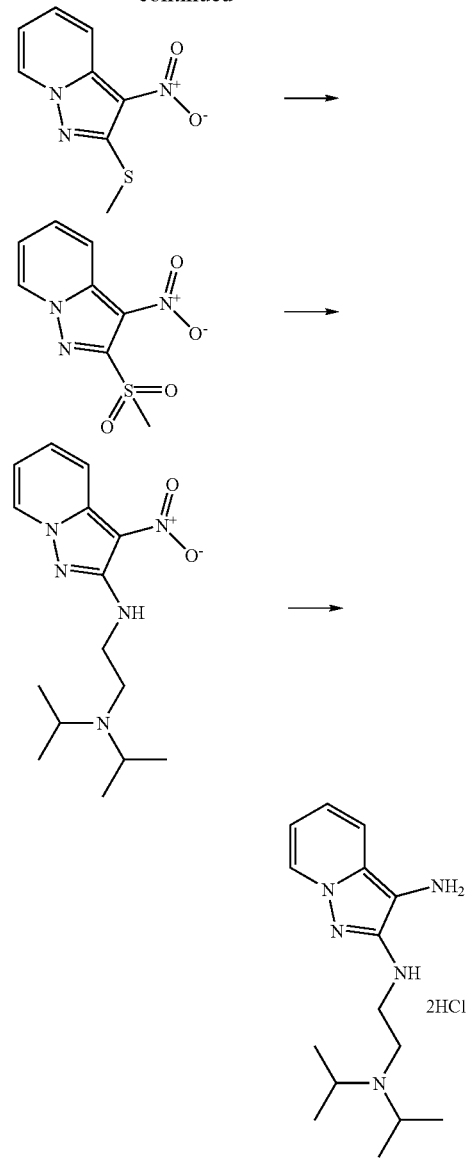

Synthesis of N,N-diisopropyl-N'-(3-nitropyrazolo[1,5-a]pyridin-2-yl)ethane-1,2-diamine

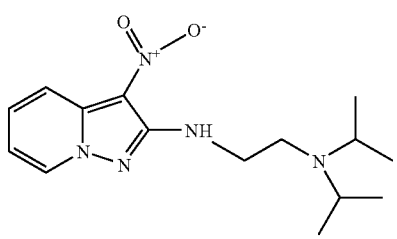

20 ml of N-methylpyrrolidinone, 10 g (0.0414 mol) of 2-methanesulphanyl-3-nitropyrazolo[1,5-a]pyridine and 14.4 ml (0.082 mol) of N,N-diisopropylethane-1,2-diamine were put in a 100 ml three-necked flask equipped with a bulb condenser, a thermometer and a magnetic stirrer. While being stirred, the mixture was heated to 70° C. on an oil bath for 1 hour, with monitoring by TLC (eluent: 95:5 dichloromethane/methanol).

The reaction mixture was cooled to room temperature, and poured onto a mixture of 100 g of ice and water. The yellow precipitate that forms was drained on a No. 3 frit, then washed with water and then with 3×100 ml of petroleum ether. After drying at 35° C. under vacuum in the presence of $P_2O_5$, 11.88 g of a yellow solid corresponding to the expected compound was recovered.

NMR analyses ($^1$H 400 MHz and $^{13}$C 100.61 MHz DMSO $d_6$) were consistent with the expected structure. The quasi-molecular ions [M+H]$^+$, [M+Na]$^+$, [M+Na+CH$_3$OH]$^+$ of the expected molecule, $C_{15}H_{23}N_5O_2$ were mainly detected.

Synthesis of N-2-[2-(diisopropylamino)ethyl]pyrazolo[1,5-a]pyridine-2,3-diamine dihydrochloride

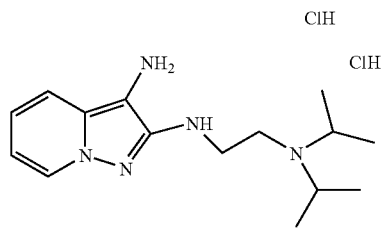

150 ml of ethanol and 2 g of zinc powder were put in a 250 ml three-necked flask equipped with a bulb condenser, a thermometer and a magnetic stirrer, and brought to reflux;

Then 1.75 ml of acetic acid were added dropwise and then, in portions, 1.75 g of N,N-diisopropyl-N'-(3-nitropyrazolo[1,5-a]pyridin-2-yl)ethane-1,2-diamine was also added dropwise. At the end of discharge, 1 ml of acetic acid were added dropwise, and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a greyish-blue solid was then observed. This was drained on a No. 3 frit, and washed with 2×15 ml of ethanol and 2×50 ml of isopropyl ether. After drying under vacuum in the presence of $P_2O_5$ and soda tablets, a greyish-blue powder corresponding to the expected compound was recovered.

NMR analyses ($^1$H 400 MHz and $^{13}$C 100.61 MHz DMSO $d_6$) were consistent with the expected structure.

The mass of the expected compound $C_{15}H_{25}N_5$ was detected in mass spectrometry.

The quasi-molecular ions [M+H]$^+$, [M+Na]$^+$, [M+Na+CH$_3$OH]$^+$ of the expected molecule, $C_{15}H_{25}N_5$, were mainly detected.

Example 13

N-2-[2-(diethylamino)ethyl]pyrazolo[1,5-a]pyridine-2,3-diamine dihydrochloride

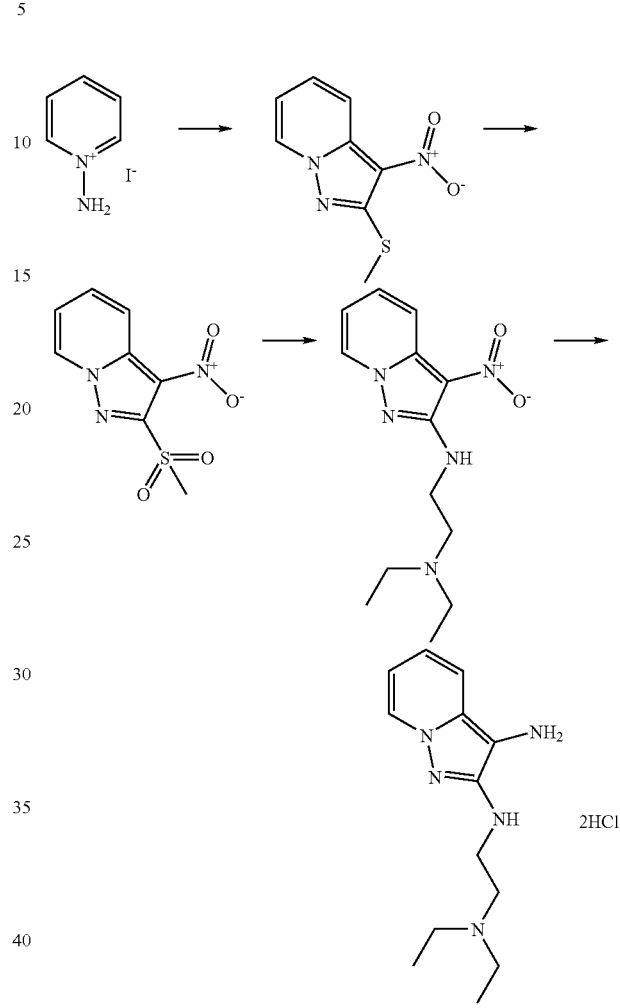

Synthesis of N,N-diethyl-N'-(3-nitropyrazolo[1,5-a]pyridin-2-yl)ethane-1,2-diamine

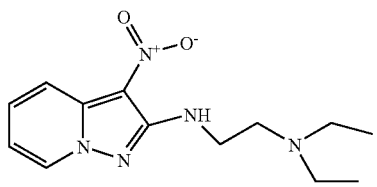

100 ml of N-methylpyrrolidinone, 10 g (0.0414 mol) 2-methanesulphanyl-3-nitropyrazolo[1,5-a]pyridine and 11.65 ml (0.0829 mol) of N,N-diethylenediamine were put in a 100 ml three-necked flask equipped with a bulb condenser, a thermometer and a magnetic stirrer. While being stirred, the mixture was heated to 70° C. on an oil bath for 4 hours.

The reaction mixture was cooled to room temperature and poured onto a mixture of 100 g of ice and water. The yellow compound that crystallized was drained on a No. 3 frit and then washed with 3×100 ml of petroleum ether. After drying at 35° C. under vacuum in the presence of P$_2$O$_5$, 9.80 g of a yellow solid corresponding to the expected compound was recovered.

NMR analyses ($^1$H 400 MHz and $^{13}$C 100.61 MHz DMSO d$_6$) were consistent with the expected structure. The quasi-molecular ions [M+H]$^+$, [M+Na]$^+$, [M+Na+CH$_3$OH]$^+$ of the expected molecule, C$_{13}$H$_{19}$N$_5$O$_2$ were mainly detected.

Synthesis of N-2-[2-(diethylamino)ethyl]pyrazolo[1,5-a]pyridine-2,3-diamine dihydrochloride

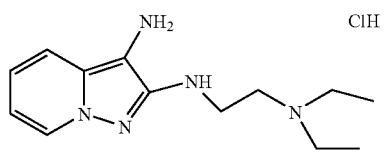

150 ml of ethanol and 2 g of zinc powder were put in a 250 ml three-necked flask equipped with a bulb condenser, a thermometer and a magnetic stirrer, and brought to reflux.

Then added dropwise were 2 ml of acetic acid and then, in portions, 2 g of N,N-diisopropyl-N'-(3-nitropyrazolo[1,5-a]pyridin-2-yl)ethane-1,2-diamine. At the end of discharge, 1 ml of acetic acid was added dropwise, and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a greyish-blue solid was then observed. This was drained on a frit, and washed with 2×15 ml of ethanol and 2×50 ml of isopropyl ether. After drying under vacuum in the presence of P$_2$O$_5$ and soda tablets, 2 g of a greyish-green powder corresponding to the expected compound was recovered.

NMR analyses ($^1$H 400 MHz and $^{13}$C 100.61 MHz DMSO d$_6$) were consistent with the expected structure.

The mass of the expected compound C$_{13}$H$_{21}$N$_5$ was detected in mass spectrometry.

The quasi-molecular ions [M+H]$^+$, [M+Na]$^+$, [M+Na+CH$_3$OH]$^+$ of the expected molecule, C$_{13}$H$_{21}$N$_5$, were mainly detected.

Example 14

N-2-(2-pyridin-3-ylethyl)pyrazolo[1,5-a]pyridine-2,3-diamine dihydrochloride

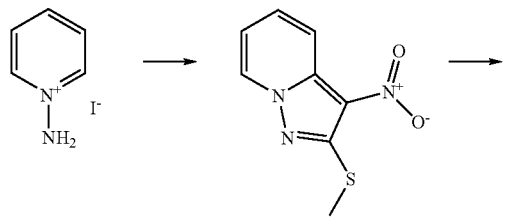

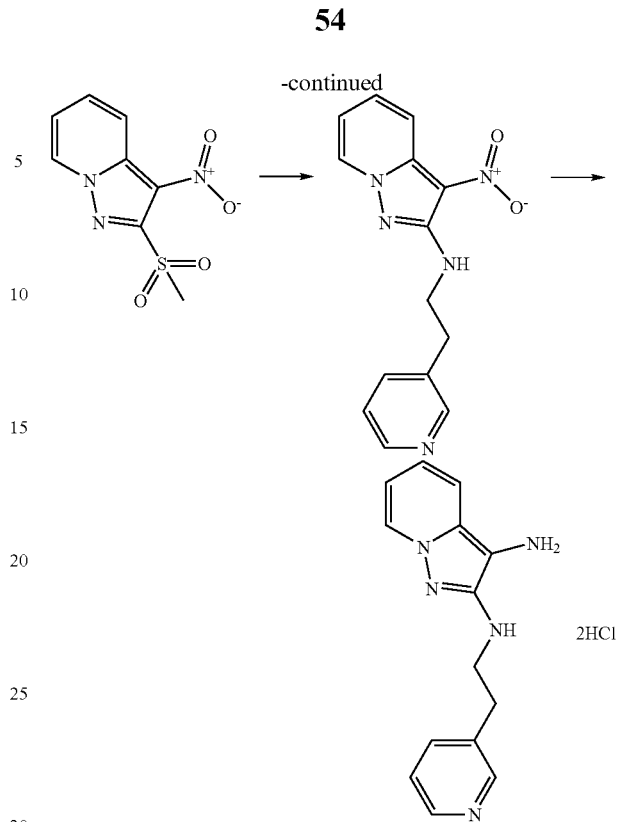

Synthesis of 3-nitro-N-(2-pyridin-3-ylethyl)pyrazolo[1,5-a]pyridin-2-amine

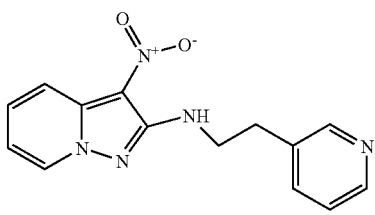

10 ml of N-methylpyrrolidinone, 4.93 g (0.02046 mol) 2-methanesulphanyl-3-nitropyrazolo[1,5-a]pyridine and 5 g ml (0.04092 mol) of 3-(2-aminoethyl)-pyridine were put in a 100 ml three-necked flask equipped with a bulb condenser, a thermometer and a magnetic stirrer. While being stirred, the mixture was heated to 70° C. on an oil bath for 1 hour.

The reaction mixture was cooled to room temperature and then poured onto a mixture of 100 g of ice and water. The yellow compound that crystallized was drained on a frit, washed with water and then with 3×100 ml of petroleum ether. After drying at 35° C. under vacuum in the presence of P$_2$O$_5$, 5.61 g of a yellow solid corresponding to the expected compound was recovered.

NMR analyses ($^1$H 400 MHz and $^{13}$C 100.61 MHz DMSO d$_6$) were consistent with the expected structure.

The quasi-molecular ions [M+H]$^+$, [M+Na]$^+$, [M+Na+CH$_3$OH]$^+$, [2M+H]$^+$, [2M+Na]$^+$ of the expected molecule C$_{14}$H$_{13}$N$_5$O$_2$ were mainly detected.

Synthesis of N-2-(2-pyridin-3-ylethyl)pyrazolo[1,5-a]pyridine-2,3-diamine dihydrochloride

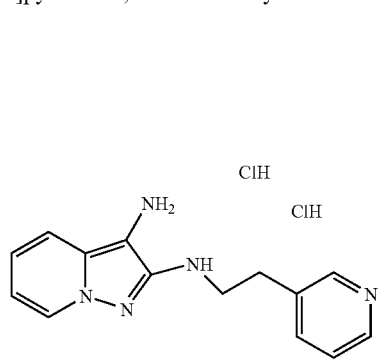

150 ml of ethanol and 2 g of zinc powder were put in a 250 ml three-necked flask equipped with a bulb condenser, a thermometer and a magnetic stirrer, and brought to reflux.

Then added dropwise were 2 ml of acetic acid and then, in portions, 1.6 g of 3-nitro-N-(2-pyridin-3-ylethyl)pyrazolo[1,5-a]pyridin-2-amine. At the end of discharge, 1 ml of acetic acid was added dropwise, and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a greyish-blue solid was then observed. This was drained on a No. 3 frit and washed with 2×15 ml of ethanol and 2×50 ml of isopropyl ether. After drying under vacuum in the presence of $P_2O_5$ and soda tablets, 1.46 g of a greyish-green powder corresponding to the expected compound was recovered.

NMR analyses ($^1$H 400 MHz and $^{13}$C 100.61 MHz DMSO $d_6$) were consistent with the expected structure.

The quasi-molecular ions $[M+H]^+$, $[M+Na]^+$, $[M+Na+CH_3OH]^+$, $[2M+H]^+$, $[2M+Na]^+$ of the expected molecule, $C_{14}H_{15}N_5$, were mainly detected.

Example 15

N-2-(2-pyridin-4-ylethyl)pyrazolo[1,5-a]pyridine-2,3-diamine dihydrochloride

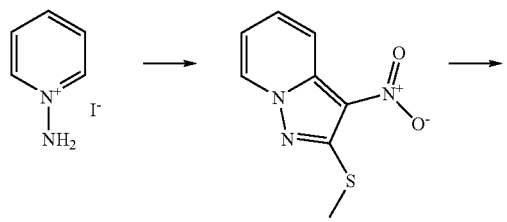

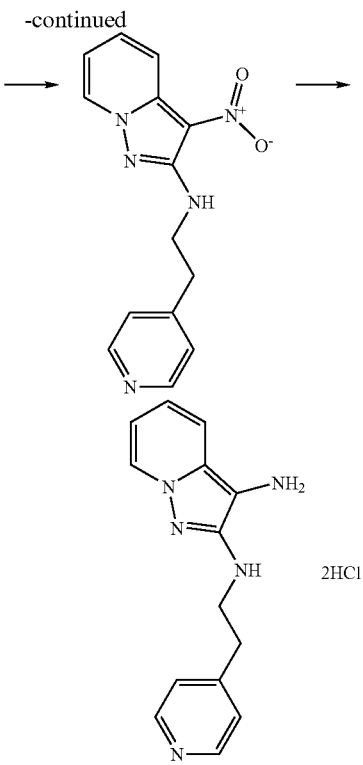

Synthesis of 3-nitro-N-(2-pyridin-4-ylethyl)pyrazolo[1,5-a]pyridin-2-amine

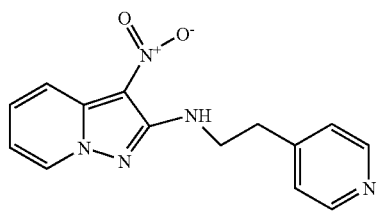

50 ml of N-methylpyrrolidinone, 10 g (0.03555 mol) 2-methanesulphanyl-3-nitro-pyrazolo[1,5-a]pyridine and 8.68 g (0.07110 mol) of 4-(2-aminoethyl) were put in a 100 ml three-necked flask equipped with a bulb condenser, a thermometer and a magnetic stirrer. While being stirred, the mixture was heated to 70° C. on an oil bath for 4 hours, with monitoring by TLC (eluent: 95:5 dichloromethane/methanol).

The reaction mixture was cooled to room temperature and poured onto a mixture of 200 g of ice and water. The yellow compound that crystallized was drained on a No. 3 frit, and washed with water and then with 3×100 ml of petroleum ether. After drying at 35° C. under vacuum in the presence of $P_2O_5$ for 12 hours, 10.81 g (product not totally dry) of a yellow solid corresponding to the expected compound was recovered.

NMR analyses ($^1$H 400 MHz and $^{13}$C 100.61 MHz DMSO $d_6$) were consistent with the expected structure.

Synthesis of N-2-(2-pyridin-4-ylethyl)pyrazolo[1,5-a]pyridine-2,3-diamine dihydrochloride

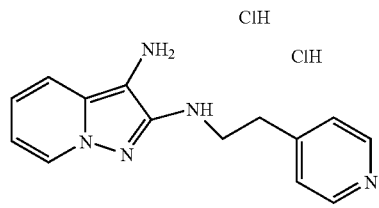

150 ml of ethanol and 2 g of zinc powder were put in a 250 ml three-necked flask equipped with a bulb condenser, a thermometer and a magnetic stirrer, and brought to reflux.

Then added dropwise were 2 ml of acetic acid and then, in portions, 2 g of 3-nitro-N-(2-pyridin-4-ylethyl)pyrazolo[1,5-a]pyridin-2-amine. At the end of discharge, 1 ml of acetic acid was added dropwise, and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a greyish-blue solid was then observed. This was drained on a frit and washed with 2×15 ml of ethanol and 2×50 ml of isopropyl ether. After drying under vacuum in the presence of $P_2O_5$ and soda tablets, 1.8 g of a greyish-green powder corresponding to the expected compound was recovered.

NMR analyses ($^1$H 400 MHz and $^{13}$C 100.61 MHz DMSO $d_6$) were consistent with the expected structure.

$^1$H-NMR (DMSO-$d_6$): 3.21 (t, 2H), 3.64 (t, 2H), 6.66 (m, 1), 7.19 (m, 1H), 7.50 (m, 1H), 8.04 (d, 2H), 8.39 (m, 1H), 8.82 (d, 2H).

The quasi-molecular ions [M+H]$^+$, [M+Na]$^+$, [M+Na+CH$_3$OH]$^+$, [2M+H]$^+$, [2M+Na]$^+$ of the expected molecule, $C_{14}H_{15}N_5$, were mainly detected.

Example 16

N-2-[2-(4-methylpiperazin-1-yl)ethyl]pyrazolo[1,5-a]pyridine-2,3-diamine dihydrochloride

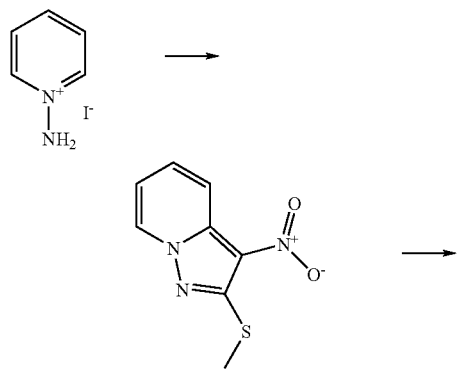

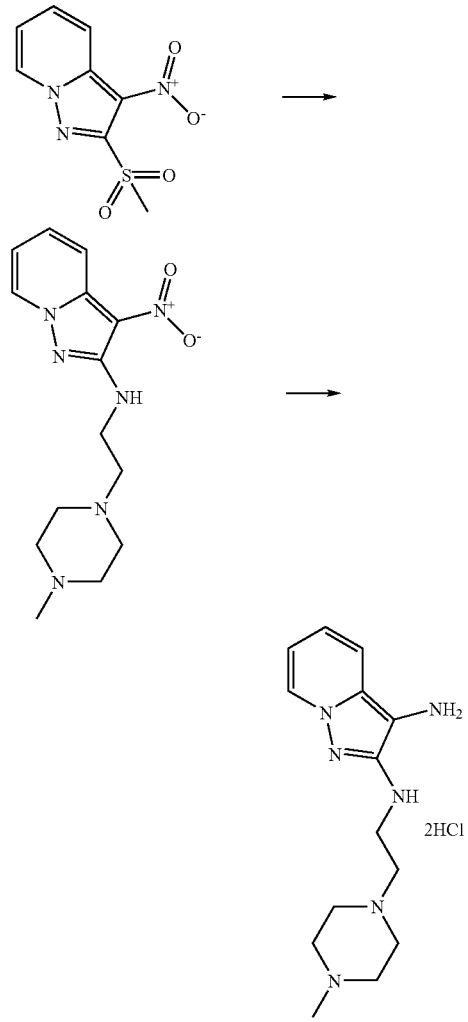

Synthesis of N-[2-(4-methylpiperazin-1-yl)ethyl]-3-nitropyrazolo[1,5-a]pyridin-2-amine

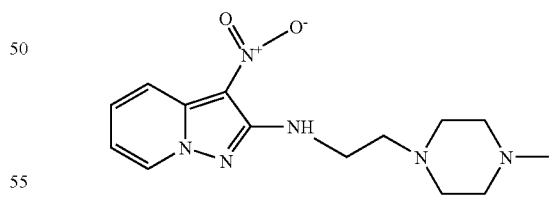

10 ml of N-methylpyrrolidinone, 7.23 g (0.03 mol) 2-methanesulphanyl-3nitro-pyrazolo[1,5-a]pyridine and 10 ml (0.1 mol) of N-methylpiperidine were put in a 50 ml three-necked flask equipped with a bulb condenser, a thermometer and a magnetic stirrer. While being stirred, the mixture was heated to 70° C. on an oil bath for 4 hours.

The reaction mixture was cooled to room temperature and poured onto a mixture of 400 g of ice and water. The beige compound that crystallized was drained on a frit and then washed with water several times. After drying at 35° C. under vacuum in the presence of $P_2O_5$, 7.99 g of a yellow solid corresponding to the expected compound was recovered.

NMR analyses ($^1$H 400 MHz and $^{13}$C 100.61 MHz DMSO $d_6$) were consistent with the expected structure.

The mass of the expected compound $C_{12}H_{15}N_5O_2$ was detected in mass spectrometry.

The quasi-molecular ions [M+H]$^+$, [M+Na]$^+$, [M+Na+CH$_3$OH]$^+$ of the expected molecule $C_{12}H_{15}N_5O_2$ were mainly detected.

Synthesis of N-2-[2-(4-methylpiperazin-1-yl)ethyl] pyrazolo[1,5-a]pyridine-2,3-diamine dihydrochloride

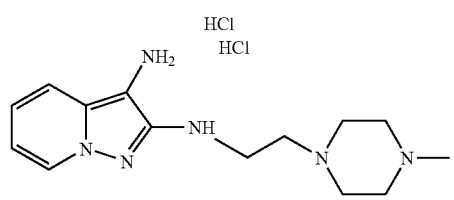

200 ml ethanol and 6 g of zinc powder were put in a 500 ml three-necked flask equipped with a bulb condenser, a thermometer and a magnetic stirrer, and brought to reflux.

Then 1 g of ammonium chloride dissolved in 0.5 ml of water was added, and then 2 g of N-[2-(4-methylpiperazin-1-yl)ethyl]-3-nitropyrazolo[1,5-a]pyridin-2-amine was added in portions in 15 minutes, and reflux was maintained for 2 hours.

At the end of reduction, the zinc was removed by filtration under argon on a bed of Celite and the filtrate was collected in a flask containing 50 ml of previously cooled 6N hydrochloric isopropanol, washed with ethanol and the combined filtrates were diluted with isopropyl ether. The solid that formed was drained on a frit.

After drying under vacuum in the presence of $P_2O_5$ and soda tablets, 0.3 g of a light bluish-green powder corresponding to the expected compound was obtained.

NMR analyses ($^1$H 400 MHz and $^{13}$C 100.61 MHz DMSO $d_6$) were consistent with the expected structure.

Example 17

2-methoxy-7-methyl-pyrazolopyridine[1,5-a]pyridin-3-ylamine hydrochloride

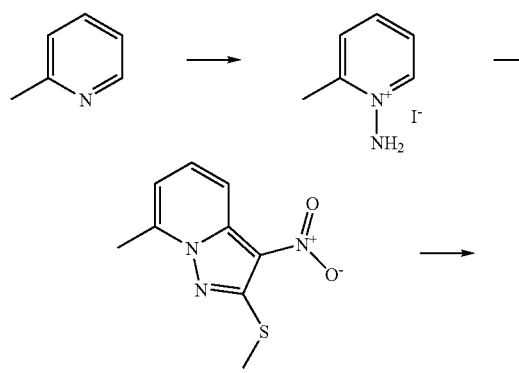

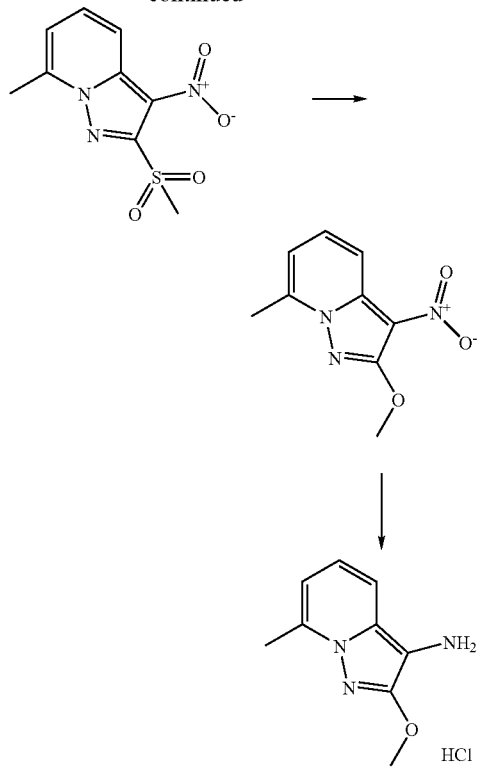

Synthesis of 1-amino-2-methylpyridinium iodide

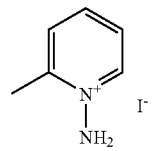

400 ml of water and 100 g of picoline were put in a 2-liter three-necked flask equipped with a bulb condenser, a thermometer, a magnetic stirrer and a dropping funnel and, at 30° C., then quickly the solution of 40.1 g of hydroxylaminosulphonic acid in 600 ml of water was added, and the mixture was heated at 85° C. for 6 hours, and then stirring was maintained at room temperature overnight.

After the addition of 69.3 g of potassium carbonate, 4×500 ml of ethyl acetate were extracted and the aqueous phase was evaporated. The solid that formed was taken up in 1.5 liter of ethanol.

After removal of the salts, the liquor was acidified at −60° C. with 47.3 ml of hydriodic acid.

Stirring was continued for 1 hour, and the solid was precipitated with 400 ml of isopropyl ether. The solid that formed was taken up in petroleum ether, drained on a frit and then washed with petroleum ether.

After drying under vacuum in the presence of $P_2O_5$, 37.6 g of a chestnut-brown solid corresponding to the expected compound was recovered.

NMR analyses ($^1$H 400 MHz and $^{13}$C 100.61 MHz DMSO $d_6$) and mass spectrophotometry were consistent with the expected structure.

Synthesis of 7-methyl-2-(methylsulphanyl)-3-nitro-pyrazolo[1,5-a]pyridine

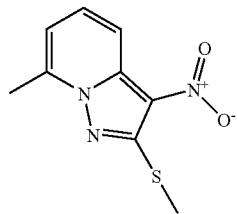

200 ml of DMF, 400 ml of ethanol, 34 g of 1,1-amino-2-methylpyridinium iodide, and 32 ml of triethylamine were put in a 500 ml three-necked flask equipped with a bulb condenser, a thermometer, a magnetic stirrer, and a dropping funnel, and stirred for 30 minutes.

The solution of 25.9 g of 1,1-bis(methylthio)-2-nitroethylene in 200 ml of DMF was added, and the reaction mixture was refluxed for 24 hours.

After cooling to room temperature, the reaction mixture was poured onto 4 liters of ice-water mixture.

The chestnut-brown insoluble product that formed was drained on a frit, washed with water and acetone, and after drying under vacuum in the presence of $P_2O_5$, 15.9 g of an ochre-brown solid corresponding to the expected compound was recovered.

NMR analyses ($^1$H 400 MHz and $^{13}$C 100.61 MHz DMSO $d_6$) and mass spectrometry were consistent with the expected structure.

Synthesis of 7-methyl-2-(methylsulphonyl)-3-nitro-pyrazolo[1,5-a]pyridine

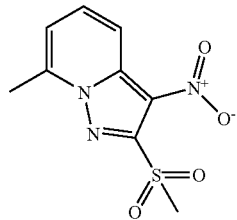

400 ml of dichloromethane and 3.2 g of 7-methyl-2-(methylsulphanyl)-3-nitropyrazolo[1,5-a]pyridine were put in a 1 L three-necked flask equipped with a bulb condenser, a thermometer and a magnetic stirrer and a dropping funnel, then, at 10° C., added dropwise was a solution of 13.2 g of meta-chloroperbenzoic acid in 250 ml of dichloromethane over 2 hours.

Stirring was maintained for several hours and the reaction mixture recovered was washed with 2×500 ml of saturated solution of sodium hydrogencarbonate and then 500 ml water.

The organic phase was washed several times with water and after drying over sodium sulphate the organic phase was evaporated to dryness, then after drying at 35° C. under vacuum in the presence of $P_2O_5$ for 12 hours, 2.33 g of a dull yellow solid corresponding to the expected compound was obtained.

NMR analyses ($^1$H 400 MHz and $^{13}$C 100.61 MHz DMSO $d_6$) and mass spectrometry were consistent with the expected structure.

Synthesis of 2-methoxy-7-methyl-3-nitropyrazolo[1,5-a]pyridine

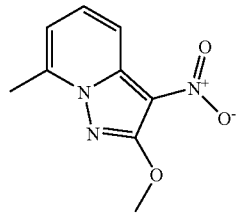

15 ml of 30% sodium methylate and 2 g of 7-methyl-2-(methylsulphonyl)-3-nitropyrazolo[1,5-a]pyridine were put in a 100 ml three-necked flask equipped with a bulb condenser, a thermometer and a magnetic stirrer.

Stirring was continued for 2 hours and the reaction mixture was poured into 500 ml of water. The pH was adjusted to 7 by adding hydrochloric acid, the compound that crystallized was drained on a frit and washed with water and then with 3×50 ml of isopropyl ether. After drying at 35° C. under vacuum in the presence of $P_2O_5$ for 12 hours, 1.62 g of a beige solid corresponding to the expected compound was recovered.

NMR analyses ($^1$H 400 MHz and $^{13}$C 100.61 MHz DMSO $d_6$) and mass spectrometry were consistent with the expected structure.

Synthesis of 2-methoxy-7-methyl-pyrazolo[1,5-a]pyridin-3-ylamine hydrochloride

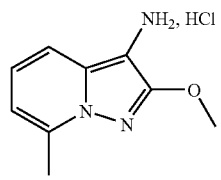

40 ml of ethanol and 4 g of zinc powder were put in a 100 ml three-necked flask equipped with a bulb condenser, a thermometer and a magnetic stirrer, and brought to reflux.

Added dropwise were 10 ml of 35% hydrochloric acid and then, in portions, 1.8 g of 2-methoxy-7-methyl-3-nitropyrazolo[1,5-a]pyridine.

At the end of addition, a few drops of hydrochloric ethanol were added and reflux was maintained for 1 hour.

At the end of reduction, the zinc was removed by filtration under argon on a bed of Celite and the filtrate was collected in a flask containing 20 ml of previously cooled 6N hydrochloric ethanol and after concentrating to 1/3, ethyl acetate was added to the residue, then evaporated to the maximum.

The residue was taken up in hydrochloric ethanol and the solid that formed was drained on a frit, then washed with 2×50 ml of isopropyl ether. After drying under vacuum in the presence of $P_2O_5$ and soda tablets, 1.2 g of a powder corresponding to the expected compound was recovered.

NMR analyses ($^1$H 400 MHz and $^{13}$C 100.61 MHz $D_2O$) were consistent with the expected structure.

Mass Analysis:

The quasi-molecular ions [M+H]⁺, [M+Na]⁺ and [M−H]⁻ of the expected molecule, $C_9H_{11}N_3O$, were mainly detected.

Example 18

4-Ethyl-2-methoxy-7-methyl-pyrazolo[1,5-a]pyridin-3-ylamine dihydrochloride

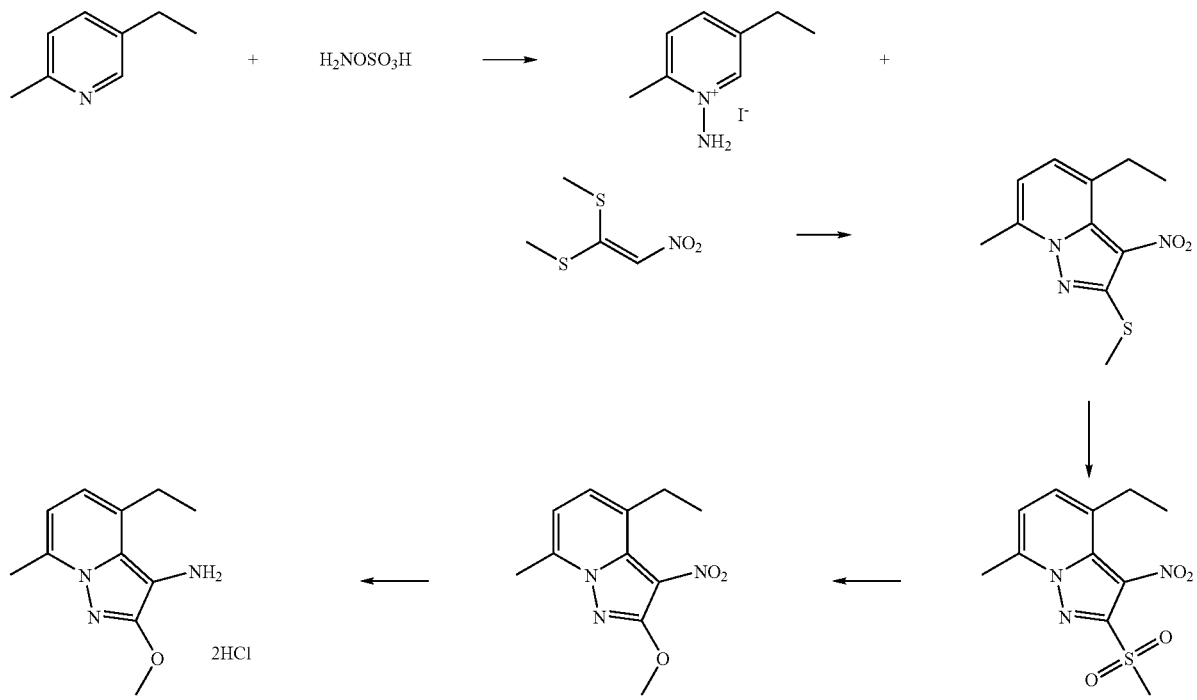

Synthesis of 1-amino-5-ethyl-2-methylpyridinium iodide

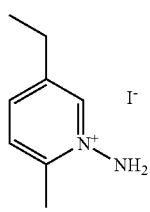

100 ml of water and 50 ml of 5-ethyl-2-methylpyridine were put in a 500 ml three-necked flask equipped with a bulb condenser, a thermometer, a magnetic stirrer and a dropping funnel and, at 30° C., a solution of 20 g of hydroxylaminosulphonic acid in 250 ml of water was quickly added and the reaction mixture was heated at 85° C. for 6 hours, then stirring was continued at room temperature overnight.

Extraction was carried out with 5×500 ml of ethyl acetate and the aqueous phase was evaporated to dryness, and the solid obtained was washed with 500 ml of ethanol.

The ethanolic liquor was put in a 1-liter three-necked flask, cooled to −40° C. and 29 ml of hydriodic acid was quickly added dropwise while stirring well.

Stirring was continues for one hour and the solid obtained was precipitated with 3 liters of isopropyl ether. The salmon-pink solid that formed was drained on a frit and then washed with isopropyl ether.

After drying under vacuum in the presence of $P_2O_5$, 15.2 g of an ochre-brown solid corresponding to the expected compound was recovered.

NMR analyses (¹H 400 MHz and ¹³C 100.61 MHz DMSO d₆) and mass spectrophotometry were consistent with the expected structure.

Synthesis of 4-ethyl-7-methyl-2-(methylsulphanyl)-3-nitropyrazolo[1,5-a]pyridine

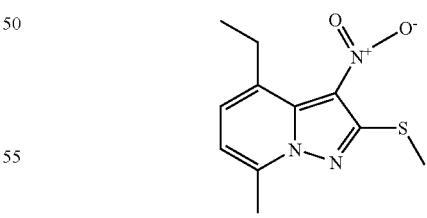

160 ml of DMF, 24.8 g of 1-amino-5-ethyl-2-methylpyridinium iodide, 39 g of potassium carbonate and 15.5 g of 1,1-bis(methylthio)-2-nitroethylene were put in a 500 ml three-necked flask equipped with a bulb condenser, a thermometer, a magnetic stirrer and a dropping funnel.

Stirring was continued for 96 hours at room temperature and the reaction mixture was then poured onto 2.5 liters of ice-water mixture.

The ochre-brown insoluble matter that formed was drained on a No. 3 frit, washed with plenty of water, with 3×50 ml of isopropanol and then with 3×500 ml of isopropyl ether.

After drying under vacuum in the presence of $P_2O_5$, 10.59 g of an ochre-brown solid corresponding to the expected compound was recovered.

NMR analyses ($^1$H 400 MHz and $^{13}$C 100.61 MHz DMSO $d_6$) and mass spectrophotometry were consistent with the expected structure. The quasi-molecular ions [M+H]$^+$, [M+Na]$^+$, [M+Na+CH$_3$OH]$^+$, [2M+Na]$^+$ were mainly detected.

Synthesis of 4-ethyl-7-methyl-2-(methylsulphonyl)-3-nitropyrazolo[1,5-a]pyridine

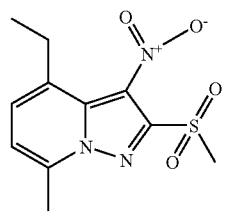

100 ml of dichloromethane and 10 g of 4-ethyl-7-methyl-2-(methylsulphanyl)-3-nitropyrazolo[1,5-a]pyridine were put in a 1 L three-necked flask equipped with a bulb condenser, a thermometer, a magnetic stirrer and a dropping funnel then, at 10° C., a solution of 39.2 g of meta-chloroperbenzoic acid in 600 ml of dichloromethane was added dropwise in 2 hours.

Stirring was continued for one more hour and the reaction mixture was washed with 4×500 ml of saturated solution of sodium hydrogencarbonate and then 500 ml of water.

After drying, the organic phase was evaporated to dryness, and the yellow compound that formed was taken up in isopropyl ether.

The solid was drained on a frit, washed with water and then with 3×50 ml of isopropyl ether. After drying at 35° C. under vacuum in the presence of $P_2O_5$ for 12 hours, a yellow solid corresponding to the expected compound was recovered.

NMR analyses ($^1$H 400 MHz and $^{13}$C 100.61 MHz DMSO $d_6$) and mass spectrophotometry were consistent with the expected structure.

The quasi-molecular ions [M+H]$^+$, [M+Na]$^+$, [M+Na+CH$_3$OH]$^+$, [2M+Na]$^+$ were mainly detected.

Synthesis of 4-ethyl-2-methoxy-7-methyl-3-nitropyrazolo[1,5-a]pyridine

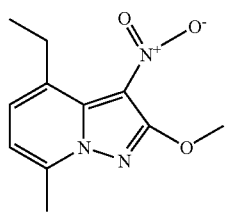

30 ml of 30% sodium methylate and 4 g of 4-ethyl-7-methyl-2-(methylsulphonyl)-3-nitropyrazolo[1,5-a]pyridine in 30 ml of methanol were put in a 100 ml three-necked flask equipped with a bulb condenser, a thermometer and a magnetic stirrer, and stirred for 2 hours.

The reaction mixture was poured onto 500 ml of water, the compound that crystallized was drained on a frit, and washed with water and then with 3×50 ml of isopropyl ether. After drying at 35° C. under vacuum in the presence of $P_2O_5$ for 12 hours, 1.2 g of a beige solid corresponding to the expected compound was recovered.

NMR analyses ($^1$H 400 MHz and $^{13}$C 100.61 MHz DMSO $d_6$) and mass spectrophotometry were consistent with the expected structure.

The quasi-molecular ions [M+H]$^+$, [M+Na]$^+$, [M+Na+CH$_3$OH]$^+$, [2M+Na]$^+$ were mainly detected.

Synthesis of 4-ethyl-2-methoxy-7-methyl-pyrazolo[1,5-a]pyridin-3-ylamine dihydrochloride

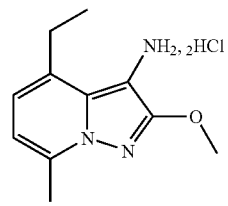

50 ml of ethanol and 4.5 g of zinc powder were put in a 100 ml three-necked flask equipped with a bulb condenser, a thermometer and a magnetic stirrer, and brought to reflux.

Next, 175 mg of ammonium chloride were added and then, in portions, 620 mg of 4-ethyl-2-methoxy-7-methyl-3-nitropyrazolo[1,5-a]pyridine. At the end of addition, 10 ml of hydrochloric ethanol were added dropwise and reflux was maintained for 1 hour.

At the end of reduction, the zinc was removed by filtration under argon on a bed of Celite and the filtrate was collected in a flask containing 20 ml of previously cooled 6N hydrochloric ethanol and after concentrating to 1/3, the liquor was diluted with 400 ml of isopropyl ether.

Precipitation of a sticky solid was observed; this was taken up in isopropyl ether. Once it crystallized, the solid was drained on a frit and then washed with 2×50 ml of isopropyl ether. After drying under vacuum in the presence of $P_2O_5$ and soda tablets, 1.5 g of a powder corresponding to the expected compound was recovered.

NMR analyses ($^1$H 400 MHz and $^{13}$C 100.61 MHz DMSO $d_6$) were consistent with the expected structure.

The quasi-molecular ions [M+H]$^+$, [M+Na]$^+$ and [M−H]$^−$ of the expected molecule, $C_{11}H_{15}N_3O$, were mainly detected.

Example 19

4-ethyl-7-methyl-2-pyrrolidin-1-yl-pyrazolo[1,5-a]pyridin-3-ylamine dihydrochloride

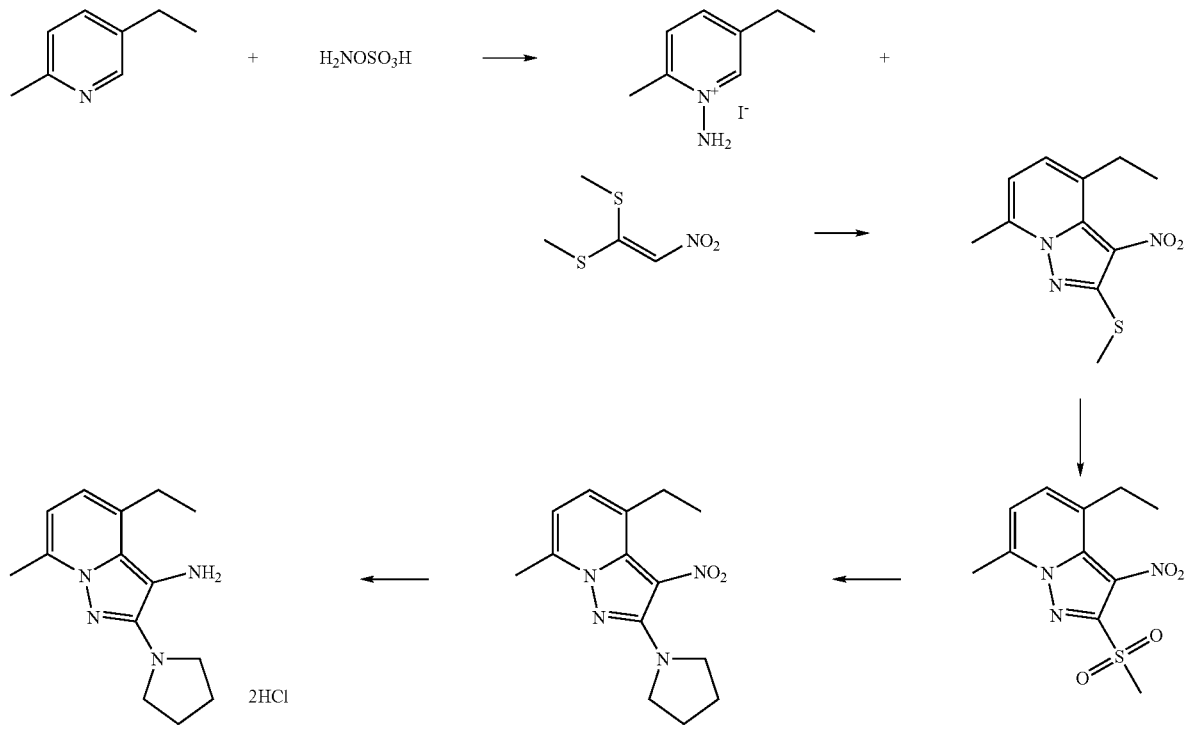

Synthesis of 4-ethyl-7-methyl-3-nitro-2-pyrrolidin-1-ylpyrazolo[1,5-a]pyridine

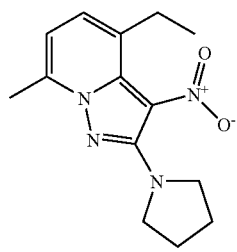

25 ml of pyrrolidine and 1.5 g of 4-ethyl-7-methyl-2-(methylsulphanyl)-3-nitropyrazolo[1,5-a]pyridine were put in a 50 ml three-necked flask equipped with a bulb condenser, a thermometer and a magnetic stirrer; this mixture was stirred for 1 hour.

The yellow compound was drained, isolated by pouring the reaction mixture into ice water, on a frit and then washed with water several times and with petroleum ether. After drying under vacuum in the presence of $P_2O_5$, 0.651 g of a yellow solid corresponding to the expected compound was recovered.

NMR analyses ($^1$H 400 MHz and $^{13}$C 100.61 MHz DMSO $d_6$) were consistent with the expected structure.

Synthesis of 4-ethyl-7-methyl-2-pyrrolidin-1-ylpyrazolo[1,5-a]pyridin-3-ylamine dihydrochloride

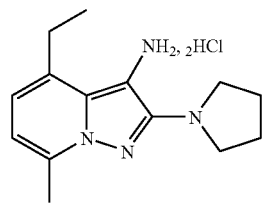

30 ml of ethanol and 1.6 g of zinc powder were put in a 50 ml three-necked flask equipped with a bulb condenser, a thermometer and a magnetic stirrer, and brought to reflux.

Then 60 mg of ammonium chloride were added, then, in portions, 620 mg of 4-ethyl-7-methyl-3-nitro-2-pyrrolidin-1-ylpyrazolo[1,5-a]pyridine.

At the end of addition, 5 ml of hydrochloric ethanol were added dropwise and reflux was maintained for 2 hours.

At the end of reduction, the zinc was removed by filtration under argon on a bed of Celite and the filtrate was collected in a flask containing 20 ml of previously cooled 6N hydrochloric ethanol, and isopropyl ether was added to this filtrate.

Precipitation of a yellowish solid was then observed. This was drained on a frit and washed with 2×50 ml of isopropyl ether. After drying under vacuum in the presence of $P_2O_5$ and soda tablets, 623 mg of a greyish-beige powder corresponding to the expected compound was recovered.

NMR analyses ($^1$H 400 MHz and $^{13}$C 100.61 MHz D$_2$O) were consistent with the expected structure.

The quasi-molecular ions [M+H]$^+$, [M+Na]$^+$ and [M−H]$^-$ of the expected molecule, C$_{14}$H$_{20}$N$_4$, were mainly detected.

Example 20

2-Methylsulphanyl-pyrazolo[1,5-a]pyridin-3-ylamine hydrochloride

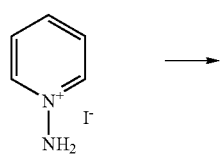

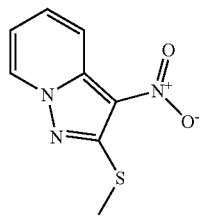

Synthesis of
2-methylsulphanyl-pyrazolo[1,5-a]pyridin-3-ylamine hydrochloride

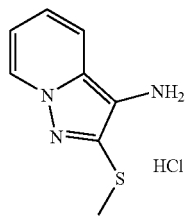

200 ml of ethanol and 15 g of zinc powder were put in a 500 ml three-necked flask equipped with a bulb condenser, a thermometer and a magnetic stirrer, and brought to reflux.

Then added dropwise were 5 ml of hydrochloric acid, then, in portions, 5 g of 2-(methylsulphanyl)-3-nitropyrazolo[1,5-a]pyridine in 45 minutes. At the end of addition, 5 ml of hydrochloric acid was added dropwise and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a beige solid was observed. This was drained on a frit and was then washed with 2×50 ml of isopropyl ether. After drying under vacuum in the presence of P$_2$O$_5$ and soda tablets, 4.9 g of a greyish-beige powder corresponding to the expected compound was recovered.

NMR analyses ($^1$H 400 MHz and $^{13}$C 100.61 MHz DMSO d$_6$) were consistent with the expected structure.

The quasi-molecular ions [M+H]$^+$, [M+Na]$^+$ and [M−H]$^-$ of the expected molecule, C$_8$H$_9$N$_3$S, were mainly detected.

Example 21

6,7-Dimethyl-2-methylsulphanyl-pyrazolo[1,5-a]pyridin-3-ylamine dihydrochloride

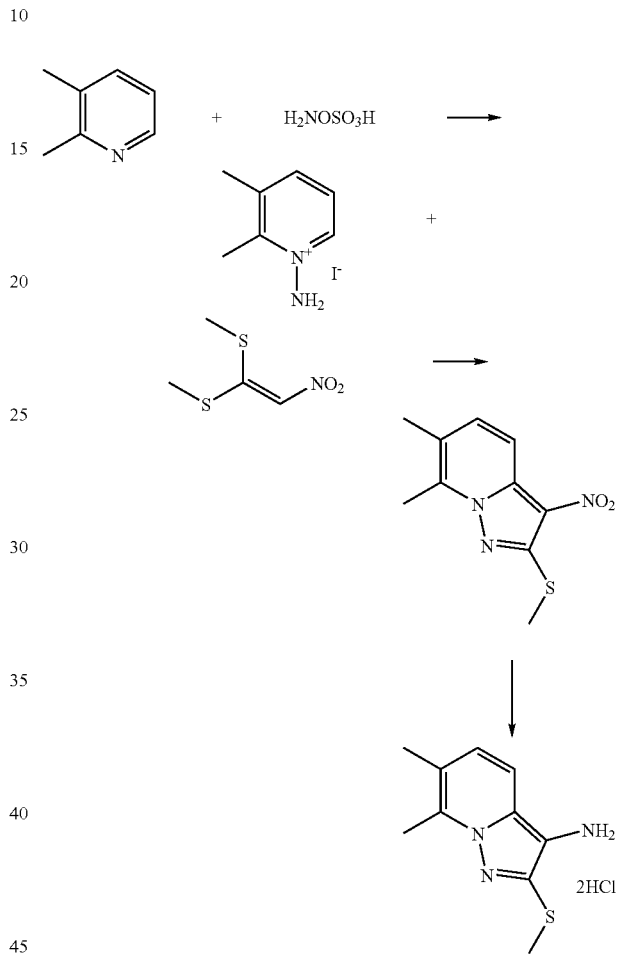

Synthesis of 1-amino-2,3-dimethylpyridinium iodide

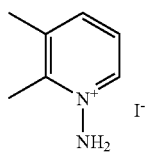

400 ml of water and 64.2 g of 2,3-dimethylpyridine were put in a 1-liter three-necked flask, heated to 30° C. then 122.6 g of hydroxylamine-o-sulphonic acid were added.

At the end of addition, the reaction mixture was heated at 90° C. for 7 hours. After cooling to room temperature, 28 g of potassium carbonate were added in portions in an hour, with stirring.

Then the aqueous solution was washed with 5×300 ml of ethyl acetate and the residue was taken up in 200 ml of ethanol, the solid obtained was filtered and 56.9 g of 45% hydriodic acid was added dropwise to the filtrate cooled to −60° C.

Stirring was continued for two hours and the solid that formed was drained on a No. 3 frit. After drying under vacuum in the presence of $P_2O_5$, 31.5 g of 1-amino-2,3-dimethylpyridinium iodide corresponding to the expected compound was recovered.

$^1$H-NMR (200 MHz, $CDCl_3$), ☐ 8.06 (d, 1H), 7.46 (d, 1H), 2.76 (s, 3H), 2.67 (s, 3H), 2.43 (s, 3H)

Synthesis of 6,7-dimethyl-2-(methylsulphanyl)-3-nitropyrazolo[1,5-a]pyridine

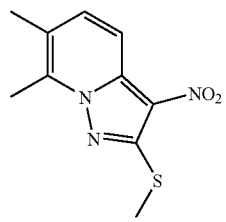

19.1 g of triethylamine was added dropwise to a 1-liter round-bottomed flask containing 800 ml of anhydrous ethanol, 31.5 g of 1-amino-2,3-dimethylpyridinium iodide and 20.8 g of 1,1-bis(methylthio)-2-nitroethylene.

The reaction mixture was refluxed for 3 hours and then cooled to a temperature below 10° C. The solid that formed was drained while stirring, washed with ethanol, and after drying under vacuum in the presence of $P_2O_5$, 8.32 g of 6,7-dimethyl-2-(methylsulphanyl)-3-nitropyrazolo[1,5-a]pyridine corresponding to the expected compound was recovered.

NMR analyses ($^1$H 400 MHz and $^{13}$C 100.61 MHz DMSO $d_6$) and mass spectrometry were consistent with the expected structure.

Synthesis of 6,7-dimethyl-2-methylsulphanyl-pyrazolo[1,5-a]pyridin-3-ylamine dihydrochloride

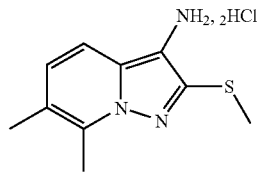

100 ml of ethanol and 10 g of zinc powder were put in a 250 ml three-necked flask equipped with a bulb condenser, a thermometer and a magnetic stirrer, and brought to reflux.

Then added dropwise was 1 ml of 35% hydrochloric acid and then, in portions, 4 g of 6,7-dimethyl-2-(methylsulphanyl)-3-nitropyrazolo[1,5-a]pyridine.

At the end of addition, reflux was maintained for 2 hours. At the end of reduction, the zinc was removed by filtration under argon on a bed of Celite and the filtrate was collected in a flask containing 50 ml of previously cooled 6N hydrochloric isopropanol.

The filtrate was concentrated to 1/3 of volume; and crystallization of a grey solid was observed. This was drained on a frit and then washed with 2×100 ml of isopropyl ether. After drying under vacuum in the presence of $P_2O_5$ and soda tablets, 3.6 g of a grey powder corresponding to the expected compound was recovered.

NMR analyses ($^1$H 400 MHz and $^{13}$C 100.61 MHz DMSO $d_6$) were consistent with the expected structure.

The quasi-molecular ions $[M+H]^+$, $[M+Na]^+$ and $[M-H]^-$ of the expected molecule, $C_{10}H_{13}N_3S$, were mainly detected.

Example 22

N-2-[2-(dimethylamino)ethyl]-6,7-dimethyl pyrazolo[1,5-a]pyridine-2,3-diamine dihydrochloride

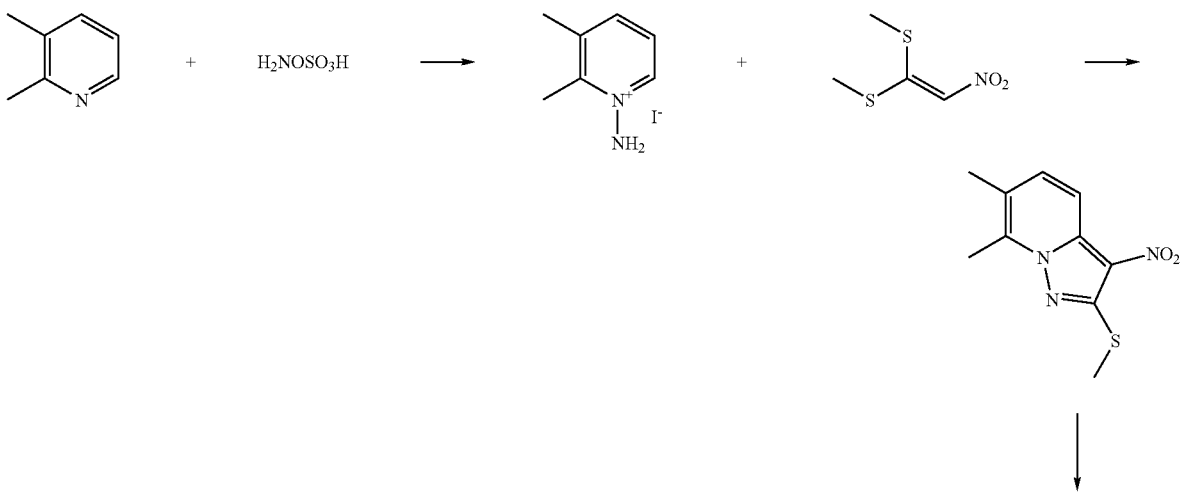

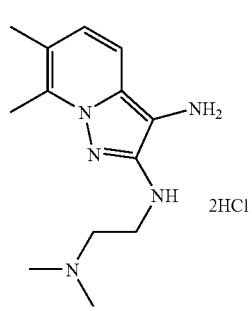 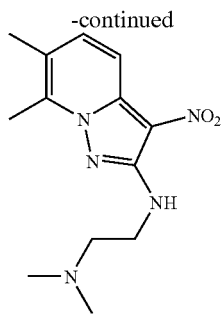 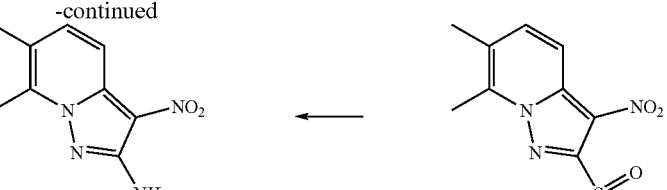

Synthesis of N-2-[2-(dimethylamino)ethyl]-6,7-dimethyl pyrazolo[1,5-a]pyridine-2,3-diamine dihydrochloride

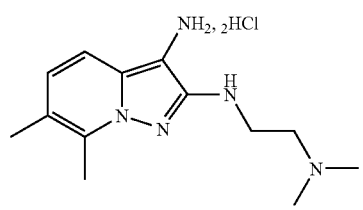

200 ml of ethanol and 5 g of zinc powder were put in a 500 ml three-necked flask equipped with a bulb condenser, a thermometer and a magnetic stirrer, and brought to reflux.

Then added dropwise was 1 ml of acid acetic and then, in portions, 4 g of N'-(6,7-dimethyl-3-nitropyrazolo[1,5-a]pyridin-2-yl)-N,N-dimethylethane-1,2-diamine, while regularly adding acetic acid (to a total of 1.5 ml).

At the end of addition, reflux was maintained for 2 hours. At the end of reduction, the zinc was removed by filtration under argon on a bed of Celite and the filtrate was collected in a flask containing 100 ml of previously cooled 6N hydrochloric isopropanol.

A white solid crystallized; it was drained on a frit and then washed with 2×100 ml of isopropyl ether. After drying under vacuum in the presence of $P_2O_5$ and soda tablets, 4.5 g of a white powder corresponding to the expected compound was recovered.

NMR analyses ($^1H$ 400 MHz and $^{13}C$ 100.61 MHz DMSO $d_6$) and mass spectrometry were consistent with the expected structure.

Example 22

2-methoxy-6,7-dimethyl pyrazolo[1,5-a]pyridin-3-amine hydrochloride

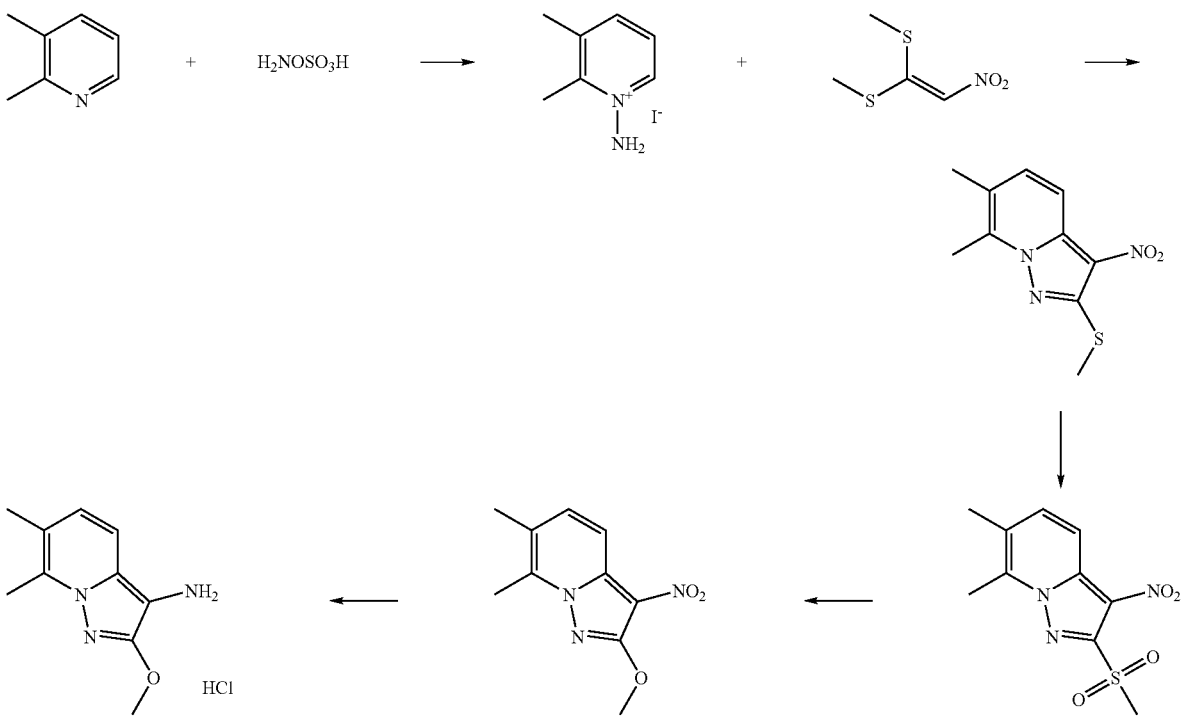

Synthesis of 2-methoxy-6,7-dimethyl pyrazolo[1,5-a]pyridin-3-amine hydrochloride

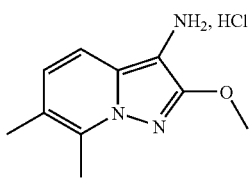

100 ml of ethanol and 1.5 g of zinc powder were put in a 250 ml three-necked flask equipped with a bulb condenser, a thermometer and a magnetic stirrer, and brought to reflux.

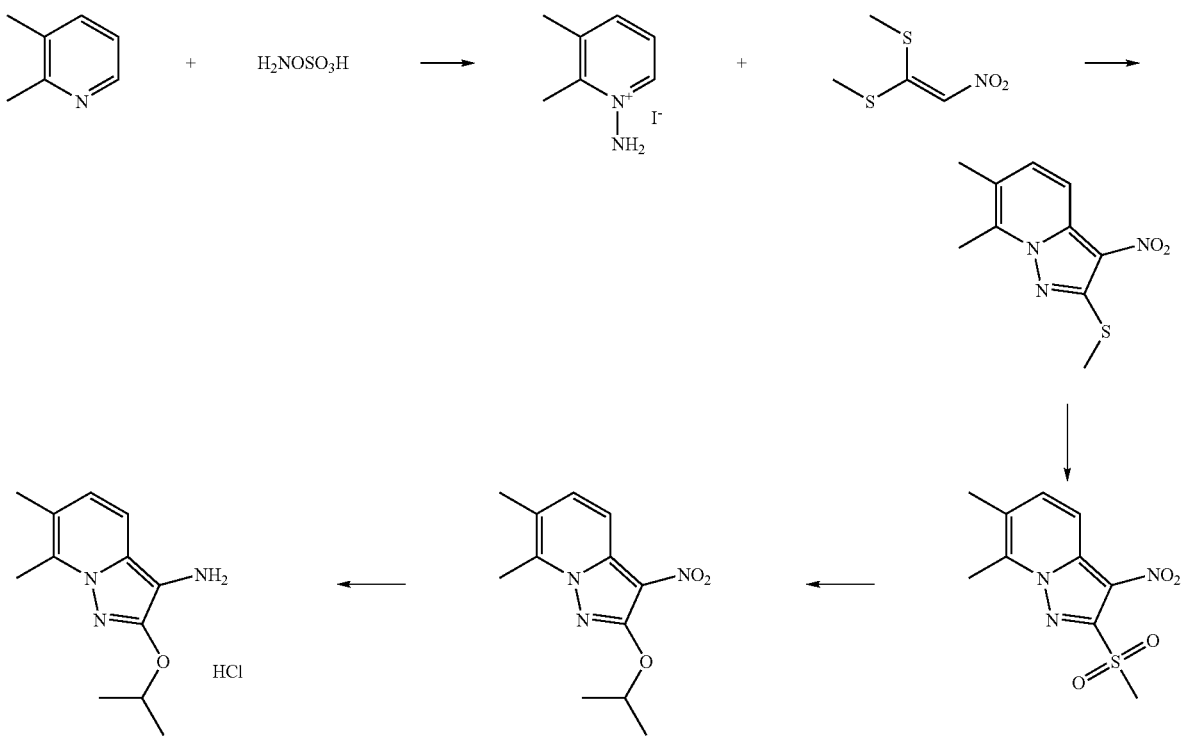

Then 3 drops of acetic acid were added and then, in portions, 1.5 g of 2-methoxy-6,7-dimethyl-3-nitropyrazolo[1,5-a]pyridine while regularly adding a few drops of acetic acid.

At the end of addition, reflux was maintained for 20 minutes. At the end of reduction, the zinc was removed by filtration under argon on a bed of Celite and the filtrate was collected in a flask containing 20 ml of previously cooled 6N hydrochloric isopropanol.

After evaporating the solution to ¹/₁₀, crystallization was started and abundant beige solid crystallized on adding 50 ml of a mixture of isopropanol and ether.

The solid was drained on a frit and then washed with 2×30 ml of ether. After drying under vacuum in the presence of $P_2O_5$ and soda tablets, 700 mg of a white powder corresponding to the expected compound was recovered.

NMR analyses ($^1$H 400 MHz and $^{13}$C 100.61 MHz DMSO $d_6$) and mass spectrometry were consistent with the expected structure.

Example 23

2-isopropoxy-6,7-dimethyl pyrazolo[1,5-a]pyridin-3-amine hydrochloride

Synthesis of 2-isopropoxy-6,7-dimethyl pyrazolo[1,5-a]pyridin-3-amine hydrochloride

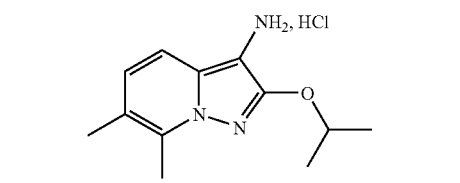

100 ml of ethanol and 1.5 g of zinc powder were put in a 250 ml three-necked flask equipped with a bulb condenser, a thermometer and a magnetic stirrer, and brought to reflux.

Then 0.25 ml of acetic acid were added and then, in portions, 1.5 g of 2-isopropoxy-6,7-dimethyl-3-nitropyrazolo[1,5-a]pyridine while regularly adding a few drops of acetic acid.

At the end of addition, reflux was maintained for 1 hour. At the end of reduction, the zinc was removed by filtration under argon on a bed of Celite and the filtrate was collected in a flask containing 20 ml of previously cooled 6N hydrochloric isopropanol.

After evaporating the solution to 1/10, 50 ml of heptane was added and the solution was concentrated again to 1/10 of volume; then taken up in 50 ml of ether to start crystallization. The solid that formed was drained on a frit. After drying under vacuum in the presence of $P_2O_5$ and soda tablets, 560 mg of a slightly pink beige powder corresponding to the expected compound was recovered.

NMR analyses ($^1$H 400 MHz and $^{13}$C 100.61 MHz DMSO $d_6$) and mass spectrometry were consistent with the expected structure.

Example 24

N-5,N-5-dimethyl-2-methylsulphanyl-pyrazolo[1,5-a]pyridine-3,4-diamine dihydrochloride Synthesis of N-5,N-5-dimethyl-2-methylsulphanyl-pyrazolo[1,5-a]pyridine-3,4-diamine dihydrochloride

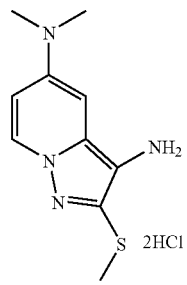

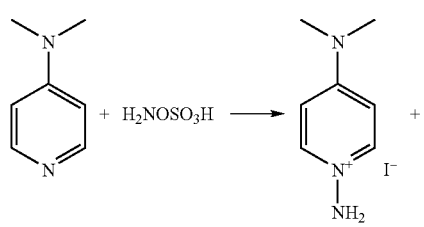

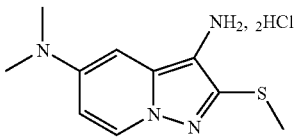

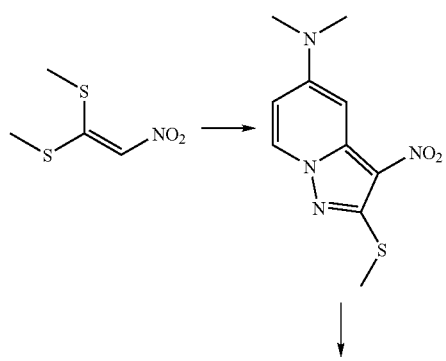

100 ml of ethanol and 6 g of zinc powder were put in a 250 ml three-necked flask equipped with a bulb condenser, a thermometer and a magnetic stirrer, and brought to reflux.

Then added dropwise was 1 ml of hydrochloric acid and then, in portions, 2.36 g of N,N-dimethyl-2-(methylsulphanyl)-3-nitropyrazolo[1,5-a]pyridin-5-amine.

At the end of addition, reflux was maintained for 2 hours. At the end of reduction, the zinc was removed by filtration under argon on a bed of Celite and the filtrate was collected in a flask containing 50 ml of previously cooled 6N hydrochloric isopropanol.

The liquor was concentrated to 1/8 of volume; and crystallization of a beige solid was observed. This was taken up in hydrochloric isopropanol. The solid that formed was drained on a frit and then wash with 2×100 ml of isopropyl ether. After drying under vacuum in the presence of $P_2O_5$ and soda tablets, 2.4 g of a grey powder corresponding to the expected compound was recovered.

NMR analyses ($^1$H 400 MHz and $^{13}$C 100.61 MHz DMSO $d_6$) and mass spectrometry were consistent with the expected structure.

Example 25

N-2-[2-(dimethylamino)ethyl]-7,8-dihydro-6H-cyclopenta[e]pyrazolo[1,5-a]pyridine-2,3-diamine

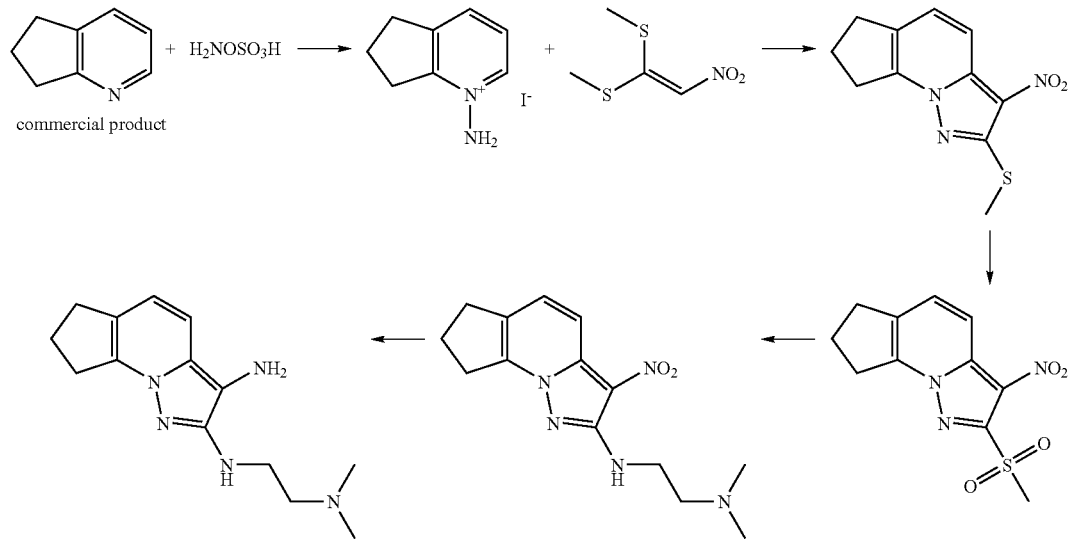

Synthesis of 1-amino-6,7-dihydro-5H-cyclopenta[b]pyridinium iodide

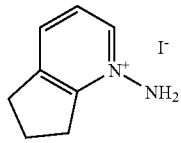

400 ml of water and 123 g (1.032 mol) of 2,3-cyclopentenopyridine were put in a 1000 ml three-necked flask equipped with a bulb condenser, a thermometer and a mechanical stirrer, then 46.6 g (0.413 mol) of hydroxylamine-o-sulphonic acid was added in small portions and reflux was carried out for 18 hours.

The reaction mixture was cooled to room temperature and 74.2 g (0.537 mol) of potassium carbonate was gently added, then stirred for 30 minutes.

The aqueous phase was washed with 4×200 ml of ethyl acetate, then co-evaporated with 2-propanol to obtain a chestnut-brown solid; this was taken up in 400 ml of ethanol to remove the salts.

The brown ethanol solution was put in a 2-liter three-necked flask equipped with an isobaric funnel and cooled to −50° C. with stirring. Then added, dropwise, were 67.5 ml (0.516 mol) of hydriodic acid.

At the end of addition, the temperature was returned to zero degrees and the beige insoluble matter was drained on a frit. This solid was washed with 3×150 ml of isopropyl ether. After drying under vacuum in the presence of $P_2O_5$ for 12 hours, 27.7 g of a beige solid corresponding to the expected compound was recovered.

NMR analyses ($^1H$ 400 MHz and $^{13}C$ 100.61 MHz DMSO $d_6$) and mass spectrometry were consistent with the expected structure.

The expected cation $[C_8H_{11}N_2]^+$ was mainly detected at m/z, ESP+=135. Detection of I⁻ ions in electrospray was negative.

Synthesis of 2-(methylsulphanyl)-3-nitro-7,8-dihydro-6H-cyclopenta[e]pyrazolo[1,5-a]pyridine

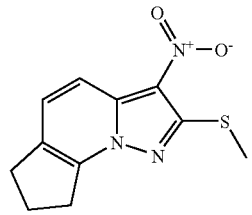

500 ml of N-methylpyrrolidinone and 65.56 g (0.025 mol) of 1-amino-6,7-dihydro-5H-cyclopenta[b]pyridinium iodide were put in a 2-liter three-necked flask equipped with a bubbler, a condenser and a mechanical stirrer. Gently added, while stirring, were 103.65 g of potassium carbonate in 15 minutes and then, in one go, 41.33 g (0.25 mol) of 1,1-bis(methythio)-2-nitroethylene.

Stirring was continued for 48 hours at room temperature and the reaction mixture was poured onto 2.5 liters of ice-water mixture.

The dark green insoluble that formed was drained on a No. 3 frit and then washed with plenty of water, 3×200 ml of ethyl acetate and then with 3×200 ml of isopropyl ether.

After drying under vacuum in the presence of $P_2O_5$, 36.77 g of a dark green solid corresponding to the expected compound was recovered.

NMR analyses (¹H 400 MHz and ¹³C 100.61 MHz DMSO d₆) and mass spectrometry were consistent with the expected structure.

The quasi-molecular ions [M+H]⁺, [M+Na]⁺, [2M+Na]⁺ of the expected molecule $C_{11}H_{11}N_3O_2S$ were mainly detected.

Synthesis of 2-(methylsulphonyl)-3-nitro-7,8-dihydro-6H-cyclopenta[e]pyrazolo[1,5-a]pyridine

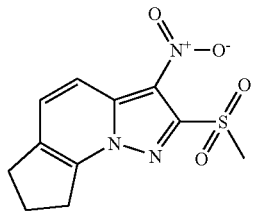

267.6 g of Oxone (3 eq.), 800 ml of water and 36.17 g of 2-(methylsulphanyl)-3-nitro-7,8-dihydro-6H-cyclopenta[e]pyrazolo[1,5-a]pyridine (0.145 mol) obtained previously, were put, successively, in a 3-liter three-necked flask equipped with a mechanical stirrer and an internal temperature sensor. The whole was stirred at room temperature.

To complete the reaction, Oxone (89.2 g, 1 eq.) was added and after 4 hours with stirring at room temperature, the reaction stopped.

The solid that formed was washed with plenty of water until a filtrate was obtained that no longer contained peroxides. Then it was put under vacuum at 40° C. over P₂O₅.

35.31 g of the expected product was obtained (yellow solid).

NMR analyses (¹H 400 MHz and ¹³C 100.61 MHz DMSO d₆) and mass spectrometry were consistent with the expected structure.

The quasi-molecular ions [M−H]⁻, [M+H]⁺, [M+Na]⁺, [M+Na+CH₃OH]⁺, [2M+Na]⁺ of the expected molecule $C_{11}H_{11}N_3O_4S$ were mainly detected.

Synthesis of N,N-dimethyl-N'-(3-nitro-7,8-dihydro-6H-cyclopenta[e]pyrazolo[1,5-a]pyridin-2-yl)ethane-1,2-diamine

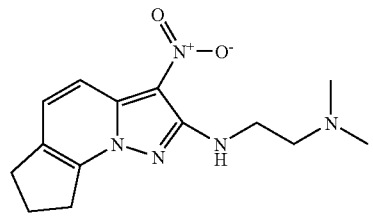

50 ml of N-methylpyrrolidinone, 10 g (0.03555 mol) of 2-(methylsulphonyl)-3-nitro-7,8-dihydro-6H-cyclopenta[e]pyrazolo[1,5-a]pyridine and 7.8 ml of N,N-dimethylethylene diamine were put in a 250 ml three-necked flask equipped with a bulb condenser, a thermometer and a magnetic stirrer, and heated at 70° C. on an oil bath for 4 hours.

The reaction mixture was cooled to room temperature and then poured onto a mixture of 200 g of ice and water. The yellow compound that has crystallized was drained on a frit, washed with 2×100 ml of water and then with 3×100 ml of isopropyl ether. After drying at 35° C. under vacuum in the presence of P₂O₅, for 12 hours, 8.32 g of a green solid corresponding to the expected compound was recovered.

NMR analyses (¹H 400 MHz and ¹³C 100.61 MHz DMSO d₆) and mass spectrophotometry were consistent with the expected structure. The quasi-molecular ions of the expected molecule $C_{14}H_{19}N_5O_2$ were mainly detected.

Synthesis of N-2-[2-(dimethylamino)ethyl]-7,8-dihydro-6H-cyclopenta[e]pyrazolo[1,5-a]pyridine-2,3-diamine dihydrochloride

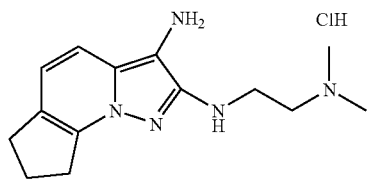

150 ml of ethanol and 2 g of zinc powder were put in a 250 ml three-necked flask equipped with a bulb condenser, a thermometer and a magnetic stirrer, and brought to reflux.

Then added dropwise were 2 ml of acid acetic and then a solution of 5 ml of water and 2 g of N,N-dimethyl-N'-(3-nitro-7,8-dihydro-6H-cyclopenta[e]pyrazolo[1,5-a]pyridin-2-yl)ethane-1,2-diamine.

At the end of discharge, 1 ml of acetic acid was added dropwise and reflux was maintained for 2 hours. At the end of reduction, the zinc was removed by filtration under argon on a bed of Celite and the filtrate was collected in a flask containing 50 ml of previously cooled 6N hydrochloric isopropanol.

Precipitation of a greyish-blue solid was observed. This was drained on a No. 3 frit and washed with 2×15 ml of ethanol and 2×50 ml of isopropyl ether. After drying under vacuum in the presence of P₂O₅ and soda tablets, 1.92 g of a bluish-green powder corresponding to the expected compound was recovered.

NMR analyses (¹H 400 MHz and ¹³C 100.61 MHz DMSO d₆) and mass spectrophotometry were consistent with the expected structure.

The quasi-molecular ion [M+H]⁺ of the expected molecule $C_{14}H_{21}N_5$ was mainly detected.

Example 26

2-[(3-amino-7,8-dihydro-6H-cyclopenta[e]pyrazolo[1,5-a]pyridin-2-yl)amino]ethanol hydrochloride

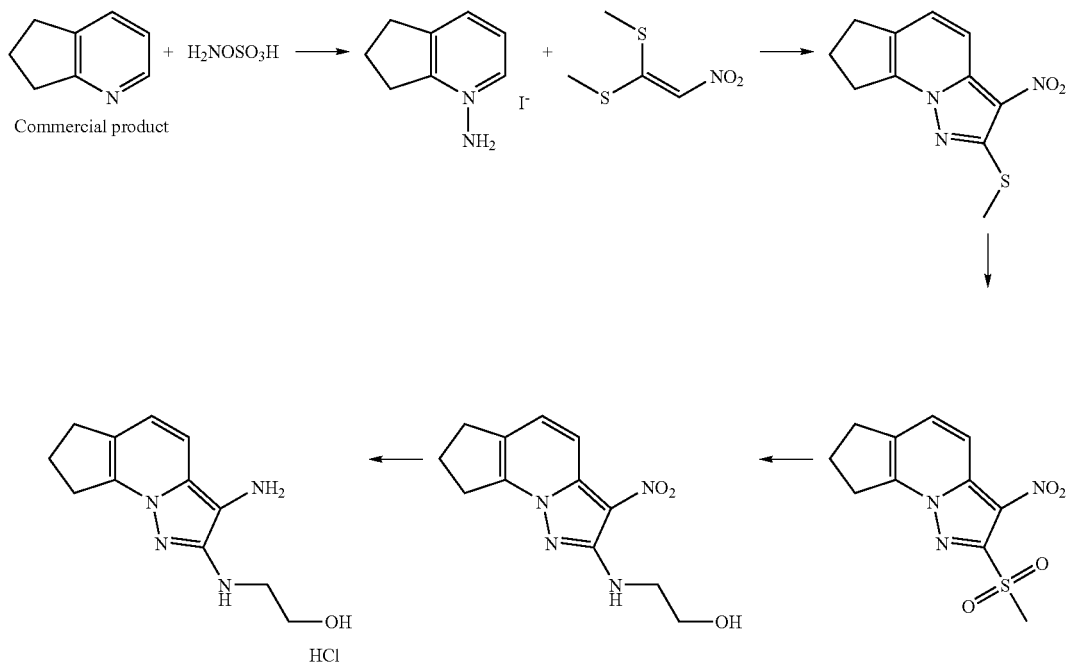

Synthesis of 2-[(3-nitro-7,8-dihydro-6H-cyclopenta[e]pyrazolo[1,5-a]pyridin-2-yl)amino]ethanol

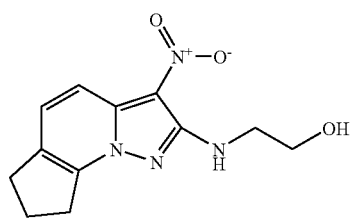

50 ml of N-methylpyrrolidinone, 10 g (0,03555 mol) of 2-(methylsulphonyl)-3-nitro-7,8-dihydro-6H-cyclopenta[e]pyrazolo[1,5-a]pyridine and 4.29 ml of ethanolamine were put in a 250 ml three-necked flask equipped with a bulb condenser, a thermometer and a magnetic stirrer, and heated at 70° C. on an oil bath for 5 hours.

The reaction mixture was cooled to room temperature and then poured onto a mixture of 200 g of ice and water. The yellow compound that crystallized was formed on a No. 3 frit, washed with water 2×100 ml and then with 3×100 ml of isopropyl ether. After drying at 35° C. under vacuum in the presence of $P_2O_5$ for 12 hours, 8.70 g of a green solid corresponding to the expected compound was recovered.

NMR analyses ($^1$H 400 MHz and $^{13}$C 100.61 MHz DMSO $d_6$) and mass spectrophotometry were consistent with the expected structure.

The quasi-molecular ions [M+H]$^+$, [M+Na]$^+$, [M+Na+CH$_3$OH]$^+$, [M+Na+CH$_3$CN]$^+$, [2M+Na]$^+$, [M−H]$^−$ of the expected molecule $C_{12}H_{14}N_4O_3$ were mainly detected.

Synthesis of 2-[(3-amino-7,8-dihydro-6H-cyclopenta[e]pyrazolo[1,5-a]pyridin-2-yl)amino]ethanol hydrochloride

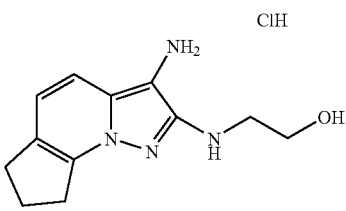

50 ml of ethanol and 2 g of zinc powder were put in a 100 ml three-necked flask equipped with a bulb condenser, a thermometer and a magnetic stirrer, and brought to reflux.

Then added dropwise were 2 ml of acid acetic then, in portions, 1 g of 2-[(3-nitro-7,8-dihydro-6H-cyclopenta[e]pyrazolo[1,5-a]pyridin-2-yl)amino]ethanol. At the end of discharge, 1 ml of acid acetic was added dropwise and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a greyish-blue solid was observed. This was drained on a No. 3 frit and then washed with 2×15 ml of ethanol and 2×50 ml of isopropyl ether. After drying under vacuum in the presence of $P_2O_5$ and soda tablets, 0.96 g of a bluish-green powder corresponding to the expected compound was recovered.

NMR analyses ($^1$H 400 MHz and $^{13}$C 100.61 MHz DMSO $d_6$) and mass spectrophotometry were consistent with the expected structure.

The quasi-molecular ions $[M+H]^+$, $[M+Na]^+$, $[M+H+CH_3OH]^+$, $[M-H]^-$, $[M+Cl]^-$ of the expected molecule $C_{12}H_{16}N_4O$ were detected.

Example 27

2-methoxy-7,8-dihydro-6H-cyclopenta[e]pyrazolo[1,5-a]pyridin-3-amine hydrochloride The compound that has crystallized was drained on a frit, washed with 2×25 ml of water, 10 ml of methanol and then with 3×50 ml of isopropyl ether. After drying at 35° C. under vacuum in the presence of $P_2O_5$ for 12 hours, 7.82 g of a beige solid corresponding to the expected compound was recovered.

NMR analyses ($^1$H 400 MHz and $^{13}$C 100.61 MHz DMSO $d_6$) and mass spectrophotometry were consistent with the expected structure.

The quasi-molecular ions $[M+H]^+$, $[M+Na]^+$, $[M+Na+CH_3OH]^+$, $[2M+Na]^+$ were mainly detected.

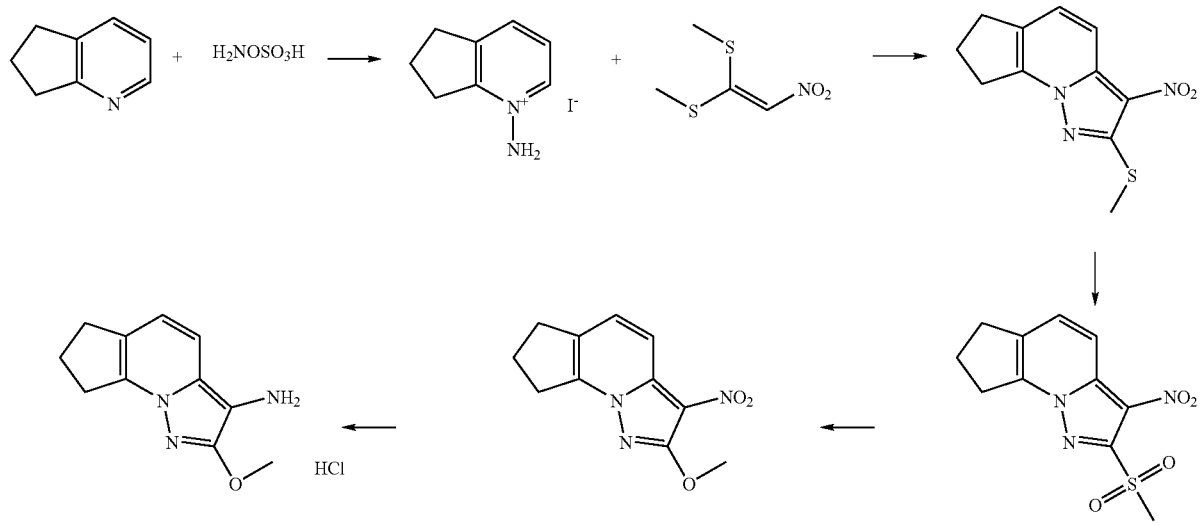

Synthesis of 2-methoxy-3-nitro-7,8-dihydro-6H-cyclopenta[e]pyrazolo[1,5-a]pyridine Synthesis of 2-methoxy-7,8-dihydro-6H-cyclopenta[e]pyrazolo[1,5-a]pyridin-3-amine hydrochloride

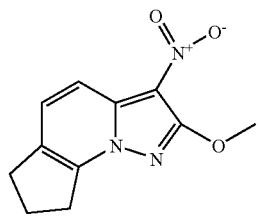

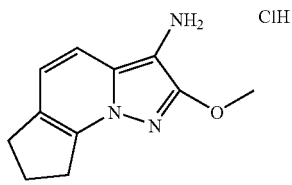

35 ml of methanol, 10 g (0,03555 mol) of 2-(methylsulphonyl)-3-nitro-7,8-dihydro-6H-cyclopenta[e]pyrazolo[1,5-a]pyridine and 33 ml of 30% sodium methylate were put in a 250 ml three-necked flask equipped with a bulb condenser, a thermometer and a magnetic stirrer, and stirred for 18 hours.

50 ml of ethanol and 5 g of zinc powder were put in a 500 ml three-necked flask equipped with a bulb condenser, a thermometer and a magnetic stirrer, and brought to reflux.

Then added dropwise were 5 ml of acid acetic and then, in portions, 5 g of 2-methoxy-3-nitro-7,8-dihydro-6H-cyclopenta[e]pyrazolo[1,5-a]pyridine. At the end of discharge, 1 ml of acetic acid was added dropwise and reflux was maintained for 2 hours.

At the end of reduction, the zinc was removed by filtration under argon on a bed of Celite and the filtrate was collected in a flask containing 50 ml of previously cooled 6N hydrochloric isopropanol.

Precipitation of a bluish-grey solid was observed. This was drained on a No. 3 frit and washed with 2×15 ml of ethanol and 2×50 ml of isopropyl ether. After drying under vacuum in the presence of $P_2O_5$ and soda tablets, 3.92 g of a bluish-grey powder corresponding to the expected compound was recovered.

NMR analyses ($^1$H 400 MHz and $^{13}$C 100.61 MHz DMSO $d_6$) and mass spectrophotometry were consistent with the expected structure.

The expected cation $[C_{15}H_{22}N_5O_2]^+$ was mainly detected.

Example 28

2-isopropoxy-7,8-dihydro-6H-cyclopenta[e]pyrazolo[1,5-a]pyridin-3-amine hydrochloride dine and 7.29 g (0.08887 mol) of sodium isopropoxide, were put in portions, in a 250 ml three-necked flask equipped with a bulb condenser, a thermometer and a magnetic stirrer, and stirred for 30 minutes.

The mixture was poured into 300 ml of water, and the compound that crystallized was drained on a No. 3 frit, washed with plenty of water and then with 4×50 ml of isopropyl ether. After drying at 35° C. under vacuum in the presence of $P_2O_5$ for 12 hours, 3.70 g of a deep yellow solid corresponding to the expected compound was recovered.

NMR analyses ($^1$H 400 MHz and $^{13}$C 100.61 MHz DMSO $d_6$) and mass spectrophotometry were consistent with the expected structure.

The quasi-molecular ions $[M+H]^+$, $[M+Na]^+$, $[M+Na+CH_3OH]^+$, $[2M+Na]^+$ were mainly detected.

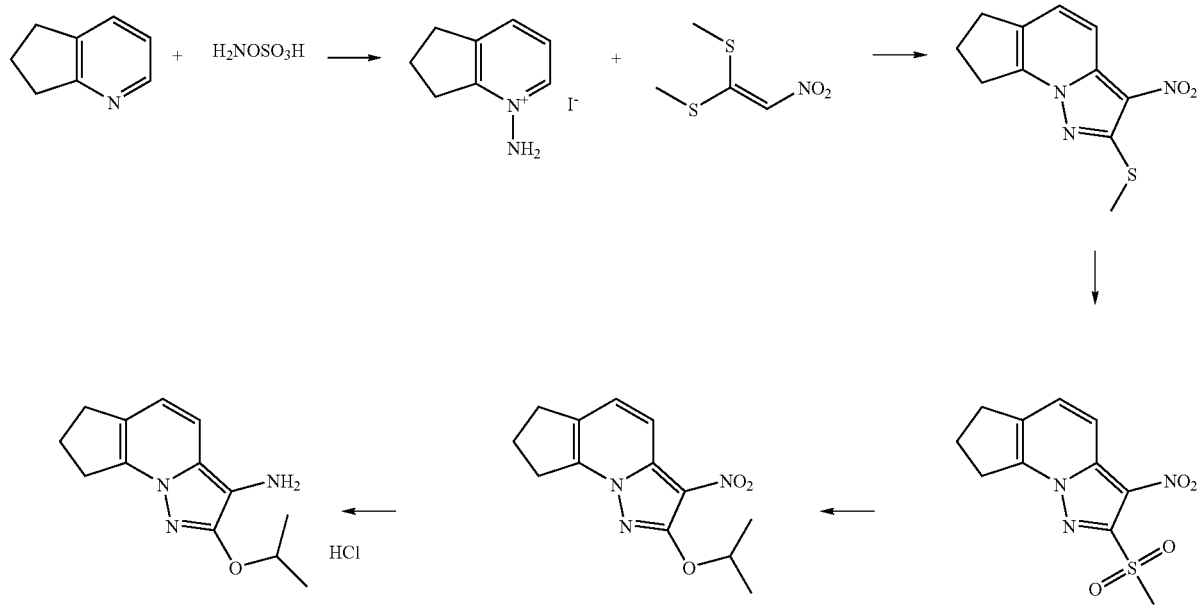

Synthesis of 2-isopropoxy-3-nitro-7,8-dihydro-6H-cyclopenta[e]pyrazolo[1,5-a]pyridine

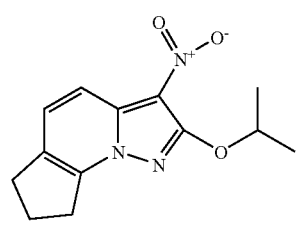

100 ml of THF, 10 g (0.03555 mol) 2-(methylsulphonyl)-3-nitro-7,8-dihydro-6H-cyclopenta[e]pyrazolo[1,5-a]pyri- Synthesis of 2-isopropoxy-7,8-dihydro-6H-cyclopenta[e]pyrazolo[1,5-a]pyridin-3-amine hydrochloride

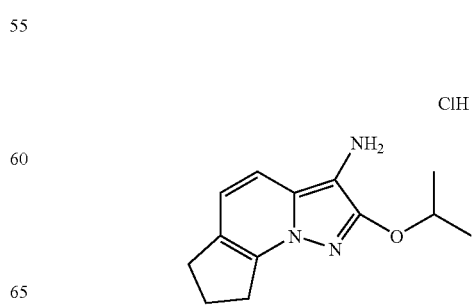

150 ml of ethanol and 3 g of zinc powder were put in a 250 ml three-necked flask equipped with a bulb condenser, a thermometer and a magnetic stirrer, and brought to reflux.

Then added dropwise were 2 ml of acid acetic and then, in portions, 3 g of 2-isopropoxy-3-nitro-7,8-dihydro-6H-cyclopenta[e]pyrazolo[1,5-a]pyridine. At the end of discharge, 1 ml of acetic acid was added dropwise and reflux was maintained for 2 hours.

At the end of reduction, the zinc was removed by filtration under argon on a bed of Celite and the filtrate was collected in a flask containing 50 ml of previously cooled 6N hydrochloric isopropanol.

The filtrate was concentrated to ⅓, then taken up several times in ether. Slow crystallization of a light green solid was observed. This was drained on a No. 3 frit and washed with 2×50 ml of ether. After drying under vacuum in the presence of $P_2O_5$ and soda tablets, 1.67 g of a pale pink powder corresponding to the expected compound was recovered.

NMR analyses ($^1$H 400 MHz and $^{13}$C 100.61 MHz DMSO $d_6$) and mass spectrophotometry were consistent with the expected structure.

The quasi-molecular ions $[M+H]^+$, $[M+Na]^+$, $[M+H+CH_3OH]^+$ of the expected molecule $C_{10}H_{13}N_3O$ were detected.

Example 29

2-(2-piperidin-1-ylethoxy)pyrazolo[1,5-a]pyridin-3-amine chlorhydrate

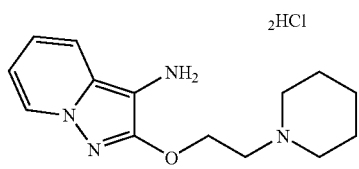

General Synthesis

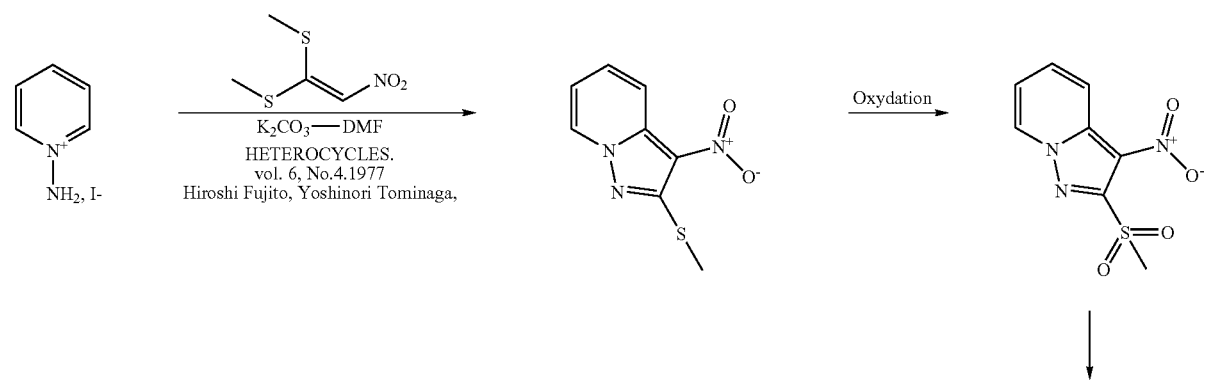

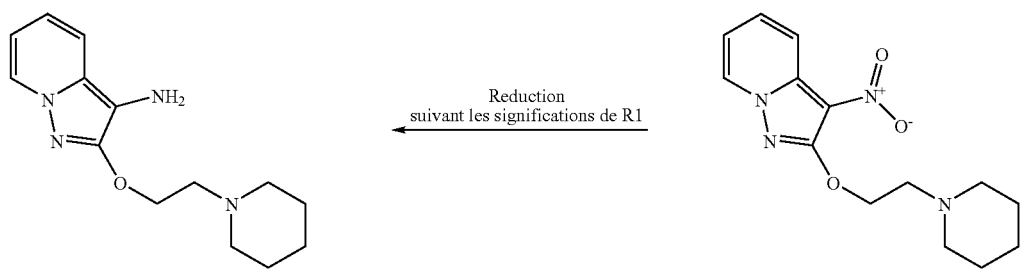

Synthesis of 3-nitro-2-(2-piperidin-1-ylethoxy)pyrazolo[1,5-a]pyridine 10 ml of water and 13.8 ml (0.103 mol) of N-(2-hydroxyethyl)piperidine were put in a 250 ml three-necked flask equipped with a bulb condenser, a thermometer, and a magnetic stirrer and cooled to 0° C., then a solution containing 8.29 g (0.207 mol) of soda and 20 ml of water was added in 15 minutes.

The mixture was stirred at this temperature for 15 minutes, then a solution containing 100 ml of N-methylpyrrolidinone and 10 g (0.04145 mol) of 2-(methylsulfonyl)-3-nitropyrazolo[1,5-a]pyridine was added dropwise in 20 minutes.

The heterogeneous violet mixture obtained was stirred for 4 hours at ambient temperature. The solid formed was drained and washed with plenty of water until a neutral pH was obtained, then with 4×50 ml of isopropyl ether. After drying at 35° C. under vacuum, in the presence of $P_2O_5$, for 12 hours, 3.70 g of a beige solid corresponding to the expected compound was recovered.

NMR analyses (1H 400 MHz and 13C 100.61 MHz DMSO d6) and mass spectrophotometry were consistent with the expected structure.

The quasi-molecular ions $[M+H]^+$, $[M+Na]^+$, $[M+Na+CH_3OH]^+$, $[2M+Na]^+$ were mainly detected.

Synthesis of 2-(2-piperidin-1-ylethoxy)pyrazolo[1,5-a]pyridin-3-amine chlorohydrate 30 ml of ethanol and 2.75 g of zinc powder were placed in a 100 ml three-necked flask equipped with a bulb condenser, a thermometer, and a magnetic stirrer, and brought to reflux. Then 550 μl of acetic acid was added dropwise, and then, in portions, 2.75 g of 3-nitro-2-(2-piperidin-1-ylethoxy)pyrazolo[1,5-a]pyridine. At the end of the addition, 2 drops of acetic acid were added and reflux was maintained for 4 hours.

At the end of reduction, the zinc was removed by filtration under argon on a bed of Celite and the filtrate was collected in a flask containing 100 ml of previously cooled 6N hydrochloric isopropanol.

The filtrate was concentrated to ⅓ of volume, then taken up several times in ether. Slow crystallization of a violet solid was observed. This was drained on a No. 3 frit and washed with a minimal amount of isopropanol and then with 3×30 ml of ether. After drying under vacuum, in the presence of $P_2O_5$ and soda tablets, 1.71 g of a pale pink powder corresponding to the expected compound were recovered.

The NMR analyses (1H 400 MHz and 13C 100, 61 MHz DMSO d6) and mass spectrophotometry were consistent with the expected structure.

The quasi-molecular ions $[M+H]^+$, $[M+Na]^+$, $[M+H+CH_3OH]$ of the expected molecule $C_{14}H_{20ON4}O$ were detected.

Example 30

2-[2-(dimethylamino)ethoxy]pyrazolo[1,5-a]pyridin-3-amine chlorohydrate

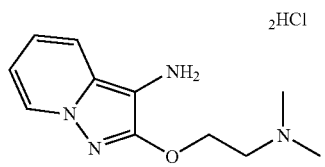

General Synthesis

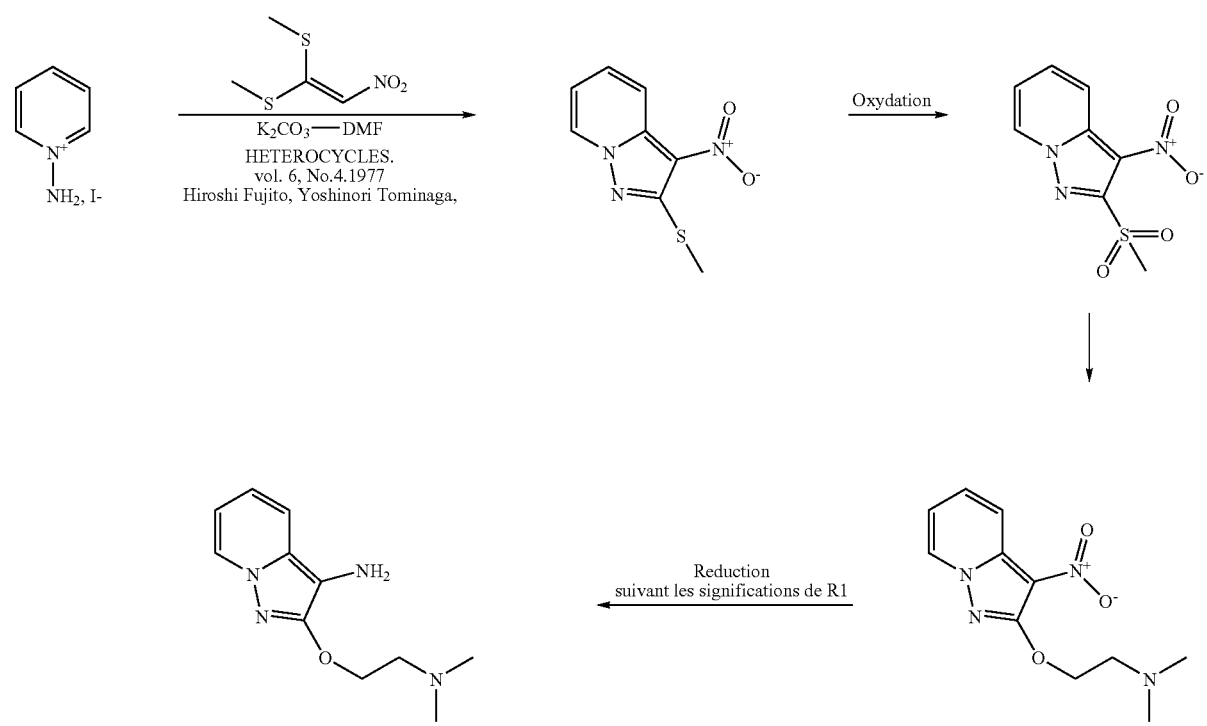

Synthesis of N,N-dimethyl-2-[(3-nitropyrazolo[1,5-a]pyridin-2-yl)oxy]ethanamine 10 ml of water and 10.3 ml (0.103 mol) of N,N-dimethyl-ethanolamine were put in a 250 ml three-necked flask equipped with a bulb condenser, a thermometer, and a magnetic stirrer and cooled to 0° C., then a solution containing 8.29 g (0.207 mol) of soda and 20 ml of water were added in 15 minutes.

The solution was stirred at this temperature for 15 minutes, then a solution containing 100 ml of N-methylpyrrolidinone and 10 g (0.04145 mol) of 2-(methylsulfonyl)-3-nitropyrazolo[1,5-a]pyridine is added dropwise in 20 minutes.

The mixture obtained was light violet and was stirred for 6 hours at ambient temperature. The reaction mixture was pored onto 500 ml of water. The beige solid formed was drained and washed with plenty of water until a neutral pH was obtained, then with 4×50 ml of isopropyl ether. After drying at 35° C. under vacuum, in the presence of $P_2O_5$, for 12 hours, 5.01 g of a beige solid corresponding to the expected compound was recovered.

NMR analyses (1H 400 MHz and 13C 100.61 MHz DMSO d6) and mass spectrophotometry were consistent with the expected structure.

The quasi-molecular ions $[M+H]^+$, $[M+Na]^+$, $[M+Na+CH_3OH]^+$, $[2M+Na]^+$ were mainly detected.

Synthesis of 2-[2-(dimethylamino)ethoxy]pyrazolo[1,5-a]pyridin-3-amine chlorhydrate 20 ml of ethanol and 25 of zinc powder were put in a 100 ml three-necked flask equipped with a bulb condenser, a thermometer, and a magnetic stirrer, and brought to reflux. Two drops of acetic acid were added, and then, in portions, 2 g of N,N-dimethyl-2-[(3-nitropyrazolo[1,5-a]pyridin-2-yl)oxy]ethanamine. At the end of the addition, two drops of acetic acid were added and reflux was maintained for 17 hours.

At the end of reduction, the zinc was removed by filtration under argon on a bed of Celite and the filtrate was collected in a flask containing 100 ml of previously cooled 6N hydrochloric isopropanol.

The filtrate was concentrated to ⅓ of volume, and then taken up several times in ether. Slow crystallization of a violet solid was observed. This was drained on a No. 3 frit and washed with a minimal amount of isopropanol and then with 3×30 ml of ether. After drying under vacuum, in the presence of $P_2O_5$ and soda tablets, 2.80 g of a pale violet powder corresponding to the expected compound were recovered.

The NMR analyses (1H 400 MHz and 13C 100.61 MHz DMSO d6) and mass spectrophotometry were consistent with the expected structure.

The quasi-molecular ions $[M+H]^+$, $[M+Na]^+$, $[M+H+CH_3OH]$ of the expected molecule $C_{11}H_{16}N_4O$ were detected.

Examples of Dyeing

The following dyeing compositions were prepared

| | | | | | | | |
|---|---|---|---|---|---|---|---|
| 2-isopropoxypyrazolo[1,5-a]pyridin-3-amine hydrochloride | $10^{-3}$ mole | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | | |
| 5-Amino-2-methyl-phenol | | $10^{-3}$ mole | | | | | |
| 1H-Indol-6-ol | | | $10^{-3}$ mole | | | | |
| 2-Amino-pyridin-3-ol | | | | $10^{-3}$ mole | | | |
| 3,6-Dimethyl-1H-pyrazolo[5,1-c][1,2,4]triazole | | | | | $10^{-3}$ mole | | |
| 2-(2,4-Diamino-phenoxy)-ethanol, hydrochloride | | | | | | $10^{-3}$ mole | |
| 3-Amino-2-chloro-6-methyl-phenol, hydrochloride | | | | | | | $10^{-3}$ mole |
| Dyeing support (1) | (*) | (*) | (*) | (*) | (*) | (*) | (*) |
| Demineralized water q.s.f. | 100 g | 100 g | 100 g | 100 g | 100 g | 100 g | 100 g |
| Shade observed | bright red | bright chromatic red | bright red | bright violet-red | chromatic red | bright red | bright chromatic red |

| | | | | |
|---|---|---|---|---|
| 2-[3-(dimethylamino)pyrrolidin-1-yl]pyrazolo[1,5-a]pyridin-3-amine hydrochloride | $10^{-3}$ mole | $10^{-3}$ mole | $10^{-3}$ mole | $10^{-3}$ mole |
| 5-Amino-2-methyl-phenol | $10^{-3}$ mole | | | |
| 1H-Indol-6-ol | | $10^{-3}$ mole | | |
| 3,6-Dimethyl-1H-pyrazolo[5,1-c][1,2,4]triazole | | | $10^{-3}$ mole | |
| 2-(2,4-Diamino-phenoxy)-ethanol, hydrochloride | | | | $10^{-3}$ mole |
| Dyeing support (2) | (*) | (*) | (*) | (*) |
| Demineralized water q.s.f. | 100 g | 100 g | 100 g | 100 g |

| Shade observed | | bright blue | orange-brown | red | | bright greenish-blue-grey |
|---|---|---|---|---|---|---|
| 2-[3-(dimethylamino)pyrrolidin-1-yl]pyrazolo[1,5-a]pyridin-3-amine hydrochloride | | | $10^{-3}$ mole | | | $10^{-3}$ mole |
| 5-Amino-2-methyl-phenol | | | $10^{-3}$ mole | | | |
| 2-(2,4-Diamino-phenoxy)-ethanol, hydrochloride | | | | | | $10^{-3}$ mole |
| Dyeing support (1) | | | (*) | | | (*) |
| Demineralized water q.s.f. | | | 100 g | | | 100 g |
| Shade observed | | | blue-grey | | | greenish-blue-grey |

| | | | | | | |
|---|---|---|---|---|---|---|
| 2-methoxy-7-methylpyrazolo[1,5-a]pyridin-3-amine hydrochloride | $10^{-3}$ mole | $10^{-3}$ mole | $10^{-3}$ mole | $10^{-3}$ mole | $10^{-3}$ mole | $10^{-3}$ mole |
| 5-Amino-2-methyl-phenol | $10^{-3}$ mole | | | | | |
| 1H-Indol-6-ol | | $10^{-3}$ mole | | | | |
| 2-Amino-pyridin-3-ol | | | $10^{-3}$ mole | | | |
| 3,6-Dimethyl-1H-pyrazolo[5,1-c][1,2,4]triazole | | | | $10^{-3}$ mole | | |
| 2-(2,4-Diamino-phenoxy)-ethanol, hydrochloride | | | | | $10^{-3}$ mole | |
| 3-Amino-2-chloro-6-methyl-phenol, hydrochloride | | | | | | $10^{-3}$ mole |
| Dyeing support (2) | (*) | (*) | (*) | (*) | (*) | (*) |
| Demineralized water q.s.f. | 100 g | 100 g | 100 g | 100 g | 100 g | 100 g |
| Shade observed | bright chromatic red | bright red | reddish-brown | bright chromatic red | bright red | bright chromatic red |

| | | | | | | |
|---|---|---|---|---|---|---|
| 2-methoxy-7-methylpyrazolo[1,5-a]pyridin-3-amine hydrochloride | $10^{-3}$ mole | $10^{-3}$ mole | $10^{-3}$ mole | $10^{-3}$ mole | $10^{-3}$ mole | $10^{-3}$ mole |
| 5-Amino-2-methyl-phenol | $10^{-3}$ mole | | | | | |
| 1H-Indol-6-ol | | $10^{-3}$ mole | | | | |
| 2-Amino-pyridin-3-ol | | | $10^{-3}$ mole | | | |
| 3,6-Dimethyl-1H-pyrazolo[5,1-c][1,2,4]triazole | | | | $10^{-3}$ mole | | |
| 2-(2,4-Diamino-phenoxy)-ethanol, hydrochloride | | | | | $10^{-3}$ mole | |
| 3-Amino-2-chloro-6-methyl-phenol, hydrochloride | | | | | | $10^{-3}$ mole |
| Dyeing support (1) | (*) | (*) | (*) | (*) | (*) | (*) |
| Demineralized water q.s.f. | 100 g | 100 g | 100 g | 100 g | 100 g | 100 g |
| Shade observed | bright chromatic red | bright reddish-brown | brown-red | bright chromatic red | bright red | bright chromatic red |

| | | | | |
|---|---|---|---|---|
| 2-pyrrolidin-1-ylpyrazolo[1,5-a]pyridin-3-amine hydrochloride | | | $10^{-3}$ mole | $10^{-3}$ mole |
| 5-Amino-2-methyl-phenol | | | $10^{-3}$ mole | |
| 2-(2,4-Diamino-phenoxy)-ethanol, hydrochloride | | | | $10^{-3}$ mole |
| Dyeing support (2) | | | (*) | (*) |
| Demineralized water q.s.f. | | | 100 g | 100 g |
| Shade observed | | | grey-green | bright greenish-blue-grey |

| | | | | |
|---|---|---|---|---|
| 2-pyrrolidin-1-ylpyrazolo[1,5-a]pyridin-3-amine hydrochloride | | | $10^{-3}$ mole | $10^{-3}$ mole |
| 5-Amino-2-methyl-phenol | | | $10^{-3}$ mole | |
| 2-(2,4-Diamino-phenoxy)-ethanol, hydrochloride | | | | $10^{-3}$ mole |
| Dyeing support (1) | | | (*) | (*) |

-continued

| | | | | | | |
|---|---|---|---|---|---|---|
| Demineralized water q.s.f. | | 100 g | 100 g | | | |
| Shade observed | | greenish-blue | grey-greenish-blue | | | |

| | | | | | | |
|---|---|---|---|---|---|---|
| N2-[3-(1H-imidazol-1-yl)propyl] pyrazolo[1,5-a]pyridine-2,3-diamine hydrochloride | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | |
| 5-Amino-2-methyl-phenol | | $10^{-3}$ mole | | | | |
| 1H-Indol-6-ol | | | $10^{-3}$ mole | | | |
| 3,6-Dimethyl-1H-pyrazolo[5,1-c][1,2,4]triazole | | | | $10^{-3}$ mole | | |
| 2-(2,4-Diamino-phenoxy)-ethanol, hydrochloride | | | | | $10^{-3}$ mole | |
| 3-Amino-2-chloro-6-methyl-phenol, hydrochloride | | | | | | $10^{-3}$ mole |
| Dyeing support (2) | (*) | (*) | (*) | (*) | (*) | (*) |
| Demineralized water q.s.f. | 100 g | 100 g | 100 g | 100 g | 100 g | 100 g |
| Shade observed | grey-green | Grey-greenish-blue | Grey-green | grey-green | greenish-blue | greenish-blue |

| | | | |
|---|---|---|---|
| N2-[3-(1H-imidazol-1-yl)propyl]pyrazolo[1,5-a]pyridine-2,3-diamine hydrochloride | $10^{-3}$ mole | $10^{-3}$ mole | $10^{-3}$ mole |
| 5-Amino-2-methyl-phenol | $10^{-3}$ mole | | |
| 2-(2,4-Diamino-phenoxy)-ethanol, hydrochloride | | $10^{-3}$ mole | |
| 3-Amino-2-chloro-6-methyl-phenol, hydrochloride | | | $10^{-3}$ mole |
| Dyeing support (1) | (*) | (*) | (*) |
| Demineralized water q.s.f. | 100 g | 100 g | 100 g |
| Shade observed | bluish-grey | grey-green | greenish-blue |

| | | | | |
|---|---|---|---|---|
| 2-(4-methylpiperazin-1-yl)pyrazolo[1,5-a]pyridin-3-amine hydrochloride | $10^{-3}$ mole | $10^{-3}$ mole | $10^{-3}$ mole | $10^{-3}$ mole |
| 5-Amino-2-methyl-phenol | $10^{-3}$ mole | | | |
| 1H-Indol-6-ol | | $10^{-3}$ mole | | |
| 2-(2,4-Diamino-phenoxy)-ethanol, hydrochloride | | | $10^{-3}$ mole | |
| 3-Amino-2-chloro-6-methyl-phenol, hydrochloride | | | | $10^{-3}$ mole |
| Dyeing support (2) | (*) | (*) | (*) | (*) |
| Demineralized water q.s.f. | 100 g | 100 g | 100 g | 100 g |
| Shade observed | grey-violet-red | orange | bright greenish-blue grey | bluish grey |

| | | | |
|---|---|---|---|
| 2-(4-methylpiperazin-1-yl)pyrazolo[1,5-a]pyridin-3-amine hydrochloride | $10^{-3}$ mole | $10^{-3}$ mole | $10^{-3}$ mole |
| 5-Amino-2-methyl-phenol | $10^{-3}$ mole | | |
| 2-(2,4-Diamino-phenoxy)-ethanol, hydrochloride | | $10^{-3}$ mole | |
| 3-Amino-2-chloro-6-methyl-phenol, hydrochloride | | | $10^{-3}$ mole |
| Dyeing support (1) | (*) | (*) | (*) |
| Demineralized water q.s.f. | 100 g | 100 g | 100 g |
| Shade observed | grey-violet | grey-greenish-blue | bluish-grey |

| | |
|---|---|
| 2-[(3-aminopyrazolo[1,5-a]pyridin-2-yl)amino]ethanol hydrochloride | $10^{-3}$ mole |
| 2-(2,4-Diamino-phenoxy)-ethanol, hydrochloride | $10^{-3}$ mole |
| Dyeing support (2) | (*) |
| Demineralized water q.s.f. | 100 g |
| Shade observed | grey-greenish-blue |

| | | |
|---|---|---|
| 2-[(3-aminopyrazolo[1,5-a]pyridin-2-yl)amino]ethanol hydrochloride | $10^{-3}$ mole | $10^{-3}$ mole |
| 2-(2,4-Diamino-phenoxy)- | $10^{-3}$ mole | |

-continued

| | | |
|---|---|---|
| ethanol, hydrochloride | | |
| 3-Amino-2-chloro-6-methyl-phenol, hydrochloride | | $10^{-3}$ mole |
| Dyeing support (1) | (*) | (*) |
| Demineralized water q.s.f. | 100 g | 100 g |
| Shade observed | bright greenish-blue | blue |

| | |
|---|---|
| 1-[(3-aminopyrazolo[1,5-a]pyridin-2-yl)amino]propan-2-ol hydrochloride | $10^{-3}$ mole |
| 2-(2,4-Diamino-phenoxy)-ethanol, hydrochloride | $10^{-3}$ mole |
| Dyeing support (2) | (*) |
| Demineralized water q.s.f. | 100 g |
| Shade observed | grey-green |

| | | | |
|---|---|---|---|
| 1-[(3-aminopyrazolo[1,5-a]pyridin-2-yl)amino]propan-2-ol hydrochloride | $10^{-3}$ mole | $10^{-3}$ mole | $10^{-3}$ mole |
| 5-Amino-2-methyl-phenol | $10^{-3}$ mole | | |
| 2-(2,4-Diamino-phenoxy)-ethanol, hydrochloride | | $10^{-3}$ mole | |
| 3-Amino-2-chloro-6-methyl-phenol, hydrochloride | | | $10^{-3}$ mole |
| Dyeing support (1) | (*) | (*) | (*) |
| Demineralized water q.s.f. | 100 g | 100 g | 100 g |
| Shade observed | bluish-grey | grey-green | greenish-blue |

| | |
|---|---|
| N2-ethylpyrazolo[1,5-a]pyridine-2,3-diamine hydrochloride | $10^{-3}$ mole |
| 2-(2,4-Diamino-phenoxy)-ethanol, hydrochloride | $10^{-3}$ mole |
| Dyeing support (2) | (*) |
| Demineralized water q.s.f. | 100 g |
| Shade observed | grey-yellow-green |

| | |
|---|---|
| N2-ethylpyrazolo[1,5-a]pyridine-2,3-diamine hydrochloride | $10^{-3}$ mole |
| 3-Amino-2-chloro-6-methyl-phenol, hydrochloride | $10^{-3}$ mole |
| Dyeing support (1) | (*) |
| Demineralized water q.s.f. | 100 g |
| Shade observed | greenish-blue |

| | | | | |
|---|---|---|---|---|
| 2-[(3-amino-7,8-dihydro-6H-cyclopenta[e]pyrazolo[1,5-a]pyridin-2-yl)amino]ethanol hydrochloride | $10^{-3}$ mole | $10^{-3}$ mole | $10^{-3}$ mole | $10^{-3}$ mole |
| 5-Amino-2-methyl-phenol | $10^{-3}$ mole | | | |
| 1H-Indol-6-ol | | $10^{-3}$ mole | | |
| 2-(2,4-Diamino-phenoxy)-ethanol, hydrochloride | | | $10^{-3}$ mole | |
| 3-Amino-2-chloro-6-methyl-phenol, hydrochloride | | | | $10^{-3}$ mole |
| Dyeing support (1) | (*) | (*) | (*) | (*) |
| Demineralized water q.s.f. | 100 g | 100 g | 100 g | 100 g |
| Shade observed | green | yellow-green | green | greenish-blue |

| | | | | | | | |
|---|---|---|---|---|---|---|---|
| 2-[(3-amino-7,8-dihydro-6H-cyclopenta[e]pyrazolo[1,5-a]pyridin-2-yl)amino]ethanol hydrochloride | $10^{-3}$ mole | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | | |
| 5-Amino-2-methyl-phenol | | $10^{-3}$ mole | | | | | |
| 1H-Indol-6-ol | | | $10^{-3}$ mole | | | | |
| 2-Amino-pyridin-3-ol | | | | $10^{-3}$ mole | | | |
| 3,6-Dimethyl-1H-pyrazolo[5,1-c][1,2,4]triazole | | | | | $10^{-3}$ mole | | |
| 2-(2,4-Diamino-phenoxy)-ethanol, hydrochloride | | | | | | $10^{-3}$ mole | |
| 3-Amino-2-chloro-6-methyl-phenol, hydrochloride | | | | | | | $10^{-3}$ mole |
| Dyeing support (2) | (*) | (*) | (*) | (*) | (*) | (*) | (*) |
| Demineralized water q.s.f. | 100 g | 100 g | 100 g | 100 g | 100 g | 100 g | 100 g |
| Shade observed | green | green | grey-green | green | green | grey-green | green |

-continued

| | | | | | | |
|---|---|---|---|---|---|---|
| 2-methoxy-7,8-dihydro-6H-cyclopenta[e]pyrazolo[1,5-a]pyridin-3-amine hydrochloride | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | |
| 1H-Indol-6-ol | | $10^{-3}$ mole | | | | |
| 2-Amino-pyridin-3-ol | | | $10^{-3}$ mole | | | |
| 3,6-Dimethyl-1H-pyrazolo[5,1-c][1,2,4]triazole | | | | $10^{-3}$ mole | | |
| 2-(2,4-Diamino-phenoxy)-ethanol, hydrochloride | | | | | $10^{-3}$ mole | |
| 3-Amino-2-chloro-6-methyl-phenol, hydrochloride | | | | | | $10^{-3}$ mole |
| Dyeing support (1) | (*) | (*) | (*) | (*) | (*) | (*) |
| Demineralized water q.s.f. | 100 g | 100 g | 100 g | 100 g | 100 g | 100 g |
| Shade observed | bright reddish-violet-grey | bright reddish-grey | grey | bright chromatic red | bright reddish-brown | bright red |

| | | | | | | | |
|---|---|---|---|---|---|---|---|
| 2-methoxy-7,8-dihydro-6H-cyclopenta[e]pyrazolo[1,5-a]pyridin-3-amine hydrochloride | $10^{-3}$ mole | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | | |
| 5-Amino-2-methyl-phenol | | $10^{-3}$ mole | | | | | |
| 1H-Indol-6-ol | | | $10^{-3}$ mole | | | | |
| 2-Amino-pyridin-3-ol | | | | $10^{-3}$ mole | | | |
| 3,6-Dimethyl-1H-pyrazolo[5,1-c][1,2,4]triazole | | | | | $10^{-3}$ mole | | |
| 2-(2,4-Diamino-phenoxy)-ethanol, hydrochloride | | | | | | $10^{-3}$ mole | |
| 3-Amino-2-chloro-6-methyl-phenol, hydrochloride | | | | | | | $10^{-3}$ mole |
| Dyeing support (2) | (*) | (*) | (*) | (*) | (*) | (*) | (*) |
| Demineralized water q.s.f. | 100 g | 100 g | 100 g | 100 g | 100 g | 100 g | 100 g |
| Shade observed | bright grey-violet | bright red | bright reddish-brown | bright grey | bright red | bright reddish-brown | bright red |

| | | | |
|---|---|---|---|
| N2-[2-(dimethylamino)ethyl]-7,8-dihydro-6H-cyclopenta[e]pyrazolo[1,5-a]pyridine-2,3-diamine hydrochloride | $10^{-3}$ mole | $10^{-3}$ mole | $10^{-3}$ mole |
| 5-Amino-2-methyl-phenol | $10^{-3}$ mole | | |
| 2-(2,4-Diamino-phenoxy)-ethanol, hydrochloride | | $10^{-3}$ mole | |
| 3-Amino-2-chloro-6-methyl-phenol, hydrochloride | | | $10^{-3}$ mole |
| Dyeing support (1) | (*) | (*) | (*) |
| Demineralized water q.s.f. | 100 g | 100 g | 100 g |
| Shade observed | greenish-blue | green | greenish-blue |

| | | | | | | |
|---|---|---|---|---|---|---|
| N2-[2-(dimethylamino)ethyl]-7,8-dihydro-6H-cyclopenta[e]pyrazolo[1,5-a]pyridine-2,3-diamine hydrochloride | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | |
| 5-Amino-2-methyl-phenol | | $10^{-3}$ mole | | | | |

-continued

| | | | | | | | |
|---|---|---|---|---|---|---|---|
| 1H-Indol-6-ol | | | 10⁻³ mole | | | | |
| 2-Amino-pyridin-3-ol | | | | 10⁻³ mole | | | |
| 3,6-Dimethyl-1H-pyrazolo[5,1-c][1,2,4]triazole | | | | | 10⁻³ mole | | |
| 2-(2,4-Diamino-phenoxy)-ethanol, hydrochloride | | | | | | 10⁻³ mole | |
| 3-Amino-2-chloro-6-methyl-phenol, hydrochloride | | | | | | | 10⁻³ mole |
| Dyeing support (2) | (*) | (*) | (*) | (*) | (*) | (*) | (*) |
| Demineralized water q.s.f. | 100 g | 100 g | 100 g | 100 g | 100 g | 100 g | 100 g |
| Shade observed | chromatic green | green | green | chromatic green | greenish-blue | greenish-blue | bright greenish-blue |

| | | | | |
|---|---|---|---|---|
| N2-[2-(diethylamino)ethyl]pyrazolo[1,5-a]pyridine-2,3-diamine hydrochloride | 10⁻³ mole | 10⁻³ mole | 10⁻³ mole | 10⁻³ mole |
| 5-Amino-2-methyl-phenol | 10⁻³ mole | | | |
| 2-Amino-pyridin-3-ol | | 10⁻³ mole | | |
| 2-(2,4-Diamino-phenoxy)-ethanol, hydrochloride | | | 10⁻³ mole | |
| 3-Amino-2-chloro-6-methyl-phenol, hydrochloride | | | | 10⁻³ mole |
| Dyeing support (2) | (*) | (*) | (*) | (*) |
| Demineralized water q.s.f. | 100 g | 100 g | 100 g | 100 g |
| Shade observed | violet-blue | grey | bright blue | bright violet-blue |

| | | | | |
|---|---|---|---|---|
| N2-[2-(diethylamino)ethyl]pyrazolo[1,5-a]pyridine-2,3-diamine hydrochloride | 10⁻³ mole | 10⁻³ mole | 10⁻³ mole | 10⁻³ mole |
| 5-Amino-2-methyl-phenol | 10⁻³ mole | | | |
| 1H-Indol-6-ol | | 10⁻³ mole | | |
| 2-(2,4-Diamino-phenoxy)-ethanol, hydrochloride | | | 10⁻³ mole | |
| 3-Amino-2-chloro-6-methyl-phenol, hydrochloride | | | | 10⁻³ mole |
| Dyeing support (1) | (*) | (*) | (*) | (*) |
| Demineralized water q.s.f. | 100 g | 100 g | 100 g | 100 g |
| Shade observed | bright violet-blue | reddish-brown | bright blue | bright violet-blue |

| | | | | | |
|---|---|---|---|---|---|
| N2-[2-(diisopropylamino)ethyl]pyrazolo[1,5-a]pyridine-2,3-diamine hydrochloride | 10⁻³ mole | 10⁻³ mole | 10⁻³ mole | 10⁻³ mole | 10⁻³ mole |
| 5-Amino-2-methyl-phenol | 10⁻³ mole | | | | |
| 1H-Indol-6-ol | | 10⁻³ mole | | | |
| 3,6-Dimethyl-1H-pyrazolo[5,1-c][1,2,4]triazole | | | 10⁻³ mole | | |
| 2-(2,4-Diamino-phenoxy)-ethanol, hydrochloride | | | | 10⁻³ mole | |
| 3-Amino-2-chloro-6-methyl-phenol, hydrochloride | | | | | 10⁻³ mole |
| Dyeing support (2) | (*) | (*) | (*) | (*) | (*) |
| Demineralized water q.s.f. | 100 g | 100 g | 100 g | 100 g | 100 g |
| Shade observed | bright violet-blue | bright orange-brown | red | bright blue | bright violet-blue |

| | | | | | | |
|---|---|---|---|---|---|---|
| N2-[2-(diisopropylamino)ethyl]pyrazolo[1,5-a]pyridine-2,3-diamine hydrochloride | 10⁻³ mole | 10⁻³ mole | 10⁻³ mole | 10⁻³ mole | 10⁻³ mole | 10⁻³ mole |
| Benzene-1,3-diol | 10⁻³ mole | | | | | |
| 5-Amino-2-methyl-phenol | | 10⁻³ mole | | | | |
| 1H-Indol-6-ol | | | 10⁻³ mole | | | |
| 3,6-Dimethyl-1H-pyrazolo[5,1-c][1,2,4]triazole | | | | 10⁻³ mole | | |

-continued

| | | | | | | |
|---|---|---|---|---|---|---|
| 2-(2,4-Diamino-phenoxy)-ethanol, hydrochloride | | | | | $10^{-3}$ mole | |
| 3-Amino-2-chloro-6-methyl-phenol, hydrochloride | | | | | | $10^{-3}$ mole |
| Dyeing support (1) | (*) | (*) | (*) | (*) | (*) | (*) |
| Demineralized water q.s.f. | 100 g | 100 g | 100 g | 100 g | 100 g | 100 g |
| Shade observed | brown | bright violet | bright reddish-brown | bright chromatic red | bright blue | bright chromatic violet-blue |

| | | | | | |
|---|---|---|---|---|---|
| N2-(2-pyridin-3-ylethyl)pyrazolo[1,5-a]pyridine-2,3-diamine hydrochloride | $10^{-3}$ mole | $10^{-3}$ mole | $10^{-3}$ mole | $10^{-3}$ mole | |
| 5-Amino-2-methyl-phenol | $10^{-3}$ mole | | | | |
| 1H-Indol-6-ol | | $10^{-3}$ mole | | | |
| 2-(2,4-Diamino-phenoxy)-ethanol, hydrochloride | | | $10^{-3}$ mole | | |
| 3-Amino-2-chloro-6-methyl-phenol, hydrochloride | | | | $10^{-3}$ mole | |
| Dyeing support (2) | (*) | (*) | (*) | (*) | |
| Demineralized water q.s.f. | 100 g | 100 g | 100 g | 100 g | |
| Shade observed | grey greenish-blue | yellow-brown | bright greenish-blue | bright blue | |

| | | | | | | |
|---|---|---|---|---|---|---|
| N2-(2-pyridin-3-ylethyl)pyrazolo[1,5-a]pyridine-2,3-diamine hydrochloride | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | |
| 5-Amino-2-methyl-phenol | | $10^{-3}$ mole | | | | |
| 1H-Indol-6-ol | | | $10^{-3}$ mole | | | |
| 3,6-Dimethyl-1H-pyrazolo[5,1-c][1,2,4]triazole | | | | $10^{-3}$ mole | | |
| 2-(2,4-Diamino-phenoxy)-ethanol, hydrochloride | | | | | $10^{-3}$ mole | |
| 3-Amino-2-chloro-6-methyl-phenol, hydrochloride | | | | | | $10^{-3}$ mole |
| Dyeing support (1) | (*) | (*) | (*) | (*) | (*) | (*) |
| Demineralized water q.s.f. | 100 g | 100 g | 100 g | 100 g | 100 g | 100 g |
| Shade observed | bright greenish-blue-grey | bright violet-blue | bright reddish-brown | red | bright blue | bright blue |

| | | | | |
|---|---|---|---|---|
| N2-(2-pyridin-4-ylethyl)pyrazolo[1,5-a]pyridine-2,3-diamine hydrochloride | $10^{-3}$ mole | $10^{-3}$ mole | | $10^{-3}$ mole |
| 5-Amino-2-methyl-phenol | $10^{-3}$ mole | | | |
| 2-(2,4-Diamino-phenoxy)-ethanol, hydrochloride | | $10^{-3}$ mole | | |
| 3-Amino-2-chloro-6-methyl-phenol, hydrochloride | | | | $10^{-3}$ mole |
| Dyeing support (2) | (*) | (*) | | (*) |
| Demineralized water q.s.f. | 100 g | 100 g | | 100 g |
| Shade observed | grey | bright greenish-blue | | blue |

| | | | | | | |
|---|---|---|---|---|---|---|
| N2-(2-pyridin-4-ylethyl)pyrazolo[1,5-a]pyridine-2,3-diamine hydrochloride | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | |
| 5-Amino-2-methyl-phenol | | $10^{-3}$ mole | | | | |
| 1H-Indol-6-ol | | | $10^{-3}$ mole | | | |
| 2-(2,4-Diamino-phenoxy)-ethanol, hydrochloride | | | | $10^{-3}$ mole | | |
| 3-Amino-2-chloro-6-methyl-phenol, hydrochloride | | | | | $10^{-3}$ mole | |
| Dyeing support (1) | (*) | (*) | (*) | (*) | (*) | |

| | | | | | | |
|---|---|---|---|---|---|---|
| Demineralized water q.s.f. | 100 g | 100 g | 100 g | 100 g | 100 g | |
| Shade observed | grey | bright violet-blue | reddish-brown | bright greenish-blue | blue | |
| 2-isopropoxypyrazolo[1,5-a]pyridin-3-amine hydrochloride | $10^{-3}$ mole | $10^{-3}$ mole | $10^{-3}$ mole | $10^{-3}$ mole | $10^{-3}$ mole | $10^{-3}$ mole |
| Benzene-1,3-diol | $10^{-3}$ mole | | | | | |
| 5-Amino-2-methyl-phenol | | $10^{-3}$ mole | | | | |
| 1H-Indol-6-ol | | | $10^{-3}$ mole | | | |
| 2-Amino-pyridin-3-ol | | | | $10^{-3}$ mole | | |
| 2-(2,4-Diamino-phenoxy)-ethanol, hydrochloride | | | | | $10^{-3}$ mole | |
| 3-Amino-2-chloro-6-methyl-phenol, hydrochloride | | | | | | $10^{-3}$ mole |
| Dyeing support (2) | (*) | (*) | (*) | (*) | (*) | (*) |
| Demineralized water q.s.f. | 100 g | 100 g | 100 g | 100 g | 100 g | 100 g |
| Shade observed | reddish-brown | bright chromatic red | red | red | bright red | bright chromatic red |

| (*): dyeing support (1) pH 7 [A.S. = active substance] | |
|---|---|
| Ethanol, 96° | 20.8 g |
| Sodium metabisulphite, 35% aqueous solution | 0.23 g A.S. |
| Pentasodium salt of diethylenetriamine-pentaacetic acid, 40% aqueous solution | 0.48 g A.S. |
| $C_8$-$C_{10}$ alkyl polyglucoside, 60% aqueous solution | 3.6 g A.S. |
| Benzyl alcohol | 2.0 g |
| Polyethylene glycol with 8 units of ethylene oxide | 3.0 g |
| $Na_2HPO_4$ | 0.28 g |
| $KH_2PO_4$ | 0.46 g |

| (*): dyeing support (2) pH 9.5 | |
|---|---|
| Ethanol, 96° | 20.8 g |
| Sodium metabisulphite, 35% aqueous solution | 0.23 g A.S. |
| Pentasodium salt of diethylenetriamine-pentaacetic acid, 40% aqueous solution | 0.48 g A.S. |
| $C_8$-$C_{10}$ alkyl polyglucoside, 60% aqueous solution | 3.6 g A.S. |
| Benzyl alcohol | 2.0 g |
| Polyethylene glycol with 8 units of ethylene oxide | 3.0 g |
| $NH_4Cl$ | 4.32 g |
| Ammonia at 20% of $NH_3$ | 2.94 g |

At the moment of use, each composition was mixed with an equal weight of hydrogen peroxide solution at 20 volumes (6 wt. %). A final pH of 7, or 9.5, was obtained.

Each mixture obtained was applied to locks of grey hair at 90% white. After a waiting time of 30 minutes, the locks were rinsed, washed with a standard shampoo, rinsed again and then dried.

The results obtained are shown in the above tables.

What is claimed is:

1. A composition for dyeing keratin fibers comprising, in a medium suitable for dyeing, at least one oxidation dyeing base chosen from 3-aminopyrazolo-[1,5-a]-pyridine derivatives of formula (I) and salts and solvates thereof:

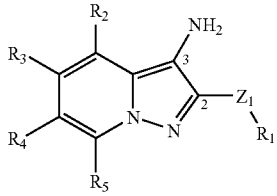

(I)

in which

Z$_1$ is chosen from an oxygen atom and a group NR$_6$; when Z$_1$ is NR$_6$ then R$_1$ and R$_6$ can form, together with the nitrogen atom to which they are attached, a saturated, unsaturated or aromatic heterocycle with 5 to 8 ring members, optionally substituted, Z$_1$ can alternatively be chosen from divalent radical S, SO, and SO$_2$ when R$_1$ is CH$_3$, R$_6$ is chosen from:
  hydrogen,
  C$_1$-C$_{10}$ alkyl radicals, optionally substituted with at least one saturated, unsaturated or aromatic (hetero)cycle with 5 to 8 ring members, optionally substituted
  saturated, unsaturated or aromatic (hetero)cycles with 5 to 8 ring members, optionally substituted, R$_2$, R$_3$, R$_4$, R$_5$, independently, are chosen from:
  hydrogen,
  C$_1$-C$_4$ alkyl radicals, optionally substituted,
  a group chosen from NH$_2$, NHR$_{10}$, NR$_{11}$R$_{12}$, OH, OR$_9$, wherein R$_9$ and R$_{10}$ are each chosen, independently, from a linear or branched C$_1$-C$_6$ alkyl, optionally substituted, wherein R$_{11}$ and R$_{12}$ which may be identical or different, are each chosen from a linear or branched C$_1$-C$_6$ alkyl, optionally substituted, R$_{11}$ and R$_{12}$ possibly forming, together with the nitrogen atom to which they are attached, a saturated, unsaturated, or aromatic heterocycle with 5 to 8 ring members optionally comprising at least one other heteroatom or group chosen from N, O, S, SO$_2$, and CO, the heterocycle being optionally substituted $R_2, R_3, R_4, R_5$, can form, two by two with adjacent radicals, a saturated or unsaturated (hetero)cycle, optionally substituted, with the exception of 2-methoxypyrazolo[1,5-a]pyridin-3-ylamine and 2-morpholino-pyrazolo[1,5-a]pyridin-3-ylamine respectively of the following formulae:

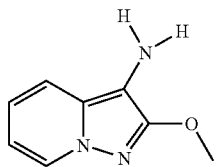

2-Methoxypyrazolo [1,5-a] pyridin-3-ylamine

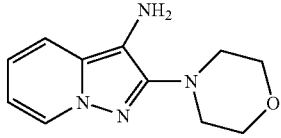

2-Morpholin-4-yl-pyrazolo [1,5-a] pyridin-3-ylamine, and wherein radical $R_1$ is chosen from $C_1$-$C_{10}$ alkyl radicals, $C_1$-$C_{10}$ alkyl radical substituted with a hydroxy, $C_1$-$C_{10}$ alkyl radical substituted with an amino or (di)alkylamino radical, and $C_1$-$C_{10}$ alkyl radical substituted with a nitrogen-containing heterocycle wherein $R_1$ and $R_6$ are not both $C_1$-$C_{10}$ alkyl radicals and wherein $Z_1$ and $R_1$ together can not form ($C_1$-$C_4$) alkoxy radicals if $R_4$ and $R_5$ together can not form a saturated or unsaturated (hetero)cycle.

2. A composition for dyeing keratin fibers comprising, in a medium suitable for dyeing, at least one oxidation dyeing base chosen from 3-aminopyrazolo-[1,5-a]-pyridine derivatives of formula (I) and salts and solvates thereof:

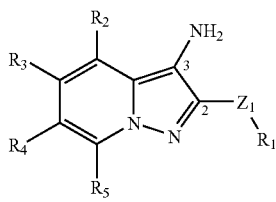

in which $Z_1$ is chosen from an oxygen atom and a group $NR_6$; when $Z_1$ is $NR_6$ then $R_1$ and $R_6$ can form, together with the nitrogen atom to which they are attached, a saturated, unsaturated or aromatic heterocycle with 5 to 8 ring members, optionally substituted, $Z_1$ can alternatively be chosen from divalent radical S, SO, and SO$_2$ when $R_1$ is CH$_3$, $R_1$ is chosen from:
hydrogen,
$C_1$-$C_{10}$ alkyl radicals, optionally substituted with at least one saturated, unsaturated or aromatic (hetero)cycle with 5 to 8 ring members, optionally substituted saturated, unsaturated or aromatic (hetero)cycles with 5 to 8 ring members, optionally substituted, $R_2, R_3, R_4, R_5$, independently, are chosen from:
hydrogen,
$C_1$-$C_4$ alkyl radicals, optionally substituted,
a group chosen from NH$_2$, NHR$_{10}$, NR$_{11}$R$_{12}$, OH, OR$_9$, wherein $R_9$ and $R_{10}$ are each chosen, independently, from a linear or branched $C_1$-$C_6$ alkyl, optionally substituted, wherein $R_{11}$ and $R_{12}$ which may be identical or different, are each chosen from a linear or branched $C_1$-$C_6$ alkyl, optionally substituted, $R_{11}$ and $R_{12}$ possibly forming, together with the nitrogen atom to which they are attached, a saturated, unsaturated, or aromatic heterocycle with 5 to 8 ring members optionally comprising at least one other heteroatom or group chosen from N, O, S, SO$_2$, and CO, the heterocycle being optionally substituted $R_2, R_3, R_4, R_5$, can form, two by two with adjacent radicals, a saturated or unsaturated (hetero)cycle, optionally substituted, with the exception of 2-methoxypyrazolo[1,5-a]pyridin-3-ylamine and 2-morpholino-pyrazolo[1,5-a]pyridin-3-ylamine respectively of the following formulae:

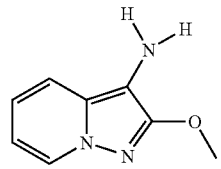

2-Methoxypyrazolo [1,5-a] pyridin-3-ylamine

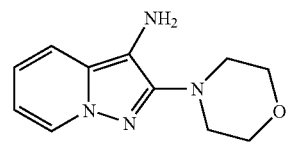

2-Morpholin-4-yl-pyrazolo [1,5-a] pyridin-3-ylamine, and wherein radical $R_6$ is chosen from a hydrogen atom, $C_1$-$C_{10}$ alkyl radicals, $C_1$-$C_{10}$ alkyl radical substituted with a hydroxy radical, an amino radical, $C_1$-$C_{10}$ alkylamino radical, a $C_1$-$C_{10}$ dialkylamino radical, and $C_1$-$C_{10}$ alkyl radical substituted with a nitrogen-containing heterocycle wherein $R_1$ and $R_6$ are not both hydrogen atoms or $C_1$-$C_{10}$ alkyl radicals and wherein $Z_1$ and $R_1$ together can not form ($C_1$-$C_4$) alkoxy radicals if $R_4$ and $R_5$ together can not form a saturated or unsaturated (hetero)cycle.

3. A composition according to claim 1, in which the alkyl radical has from 1 to 6 carbon atoms.

4. A composition according to claim 2, in which the alkyl radical has from 1 to 6 carbon atoms.

5. A composition for dyeing keratin fibers comprising, in a medium suitable for dyeing, at least one oxidation dyeing base chosen from 3-aminopyrazolo-[1,5-a]-pyridine derivatives of formula (I) and salts and solvates thereof:

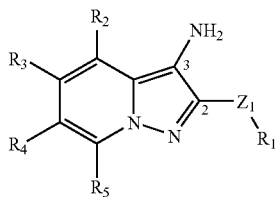

(I)

in which
- $Z_1$ is chosen from an oxygen atom and a group $NR_6$; when $Z_1$ is $NR_6$ then $R_1$ and $R_6$ can form, together with the nitrogen atom to which they are attached, a saturated, unsaturated or aromatic heterocycle with 5 to 8 ring members, optionally substituted,
- $Z_1$, can alternatively be chosen from divalent radical S, SO, and $SO_2$ when $R_1$ is $CH_3$,
- $R_1$ and $R_6$ are chosen from, independently:
  - hydrogen,
  - $C_1$-$C_{10}$ alkyl radicals, optionally substituted with at least one saturated, unsaturated or aromatic (hetero)cycle with 5 to 8 ring members, optionally substituted
  - saturated, unsaturated or aromatic (hetero)cycles with 5 to 8 ring members, optionally substituted,
- $R_2$, $R_3$, $R_4$, $R_5$, independently, are chosen from:
  - hydrogen,
  - $C_1$-$C_4$ alkyl radicals, optionally substituted,
  - a group chosen from $NH_2$, $NHR_{10}$, $NR_{11}R_{12}$, OH, $OR_9$, wherein $R_9$ and $R_{10}$ are each chosen, independently, from a linear or branched $C_1$-$C_6$ alkyl, optionally substituted, wherein $R_{11}$ and $R_{12}$ which may be identical or different, are each chosen from a linear or branched $C_1$-$C_6$ optionally substituted, $R_{11}$ and $R_{12}$ possibly forming, together with the nitrogen atom to which they are attached, a saturated, unsaturated, or aromatic heterocycle with 5 to 8 ring members optionally comprising at least one other heteroatom or group chosen from N, O, S, $SO_2$ and CO, the heterocycle being optionally substituted
- $R_2$, $R_3$, $R_4$, $R_5$, can form, two by two with adjacent radicals, a saturated or unsaturated (hetero)cycle, optionally substituted, with the exception of 2-methoxypyrazolo[1,5-a]pyridin-3-ylamine and 2-morpholino-pyrazolo[1,5-a]pyridin-3-ylamine respectively of the following formulae:

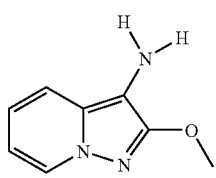

2-Methoxypyrazolo [1,5-a] pyridin-3-ylamine

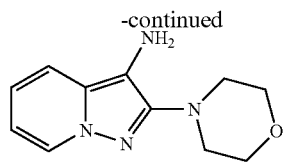

2-Morpholin-4-yl-pyrazolo [1,5-a] pyridin-3-ylamine, and wherein the radicals $R_4$ and $R_5$ together form a saturated or unsaturated (hetero)cycle with 5 to 8 ring members.

6. A composition according to claim 5 in which $R_4$ and $R_5$ together form a cyclopentane radicals and wherein $Z_1$ and $R_1$ together can not form ($C_1$-$C_4$)alkoxy radicals if $R_4$ and $R_5$ together can not form a saturated or unsatuated (hetero)cycle --.

7. A method of preparation of a compound of formula (I):

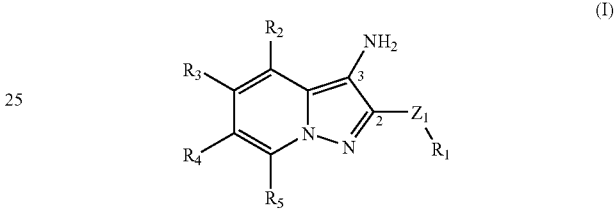

(I)

in which
- $Z_1$ is chosen from an oxygen atom and a group $NR_6$; when $Z_1$ is $NR_6$ then $R_1$ and $R_6$ can form, together with the nitrogen atom to which they are attached, a saturated, unsaturated or aromatic heterocycle with 5 to 8 ring members, optionally substituted,
- $Z_1$ can alternatively be chosen from divalent radical S, SO, and $SO_2$ when $R_1$ is $CH_3$,
- $R_1$ and $R_6$ are chosen from, independently:
  - hydrogen,
  - $C_1$-$C_{10}$ alkyl radicals, optionally substituted with at least one saturated, unsaturated or aromatic (hetero)cycle with 5 to 8 ring members, optionally substituted
  - saturated, unsaturated or aromatic (hetero)cycles with 5 to 8 ring members, optionally substituted,
- $R_2$, $R_3$, $R_4$, $R_5$, independently, are chosen from:
  - hydrogen,
  - $C_1$-$C_4$ alkyl radicals, optionally substituted,
  - a group chosen from $NH_2$, $NHR_{10}$, $NR_{11}R_{12}$, OH, $OR_9$, wherein $R_9$ and $R_{10}$ are each chosen, independently, from a linear or branched $C_1$-$C_6$ alkyl, optionally substituted, wherein $R_{11}$ and $R_{12}$, which may be identical or different, are each chosen from a linear or branched $C_1$-$C_6$ alkyl, optionally substituted, $R_{11}$ and $R_{12}$ possibly forming, together with the nitrogen atom to which they are attached, a saturated, unsaturated, or aromatic heterocycle with 5 to 8 ring members optionally comprising at least one other heteroatom or group chosen from N, O, S, $SO_2$, and CO, the heterocycle being optionally substituted
- $R_2$, $R_3$, $R_4$, $R_5$, can form, two by two with adjacent radicals, a saturated or unsaturated (hetero)cycle, optionally substituted, with the exception of 2-methoxypyrazolo[1,5-a]pyridin-3-ylamine and 2-morpholino-pyrazolo[1,5-a]pyridin-3-ylamine respectively of the following formulae:

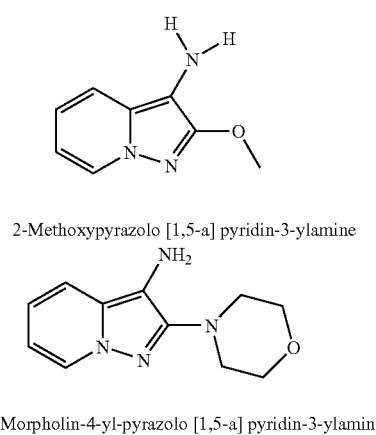

2-Methoxypyrazolo [1,5-a] pyridin-3-ylamine

2-Morpholin-4-yl-pyrazolo [1,5-a] pyridin-3-ylamine said method comprising the following stages:

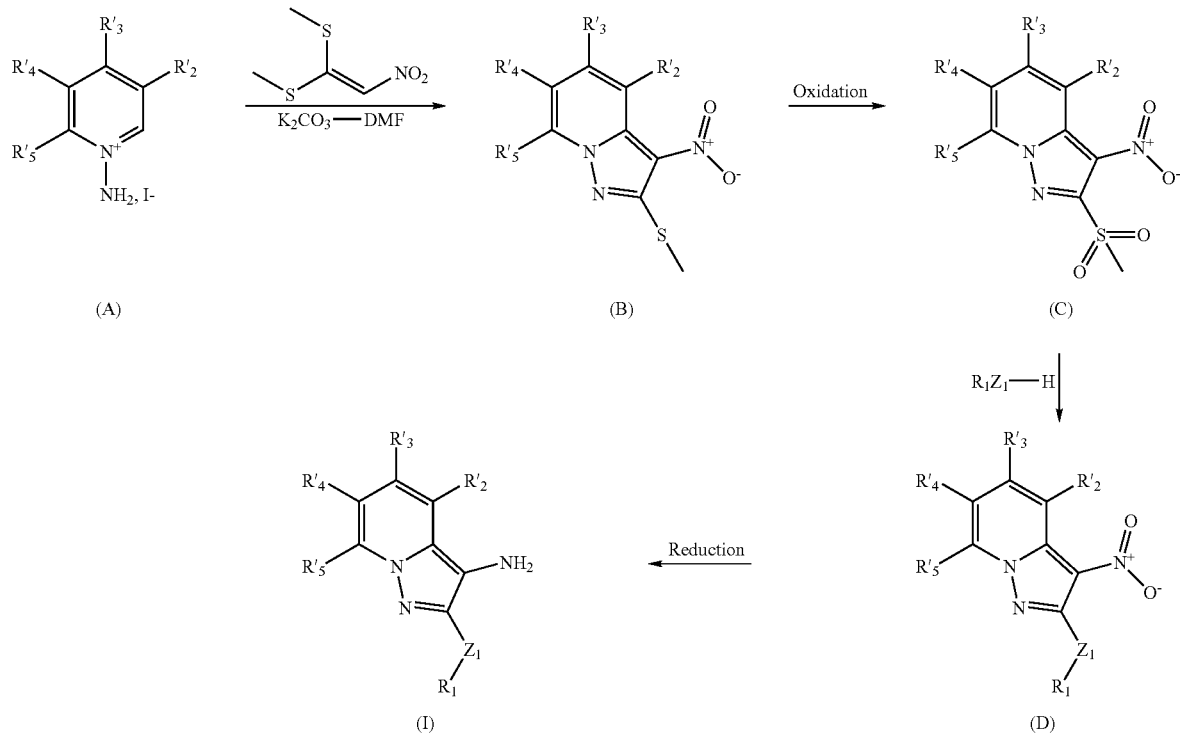

in which $R'_2$, $R'_3$, $R'_4$ and $R'_5$ have the same meanings as $R_2$, $R_3$, $R_4$ and $R_5$ or are precursors thereof.

8. Compounds of formula (A), salts thereof, solvates thereof, and derivatives thereof:

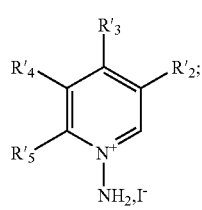

(A)

wherein:

$R'_2$, $R'_3$, $R'_4$, $R'_5$, independently, are chosen from:
hydrogen, $C_1$-$C_4$ alkyl radicals, optionally substituted, a group chosen from $NH_2$, $NHR_{10}$, $NR_{11}R_{12}$, OH, $OR_9$, wherein $R_9$ and $R_{10}$ are each chosen, independently, from a linear or branched $C_1$-$C_6$ alkyl, optionally substituted, wherein $R_{11}$ and $R_{12}$, which may be identical or different, are each chosen from a linear or branched $C_1$-$C_6$ alkyl, optionally substituted, $R_{11}$ and $R_{12}$ possibly forming, together with the nitrogen atom to which they are attached, a saturated, unsaturated, or aromatic heterocycle with 5 to 8 ring members optionally comprising at least one other heteroatom or group chosen from N, O, S, $SO_2$, and CO, the heterocycle being optionally substituted; and $R'_2$, $R'_3$, $R'_4$, and $R'_5$, can form, two by two with adjacent radicals, a saturated or unsaturated (hetero)cycle, optionally substituted;

with the proviso that at least one of the radicals $R'_2$, $R'_3$, $R'_4$, or $R'_5$ is not a hydrogen atom, except in the case of the compound for which $R'_2$=Me, in which case all of the other substituents are hydrogen.

9. Compounds of formula (B), salts thereof, solvates thereof, and derivatives thereof:

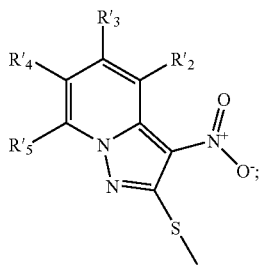

(B)

wherein:

R'$_2$, R'$_3$, R'$_4$, R'$_5$, independently, are chosen from:
hydrogen,
C$_1$-C$_4$ alkyl radicals, optionally substituted,
a group chosen from NH$_2$, NHR$_{10}$, NR$_{11}$R$_{12}$, OH, OR$_9$, wherein R$_9$ and R$_{10}$ are each chosen, independently, from a linear or branched C$_1$-C$_6$ alkyl, optionally substituted, wherein R$_{11}$ and R$_{12}$, which may be identical or different, are each chosen from a linear or branched C$_1$-C$_6$ alkyl, optionally substituted, R$_{11}$ and R$_{12}$ possibly forming, together with the nitrogen atom to which they are attached, a saturated, unsaturated, or aromatic heterocycle with 5 to 8 ring members optionally comprising at least one other heteroatom or group chosen from N, O, S, SO$_2$, and CO, the heterocycle being optionally substituted; and
R'$_2$, R'$_3$, R'$_4$, and R'$_5$, can form, two by two with adjacent radicals, a saturated or unsaturated (hetero)cycle, optionally substituted;
with the proviso that at least one of the radicals R'$_2$, R'$_3$, R'$_4$, or R'$_5$ is not a hydrogen atom, except in the case of the compound for which R'$_2$=Me, in which case all of the other substituents are hydrogen.

10. Compounds of formula (C), salts thereof, solvates thereof, and derivatives thereof:

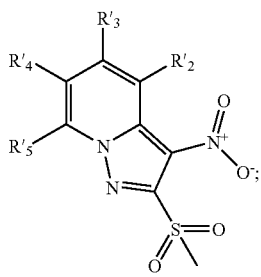

(C)

R'$_2$, R'$_3$, R'$_4$, R'$_5$, independently, are chosen from:
hydrogen,
C$_1$-C$_4$ alkyl radicals, optionally substituted,
a group chosen from NH$_2$, NHR$_{10}$, NR$_{11}$R$_{12}$, OH, OR$_9$, wherein R$_9$ and R$_{10}$ are each chosen, independently, from a linear or branched C$_1$-C$_6$ alkyl, optionally substituted, wherein R$_{11}$ and R$_{12}$, which may be identical or different, are each chosen from a linear or branched C$_1$-C$_6$ alkyl, optionally substituted, R$_{11}$ and R$_{12}$ possibly forming, together with the nitrogen atom to which they are attached, a saturated, unsaturated, or aromatic heterocycle with 5 to 8 ring members optionally comprising at least one other heteroatom or group chosen from N, O, S, SO$_2$, and CO, the heterocycle being optionally substituted; and
R'$_2$, R'$_3$, R'$_4$, and R'$_5$, can form, two by two with adjacent radicals, a saturated or unsaturated (hetero)cycle, optionally substituted.

11. Compounds of formula (D), salts thereof, solvates thereof, and derivatives thereof:

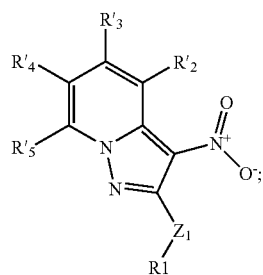

(D)

R'$_2$, R'$_3$, R'$_4$, R'$_5$, independently, are chosen from:
hydrogen,
C$_1$-C$_4$ alkyl radicals, optionally substituted,
a group chosen from NH$_2$, NHR$_{10}$, NR$_{11}$R$_{12}$, OH, OR$_9$, wherein R$_9$ and R$_{10}$ are each chosen, independently, from a linear or branched C$_1$-C$_6$ alkyl, optionally substituted, wherein R$_{11}$ and R$_{12}$, which may be identical or different, are each chosen from a linear or branched C$_1$-C$_6$ alkyl, optionally substituted, R$_{11}$ and R$_{12}$ possibly forming, together with the nitrogen atom to which they are attached, a saturated, unsaturated, or aromatic heterocycle with 5 to 8 ring members optionally comprising at least one other heteroatom or group chosen from N, O, S, SO$_2$, and CO, the heterocycle being optionally substituted; and
R'$_2$, R'$_3$, R'$_4$, and R'$_5$, can form, two by two with adjacent radicals, a saturated or unsaturated (hetero)cycle, optionally substituted.

12. A composition according to claim 1, in which the compound of formula (I) is chosen from the following compounds and corresponding addition salts or solvates:

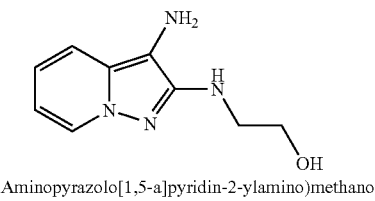

(3-Aminopyrazolo[1,5-a]pyridin-2-ylamino)methanol

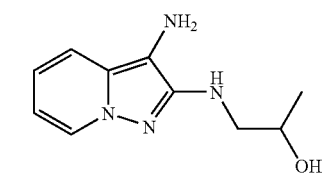

1-(3-Aminopyrazolo[1,5-a]pyridin-2-ylamino)propan-2-ol

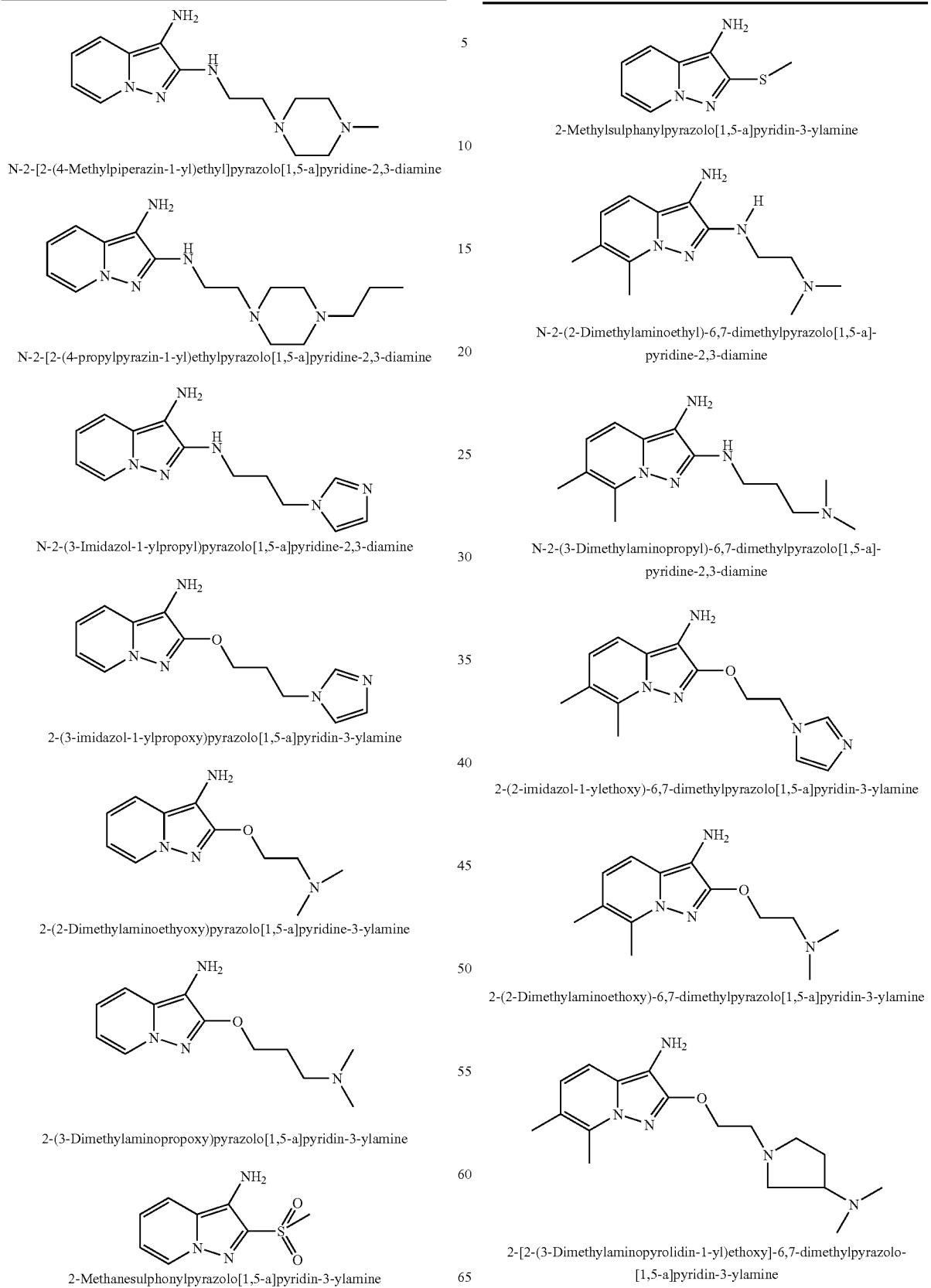

-continued

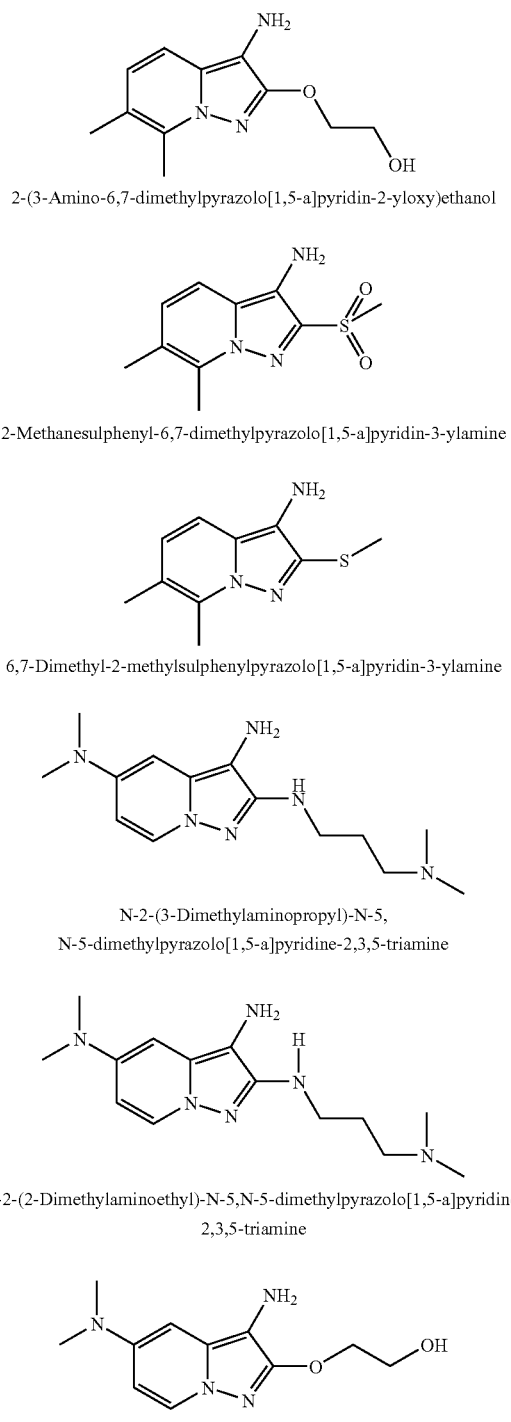

2-(3-Amino-6,7-dimethylpyrazolo[1,5-a]pyridin-2-yloxy)ethanol

2-Methanesulphenyl-6,7-dimethylpyrazolo[1,5-a]pyridin-3-ylamine 6,7-Dimethyl-2-methylsulphenylpyrazolo[1,5-a]pyridin-3-ylamine N-2-(3-Dimethylaminopropyl)-N-5,
N-5-dimethylpyrazolo[1,5-a]pyridine-2,3,5-triamine N-2-(2-Dimethylaminoethyl)-N-5,N-5-dimethylpyrazolo[1,5-a]pyridine-2,3,5-triamine 2-(3-Amino-5-dimethylaminopyrazolo[1,5-a]pyridin-2-yloxy)ethanol N-5,N-5-Dimethyl-2-methylsulphonylpyrazolo[1,5-a]pyridine-3,5-diamine -continued

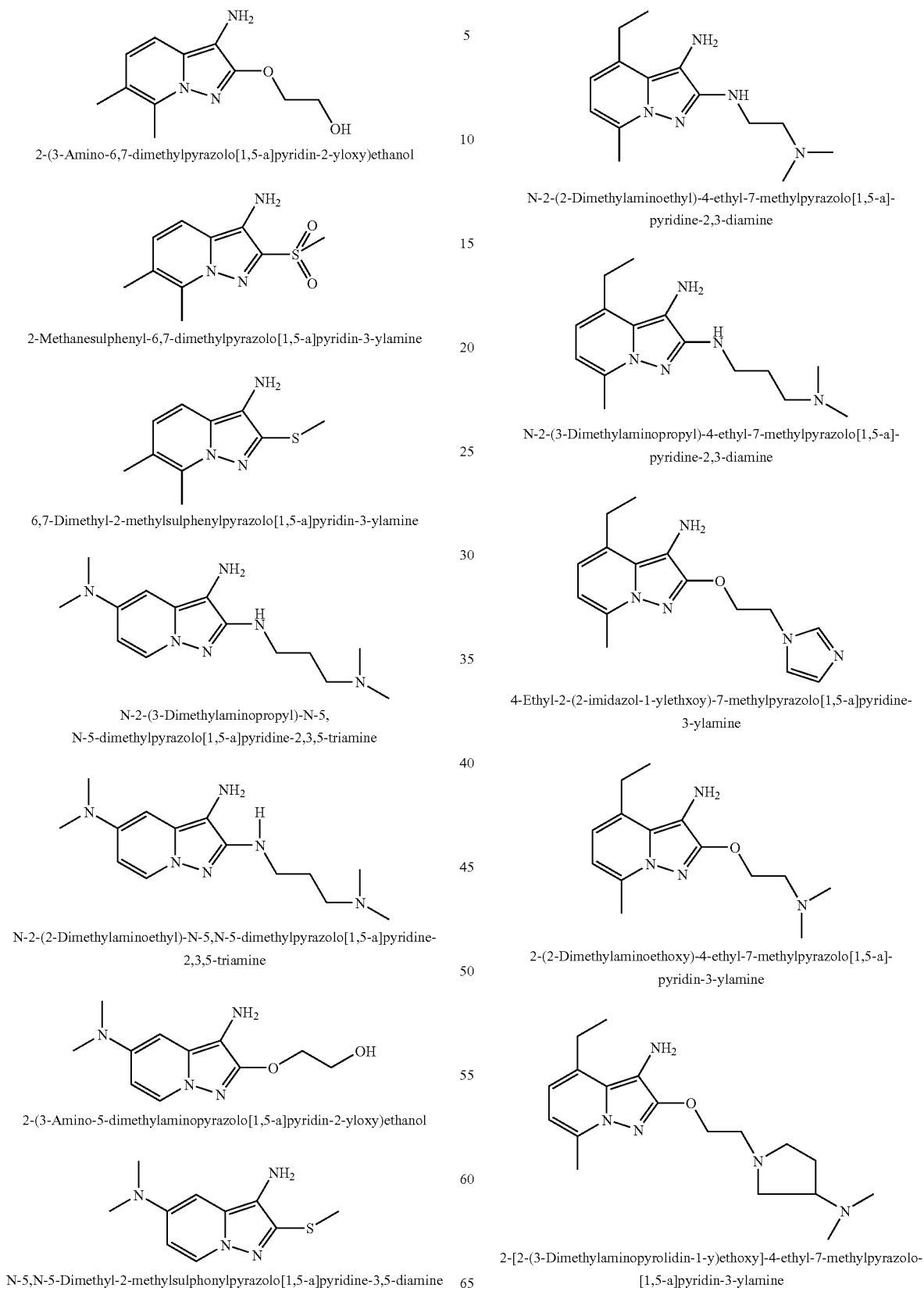

N-2-(2-Dimethylaminoethyl)-4-ethyl-7-methylpyrazolo[1,5-a]-pyridine-2,3-diamine

N-2-(3-Dimethylaminopropyl)-4-ethyl-7-methylpyrazolo[1,5-a]-pyridine-2,3-diamine 4-Ethyl-2-(2-imidazol-1-ylethxoy)-7-methylpyrazolo[1,5-a]pyridine-3-ylamine 2-(2-Dimethylaminoethoxy)-4-ethyl-7-methylpyrazolo[1,5-a]-pyridin-3-ylamine 2-[2-(3-Dimethylaminopyrolidin-1-y)ethoxy]-4-ethyl-7-methylpyrazolo-[1,5-a]pyridin-3-ylamine -continued

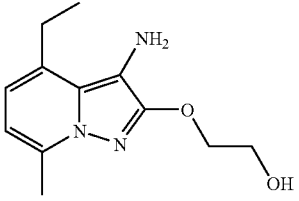

2-(3-Amino-4-ethyl-7-methylpyrazolo[1,5-a]pyridin-2-yloxy)ethanol

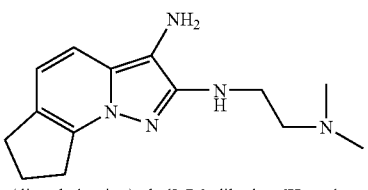

4-Ethyl-2-methanesulphonyl-7-methylpyrazolo[1,5-a]pyridin-3-ylamine

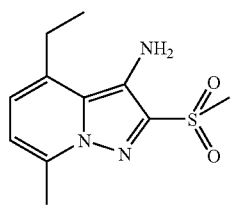

4-Ethyl-2-methylsulphenylpyrazolo[1,5-a]pyridin-3-ylamine

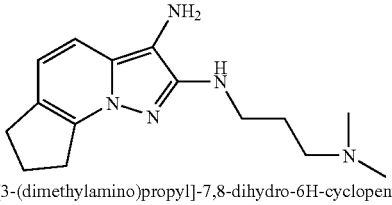

2-(methylsulphenyl)-7,8-dihydro-6H-cyclopenta[e]pyrazolo[1,5-a]pyridin-3-amine

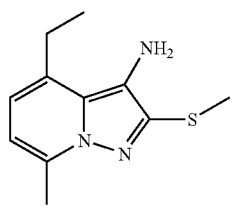

N-2-methyl-7,8-dihydro-6H-cyclopenta[e]pyrazolo[1,5-a]pyridine-2,3-diamine

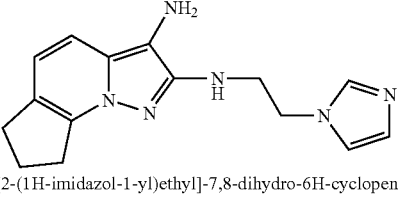

N-2-isopropyl-7,8-dihydro-6H-cyclopenta[e]pyrazolo[1,5-a]-pyridine-2,3-diamine

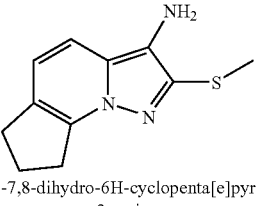

2-[(3-amine-7,8-dihydro-6H-cyclopenta[e]pyrazolo[1,5-a]-pyridin-2-yl)amino]ethanol -continued

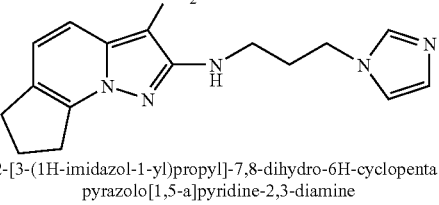

N-2-[2-(dimethylamino)ethyl]-7,8-dihydro-6H-cyclopenta[e]-pyrazolo[1,5-a]pyridine-2,3-diamine

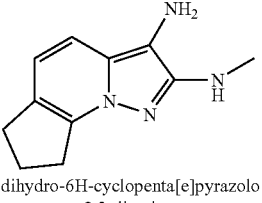

N-2-[3-(dimethylamino)propyl]-7,8-dihydro-6H-cyclopenta[e]-pyrazolo[1,5-a]pyridine-2,3-diamine

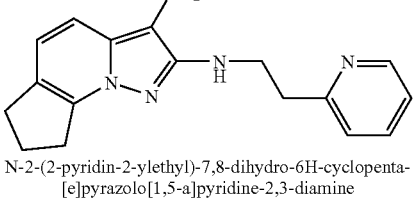

N-2-[2-(1H-imidazol-1-yl)ethyl]-7,8-dihydro-6H-cyclopenta[e]-pyrazolo[1,5-a]pyridine-26,3-diamine

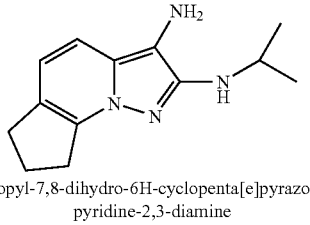

N-2-[3-(1H-imidazol-1-yl)propyl]-7,8-dihydro-6H-cyclopenta[e]-pyrazolo[1,5-a]pyridine-2,3-diamine

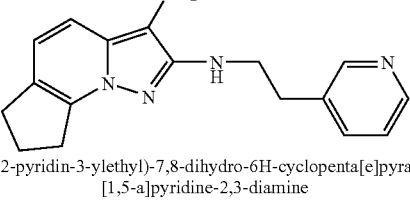

N-2-(2-pyridin-2-ylethyl)-7,8-dihydro-6H-cyclopenta-[e]pyrazolo[1,5-a]pyridine-2,3-diamine

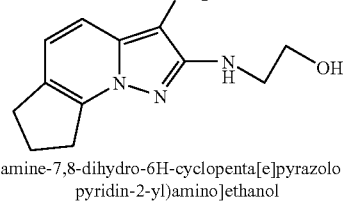

N-2-(2-pyridin-3-ylethyl)-7,8-dihydro-6H-cyclopenta[e]pyrazolo-[1,5-a]pyridine-2,3-diamine

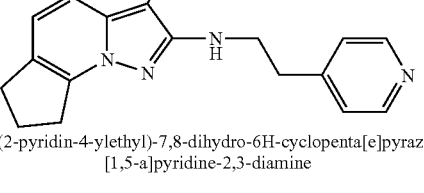

N-2-(2-pyridin-4-ylethyl)-7,8-dihydro-6H-cyclopenta[e]pyrazolo-[1,5-a]pyridine-2,3-diamine -continued

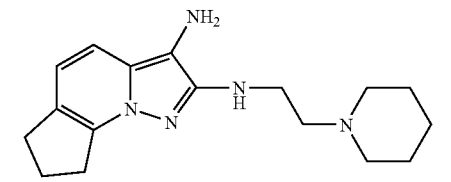

N-2-(2-piperidin-1-ylethyl)-7,8-dihydro-6H-cyclopenta[e]-
pyrazolo[1,5-a]pyridine-2,3-diamine

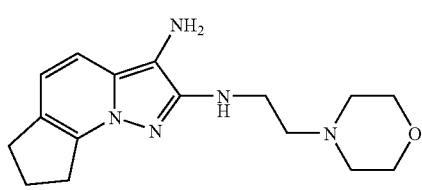

N-2-(2-morpholin-4-ylethyl)-7,8-dihydro-6H-cyclopenta[e]pyrazolo-
[1,5-a]pyridine-2,3-diamine

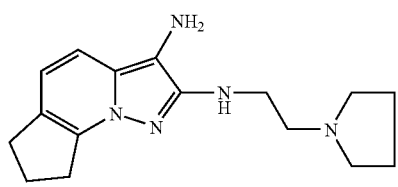

N-2-(2-pyrrolidin-1-ylethyl)-7,8-dihydro-6H-cyclopenta[e]pyrazolo-
[1,5-a]pyridine-2,3-diamine

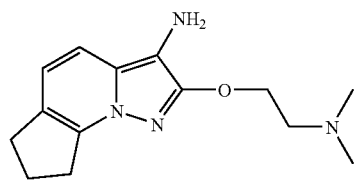

2-[2-(dimethylamino)ethoxy]-7,8-dihydro-6H-cyclopenta[e]pyrazolo-
[1,5-a]pyridin-3-amine

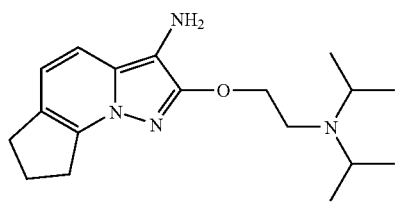

2-[2-(diisopropylamino)ethoxy]-7,8-dihydro-6H-cyclopenta[e]pyrazolo-
[1,5-a]pyridin-3-amine

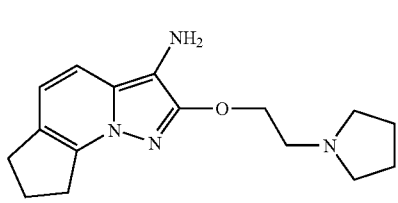

2-(2-pyrrolidin-1-ylethoxy)-7,8-dihydro-6H-cyclopenta[e]pyrazolo-
[1,5-a]pyridin-3-amine -continued

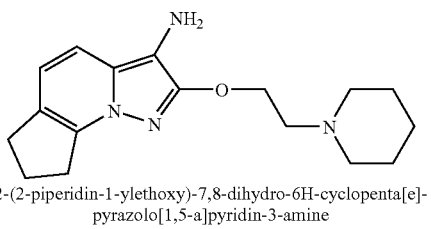

2-(2-piperidin-1-ylethoxy)-7,8-dihydro-6H-cyclopenta[e]-
pyrazolo[1,5-a]pyridin-3-amine

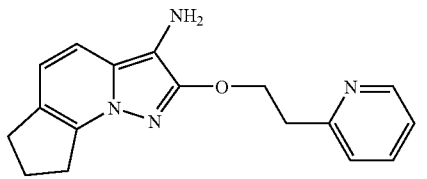

2-(2-pyridin-2-ylethoxy)-7,8-dihydro-6H-cyclopenta[e]pyrazolo-
[1,5-a]pyridin-3-amine

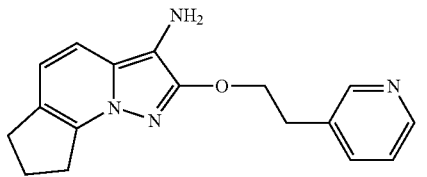

2-(2-pyridin-3-ylethoxy)-7,8-dihydro-6H-cyclophenta[e]pyrazolo-
[1,5-a]pyridin-3-amine

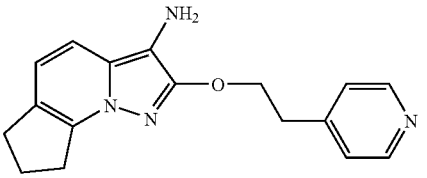

2-(2-pyridin-4-ylethoxy)-7,8-dihydro-6H-cyclopenta[e]pyrazolo-
[1,5-a]pyridin-3-amine

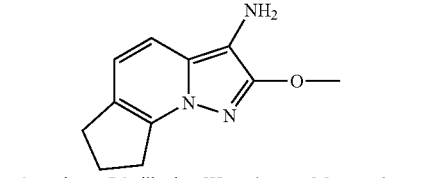

2-methoxy-7,8-dihydro-5H-cyclopenta[e]pyrazolo-
[1,5-a]pyridin-3-amine

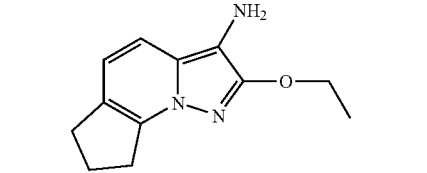

2-ethoxy-7,8-dihydro-6H-cyclopenta[e]pyrazolo[1,5-a]-
pyridin-3-amine

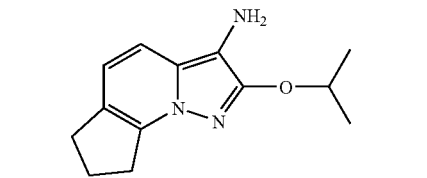

2-isopropoxy-7,8-dihdryo-6H-cyclopenta[e]pyrazolo[1,5-a]-
pyridin-3-amine

-continued

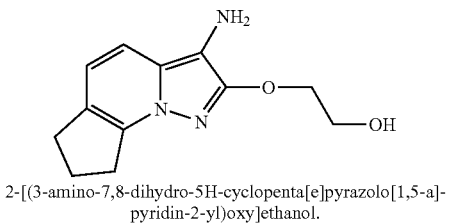

2-[(3-amino-7,8-dihydro-5H-cyclopenta[e]pyrazolo[1,5-a]-pyridin-2-yl)oxy]ethanol.

13. A composition according to claim 1 in which the compound of formula (I) is chosen from:
- 2-(3-aminopyrazolo[1,5-a]pyridin-2-ylamino)ethanol dihydrochloride,
- 1-(3-aminopyrazolo[1,5-a]pyridin-2-ylamino)propan-2-ol dihydrochloride,
- N-2-(3-imidazol-1-ylpropyl)pyrazolo[1,5-a]pyridine-2,3-diamine dihydrochloride,
- N-2-(2-pyrrolidin-1-ylethyl)pyrazolo[1,5-a]pyridine-2,3-diamine dihydrochloride,
- 2-(3-aminopyrazolo[1,5-a]pyridin-2-yloxy)ethanol dihydrochloride,
- N-2-(2-piperidin-1-ylethyl)pyrazolo[1,5-a]pyridine-2,3-diamine dihydrochloride,
- N-2-[2-(diisopropylamino)ethyl]pyrazolo[1,5-a]pyridine-2,3-diamine dihydrochloride,
- N-2-[2-(diethylamino)ethyl]pyrazolo[1,5-a]pyridine-2,3-diamine dihydrochloride,
- N-2-(2-pyridin-3-ylethyl)pyrazolo[1,5-a]pyridine-2,3-diamine dihydrochloride,
- N-2-(2-pyridin-4-ylethyl)pyrazolo[1,5-a]pyridine-2,3-diamine dihydrochloride,
- N-2-(2-pyridin-2-ylethyl)pyrazolo[1,5-a]pyridine-2,3-diamine diamine dihydrochloride,
- N-2-(2-piperazin-1-ylethyl)pyrazolo[1,5-a]pyridine-2,3-diamine,
- N-2-[2-(4-methylpiperazzin-1-yl)ethyl]pyridine-2,3-diamine dihydrochloride,
- N-2-(2-morpholin-4-ylethyl)pyrazolo[1,5-a]pyridine-2,3-diamine dihydrochloride,
- N-2-[2-(dimethylamino)ethyl]-7,8-dihydro-6H-cyclopenta[e]pyrazolo[1,5-a]pyridine-2, 3-diamine dihydrochloride,
- 2-[(3-amino-7,8-dihydro-6H-cyclopenta[e]pyrazolo[1,5-a]pyridin-2-yl)amino]ethanol hydrochloride,
- 2-methoxy-7,8-dihydro-6H-cyclopenta[e]pyrazolo[1,5-a]pyridin-3-amine hydrochloride,
- 2-isopropoxy-7,8-dihydro-6H-cyclopenta[e]pyrazolo[1,5-a]pyridin-3-amine hydrochloride,
- 2-[2-(dimethylamino)ethoxy]pyrazolo[1,5-a]pyridin-3-amine dihydrochloride,
- 2-(2-pyrrolidin-1-ylethoxy)pyrazolo[1,5-a]pyridin-3-amine dihydrochloride,
- 2-(2-piperidin-1-ylethoxy)pyrazolo[1,5-a]pyridin-3-amine dihydrochloride,
- 2-(2-morpholin-4-ylethoxy)pyrazolo[1,5-a]pyridin-3-amine dihydrochloride,
- 2-[2-(diisopropylamino)ethoxy]pyrazolo[1,5-a]pyridin-3-amine dihydrochloride,
- 2-(2-pyridin-2-ylethoxy)pyrazolo[1,5-a]pyridin-3-amine dihydrochloride,
- 2-(2-pyridin-3-ylethoxy)pyrazolo[1,5-a]pyridin-3-amine dihydrochloride,
- 2-(2-pyridin-4-ylethoxy)pyrazolo[1,5-a]pyridin-3-amine dihydrochloride, and
- N-5,N-5-dimethyl-2-methylsulphanylpyrazolo[1,5-a]pyridine-3,5-diamine dihydrochloride.

* * * * *

UNITED STATES PATENT AND TRADEMARK OFFICE
CERTIFICATE OF CORRECTION

PATENT NO.        : 7,635,394 B2
APPLICATION NO.   : 11/594967
DATED             : December 22, 2009
INVENTOR(S)       : Aziz Fadli, Laurent Vidal and Stéphane Sabelle It is certified that error appears in the above-identified patent and that said Letters Patent is hereby corrected as shown below:

Claim 2, col. 110, line 50, delete "an amino radical" after -- hydroxy radical --.

Claim 5, col. 111, line 40, insert -- alkyl, -- after -- C1-C6 --.

Claim 6, col. 112, line 15 "radicals" should read -- radical. -- and delete "and wherein $Z_1$ and $R_1$ together can not form $(C_1-C_4)$alkoxy radicals if $R_4$ and $R_5$ together can not form a saturated or unsaturated (hetero)cycle --.

Claim 12, col. 117, line 20, "4-propylpyrazin" should read -- 4-propylpiperazin --.

Claim 12, col. 119, line 20, "2-methanesulphenyl" should read -- 2-methanesulphonyl --.

Claim 12, col. 125, line 11, "5H" should read -- 6H --.

Claim 13, col. 125, line 31, "ethyll" should read -- ethyl] --.

Claim 13, col. 126, line 5-6, "N-2-[2-(4-methylpiperazzin-l-yl)ethyl]pyridine-2,3-diamine dihydrochloride," should read -- N-2-[2-(4-methylpiperazin-l-yl)ethyl]pyrazolo[1,5-a]pyridine-2,3-diamine dihydrochloride, --.

Signed and Sealed this

Eighth Day of June, 2010

David J. Kappos
*Director of the United States Patent and Trademark Office*